US009815873B2

(12) United States Patent
Couture et al.

(10) Patent No.: US 9,815,873 B2
(45) Date of Patent: Nov. 14, 2017

(54) METHOD FOR RECOVERING PLANT-DERIVED PROTEINS

(75) Inventors: Manon Couture, St. Augustine de Desmaures (CA); Dany Paquet, St. Jean Chrysostome (CA); Louis-Philippe Vezina, Neuville (CA)

(73) Assignee: MEDICAGO INC., Quebec (CA)

( * ) Notice: Subject to any disclaimer, the term of this patent is extended or adjusted under 35 U.S.C. 154(b) by 0 days.

(21) Appl. No.: 14/006,552

(22) PCT Filed: Mar. 23, 2012

(86) PCT No.: PCT/CA2012/050180
§ 371 (c)(1),
(2), (4) Date: Sep. 20, 2013

(87) PCT Pub. No.: WO2012/126123
PCT Pub. Date: Sep. 27, 2012

(65) Prior Publication Data
US 2014/0024104 A1    Jan. 23, 2014

Related U.S. Application Data

(60) Provisional application No. 61/466,889, filed on Mar. 23, 2011.

(51) Int. Cl.
*C07K 14/415*    (2006.01)
*C07K 1/14*    (2006.01)

(52) U.S. Cl.
CPC ............ *C07K 14/415* (2013.01); *C07K 1/145* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford | |
| 5,036,006 A | 7/1991 | Sanford | |
| 5,100,792 A | 3/1992 | Sanford | |
| 5,232,833 A | 8/1993 | Sanders | |
| 5,486,510 A | 1/1996 | Bouic | |
| 5,625,136 A | 4/1997 | Koziel | |
| 5,762,939 A | 6/1998 | Smith et al. | |
| 5,858,368 A | 1/1999 | Smith et al. | |
| 5,929,304 A * | 7/1999 | Radin ............... | C12N 15/8237 435/183 |
| 6,020,169 A | 2/2000 | Lee et al. | |
| 6,326,470 B1 | 12/2001 | Cosgrove | |
| 6,403,865 B1 | 6/2002 | Koziel et al. | |
| 6,489,537 B1 | 12/2002 | Rea et al. | |
| 7,125,978 B1 | 10/2006 | Vezina et al. | |
| 7,132,291 B2 | 11/2006 | Cardineau et al. | |
| 7,897,842 B2 | 3/2011 | Bakker et al. | |
| 2001/0006950 A1 | 7/2001 | Punnonen | |
| 2002/0088024 A1* | 7/2002 | Garger et al. ................. | 800/284 |
| 2004/0002061 A1 | 1/2004 | Kawaoka | |
| 2005/0015830 A1* | 1/2005 | Dorokhov et al. ........... | 800/278 |
| 2005/0048074 A1 | 3/2005 | Cardineau | |
| 2005/0059127 A1* | 3/2005 | Turpen et al. ................ | 435/183 |
| 2006/0252132 A1 | 11/2006 | Yang | |
| 2007/0207526 A1 | 9/2007 | Coit et al. | |
| 2007/0286873 A1 | 12/2007 | Williams | |
| 2009/0191309 A1 | 7/2009 | Rastogi et al. | |
| 2009/0311669 A1 | 12/2009 | Kawaoka | |
| 2010/0167376 A1 | 7/2010 | Hogan et al. | |
| 2010/0239610 A1 | 9/2010 | D'Aoust | |
| 2010/0310604 A1 | 12/2010 | D'Aoust | |
| 2011/0191915 A1 | 8/2011 | Couture | |
| 2011/0293650 A1 | 12/2011 | D'Aoust | |
| 2012/0178149 A1 | 7/2012 | Vezina | |
| 2012/0189658 A1 | 7/2012 | Couture | |
| 2013/0067807 A1 | 3/2013 | Vezina | |
| 2013/0142826 A1 | 6/2013 | D'Aoust | |
| 2013/0183341 A1 | 7/2013 | D'Aoust | |
| AU 2010265766 | 2/2012 | | |
| AU 2010300033 | 3/2012 | | |
| AU 2010300034 | 3/2012 | | |
| AU 2012231717 | 9/2013 | | |
| CA 2693956 | 7/2008 | | |
| CA 2693956 | 1/2009 | | |
| CA 2707235 | 1/2009 | | |
| CA 2707235 | 6/2009 | | |
| CA 2615372 | 1/2010 | | |
| CA 2730185 | 1/2010 | | |
| CA 2772962 | 1/2010 | | |
| CA 2762042 | 6/2010 | | |
| CA 2772962 | 9/2010 | | |

FOREIGN PATENT DOCUMENTS

| | | |
|---|---|---|
| AU | 2008278222 | 7/2008 |
| AU | 2009202819 | 1/2009 |
| AU | 2009202819 | 6/2009 |
| AU | 2008278222 | 1/2010 |
| AU | 2009267759 | 1/2010 |
| AU | 2010265766 | 6/2010 |
| AU | 2010300033 | 9/2010 |
| AU | 2010300034 | 9/2010 |

(Continued)

OTHER PUBLICATIONS

Sato, Y., and Beutler, E., Journal of Clinical Investigation 1993, vol. 91, pp. 1909-1917.*

(Continued)

*Primary Examiner* — Michelle F Paguio Frising
(74) *Attorney, Agent, or Firm* — Ballard Spahr LLP

(57) ABSTRACT

Methods of recovering plant-derived proteins or suprastructure proteins, are provided. The method may comprise obtaining a plant, or plant matter comprising apoplast-localized proteins, or suprastructure proteins, loosening the cell wall to produce a plant or plant matter having a loosened cell wall, thus allowing the release of apoplastic content through the cell wall to produce an apoplastic content fraction from the plant or plant matter, and recovering the apoplastic content fraction. The apoplastic content fraction comprises plant-derived proteins or suprastructure proteins.

19 Claims, 23 Drawing Sheets

(56) References Cited

FOREIGN PATENT DOCUMENTS

| | | |
|---|---|---|
| CA | 2772964 | 3/2011 |
| CN | 200980109781.5 | 1/2009 |
| CN | 200980134868.8 | 1/2009 |
| CN | 200880107072.9 | 6/2009 |
| CN | 200980109781.5 | 6/2009 |
| CN | 200980134868.8 | 1/2010 |
| CN | 201080042336.4 | 9/2010 |
| CN | 201080042333.0 | 3/2011 |
| CU | D2010006 | 7/2008 |
| CU | D2010006 | 1/2009 |
| CU | D2010152 | 1/2009 |
| CU | D2010152 | 6/2009 |
| EA | 201001198 | 1/2010 |
| EG | 2010010061 | 7/2008 |
| EG | 2010010061 | 1/2009 |
| EG | 1222/2010 | 6/2009 |
| EP | 2008783201 | 7/2008 |
| EP | 2009700061 | 1/2009 |
| EP | 2173886 | 4/2010 |
| EP | 2010791119 | 6/2010 |
| EP | 2010818190 | 9/2010 |
| EP | 2010818191 | 9/2010 |
| EP | 2238253 | 10/2010 |
| EP | 2307549 | 4/2011 |
| EP | 2010791119 | 5/2012 |
| EP | 2480560 | 8/2012 |
| EP | 2480658 | 8/2012 |
| EP | 2570484 | 3/2013 |
| GE | 11920 | 1/2009 |
| GE | 11920 | 6/2009 |
| ID | W-002010248 | 6/2009 |
| IL | 206967 | 1/2009 |
| IL | 206967 | 6/2009 |
| IL | 210215 | 1/2010 |
| IL | 218393 | 9/2010 |
| IL | 218422 | 9/2010 |
| IL | 218393 | 4/2012 |
| IL | 218422 | 4/2012 |
| JP | 2010516334 | 7/2008 |
| JP | 2010-516334 | 1/2009 |
| JP | 2011-516934 | 1/2009 |
| JP | 2010542486 | 1/2009 |
| JP | 2010-542486 | 6/2009 |
| JP | 2012516452 | 6/2010 |
| JP | 2012530059 | 9/2010 |
| JP | 2012530060 | 9/2010 |
| JP | 2012-530059 | 3/2011 |
| JP | 2012-530060 | 3/2011 |
| JP | 5551780 B2 | 7/2014 |
| KR | 1020107002538 | 7/2008 |
| KR | 1020107018343 | 1/2009 |
| KR | 1020117001798 | 1/2010 |
| KR | 1020107002538 | 3/2010 |
| KR | 1020107018343 | 11/2010 |
| MX | MX/a/2010/000525 | 7/2008 |
| MX | MX/a/2010/000525 | 1/2009 |
| MX | MX/a/2010/007962 | 1/2009 |
| MX | MX/a/2010/007962 | 6/2009 |
| MX | MX/a/2011/000459 | 1/2010 |
| MX | MX/a/2012/003372 | 9/2010 |
| MY | PI 2010000142 | 7/2008 |
| MY | PI 2010000142 | 1/2009 |
| MY | PI 2010003442 | 1/2009 |
| MY | PI 2010003442 | 6/2009 |
| NZ | 582360 | 7/2008 |
| NZ | 582360 | 1/2009 |
| NZ | 587108 | 1/2009 |
| NZ | 590144 | 1/2009 |
| NZ | 587108 | 6/2009 |
| NZ | 598481 | 3/2011 |
| NZ | 598508 | 3/2011 |
| NZ | 598481 A | 2/2014 |
| NZ | 598508 A | 2/2014 |
| PH | 12012500565 | 9/2010 |
| PH | 12012500566 | 9/2010 |
| PH | 12012500565 | 3/2011 |
| PH | 12012500566 | 3/2011 |
| RU | 2011-105073 | 1/2010 |
| RU | 2012101946 | 6/2010 |
| RU | 2012115661 | 9/2010 |
| RU | 2012115996 | 9/2010 |
| RU | 2012-115661 | 3/2011 |
| RU | 2012-115996 | 3/2011 |
| SG | 201000090-9 | 1/2009 |
| SG | 201009568-5 | 1/2009 |
| SG | 201201471-8 | 9/2010 |
| SG | 158301 | 4/2012 |
| TH | 1201001223 | 9/2010 |
| TH | 1201001239 | 9/2010 |
| TH | 1201001223 | 3/2011 |
| TH | 1201001239 | 3/2011 |
| WO | WO 86/03224 | 6/1986 |
| WO | WO 00/09725 | 2/2000 |
| WO | WO 00/37663 | 6/2000 |
| WO | WO 00/56906 | 9/2000 |
| WO | WO 00/63400 | 10/2000 |
| WO | WO 02/074795 | 9/2002 |
| WO | WO 03/025124 | 3/2003 |
| WO | WO 03/068163 | 8/2003 |
| WO | WO 03/068993 | 8/2003 |
| WO | WO 2004/098530 | 11/2004 |
| WO | WO 2004/098533 | 11/2004 |
| WO | WO 2005/020889 | 3/2005 |
| WO | WO 2006/016380 | 2/2006 |
| WO | WO 2006/119516 | 11/2006 |
| WO | WO 2007/011904 | 1/2007 |
| WO | WO 2007/019094 | 2/2007 |
| WO | WO 2007/047831 | 4/2007 |
| WO | WO 2007/095318 | 8/2007 |
| WO | WO 2007/130327 | 11/2007 |
| WO | WO 2007/135480 | 11/2007 |
| WO | WO 2008/054540 | 5/2008 |
| WO | WO 2008/060669 | 5/2008 |
| WO | PCT/CA2008/001281 | 7/2008 |
| WO | WO 2008/087391 | 7/2008 |
| WO | WO 2008/151440 | 12/2008 |
| WO | PCT/CA2009/000032 | 1/2009 |
| WO | WO 2009/008573 | 1/2009 |
| WO | WO 2009/009876 | 1/2009 |
| WO | WO-2009/009876 A1 | 1/2009 |
| WO | WO 2009/026397 | 2/2009 |
| WO | WO 2009/076778 | 6/2009 |
| WO | WO 2010/003225 | 1/2010 |
| WO | WO 2010/003235 | 1/2010 |
| WO | WO 2010/006452 | 1/2010 |
| WO | WO 2010/025285 | 3/2010 |
| WO | PCT/CA2010/000983 | 6/2010 |
| WO | WO 2010/077712 | 7/2010 |
| WO | PCT/CA2010/001488 | 9/2010 |
| WO | PCT/CA2010/001489 | 9/2010 |
| WO | WO 2010/148511 | 12/2010 |
| WO | WO 2011/035422 | 3/2011 |
| WO | WO 2011/035423 | 3/2011 |
| WO | PCT/CA2012/050180 | 3/2012 |
| WO | WO 2012/061815 | 5/2012 |
| WO | WO 2012/083445 | 6/2012 |
| WO | WO 2012/126123 | 9/2012 |

OTHER PUBLICATIONS

Castilho, A., Pabst, M., Leonard, R., Veit, C., Altmann, F., Mach, L., Glossl, J., Strasser, R.,, and Steinkellner, H. Plant Physiology 2008, vol. 147, pp. 331-339.*

Gelvin, S.B., Microbiology and Molecular Biology Reviews 2003, vol. 67, pp. 16-37.*

Patent Examination Report No. 1 issued Nov. 6, 2013 for Australian patent application AU 2010300034 (Applicant—Medicago Inc. // 1st Named Inventor —L.P. Vezina) (4 pages).

Office Action dated Jul. 9, 2012 for Canadian patent application CA 2,772,962 (Applicant—Medicago Inc. // 1st Named Inventor—L.P. Vezina) (3 pages).

(56) References Cited

OTHER PUBLICATIONS

Second Office Action dated Apr. 24, 2014 for Chinese patent application CN 201080042336.4 (Applicant—Medicago Inc. // 1st Named Inventor—L.P. Vezina) (10 pages).
Search Report dated Feb. 27, 2014 for Singapore patent application SG 201201471-8 (Applicant—Medicago Inc. // 1st Named Inventor—L.P. Vezina) (6 pages).
Written Opinion issued Feb. 27, 2014 for Singapore patent application SG 201201471-8 (Applicant—Medicago Inc. // 1st Named Inventor—L.P. Vezina) (7 pages).
Office Action dated Feb. 19, 2014 for MX patent application MX/a/2012/003372 (Applicant—Medicago Inc. // 1st Named Inventor—L.P. Vezina) (3 pages).
Office Action dated Nov. 19, 2013 by the State Intellectual Property Office of People's Republic of China for CN patent application No. 201080042333.0 (Medicago, Inc.) (11 pages).
Office Action dated Jul. 29, 2013 by the State Intellectual Property Office of People's Republic of China for CN patent application No. 201080042336.4 (Medicago, Inc.) (10 pages).
Article 94(3) Communication dated Oct. 23, 2013 by the European Patent Office for EP patent application No. 10818190.0 filed on Sep. 21, 2010 (Medicago, Inc. // Vezina et al.) (4 pages).
Article 94(3) Communication dated Oct. 23, 2013 by the European Patent Office for EP patent application No. 10818191.8 filed on Sep. 21, 2010 (Medicago, Inc. // Vezina et al.) (4 pages).
Official Action dated by the Japanese Patent Office on Oct. 22, 2013 for JP patent application No. 2012-530059 (3 pages).
Official Action dated by the Japanese Patent Office on Jun. 11, 2013 for JP patent application No. 2012-530059 (2 pages).
Official Action dated by the Japanese Patent Office on Oct. 29, 2013 for JP patent application No. 2012-530060 (4 pages).
Methods for Plant Molecular Biology, Chapter 23: Protoplasts: Isolation, culture, Plant Regeneration, (Weissbach and Weissbach, eds.), Academic Press Inc., 1988), pp. 355-383.
Protoplast Isolation. Retrieved from www.molecular-plant-biotechnology.info on Aug. 30, 2012 (1 page) (Author Unknown).
Schopfer P. (2001) Hydroxyl radical-induced cell-wall loosening in vitro and in vivo: implications for the control of elongation growth. The Plant Journal, 28(6), 679-688.
U.S. Appl. No. 61/022,775, filed Jan. 22, 2008, M.A. D'Aoust.
U.S. Appl. No. 12/863,772, filed Aug. 26, 2010, M.A. D'Aoust.
U.S. Appl. No. 13/748,531, filed Jan. 23, 2013, M.A. D'Aoust.
U.S. Appl. No. 61/244,786, filed Sep. 22, 2009, L.P. Vezina.
U.S. Appl. No. 13/497,757, filed Mar. 22, 2012, L.P. Vezina.
U.S. Appl. No. 13/497,767, filed Mar. 22, 2012, L.P. Vezina.
U.S. Appl. No. 61/446,889, filed Mar. 23, 2011, M. Couture.
U.S. Appl. No. 61/220,161, filed Jun. 24, 2009, M. Couture.
U.S. Appl. No. 13/380,346, filed Apr. 17, 2012, M. Couture.
U.S. Appl. No. 61/022,755, filed Jan. 22, 2008, M.A. D'Aoust.
U.S. Appl. No. 61/013,272, filed Dec. 12, 2007, M.A. D'Aoust.
U.S. Appl. No. 60/990,603, filed Nov. 27, 2007, M.A. D'Aoust.
U.S. Appl. No. 60/959,414, filed Jul. 13, 2007, M.A. D'Aoust.
U.S. Appl. No. 12/669,033, filed Jun. 11, 2010, M.A. D'Aoust.
U.S. Appl. No. 13/374,886, filed Jan. 4, 2013, M.A. D'Aoust.
U.S. Appl. No. 61/220,161, filed Apr. 17, 2012, Couture.
International Preliminary Report on Patentability dated Sep. 24, 2013 for PCT/CA2012/050180 filed Mar. 23, 2012 and published as WO 2012/126123 on Sep. 27, 2012 (Medicago, Inc. // Couture et al.) (8 pages).
International Search Report dated Sep. 27, 2012 for PCT/CA2012/050180 filed Mar. 23, 2012 and published as WO 2012/126123 on Sep. 27, 2012 (Medicago, Inc. // Couture et al.) (5 pages).
Written Opinion dated Jun. 11, 2012 for PCT/CA2012/050180 filed Mar. 23, 2012 and published as WO 2012/126123 on Sep. 27, 2012 (Medicago, Inc. // Couture et al.) (7 pages).
International Preliminary Report on Patentability dated Jan. 4, 2012 for PCT/CA2010/000983 filed Jun. 25, 2010 and published as WO 2010/148511 on Dec. 29, 2010 (Medicago, Inc. // Couture et al.) (9 pages).
International Search Report dated Dec. 29, 2010 for PCT/CA2010/000983 filed Jun. 25, 2010 and published as WO 2010/148511 on Dec. 29, 2010 (Medicago, Inc. // Couture et al.) (5 pages).
Written Opinion dated Sep. 14, 2010 for PCT/CA2010/000983 filed Jun. 25, 2010 and published as WO 2010/148511 on Dec. 29, 2010 (Medicago, Inc. // Couture et al.) (8 pages).
International Preliminary Report on Patentability dated Nov. 12, 2009 for PCT/CA2008/001281 filed Jul. 11, 2008 and published as WO 2009/009876 on Jan. 22, 2009 (Medicago, Inc. // D'Aoust et al.) (11 pages).
International Search Report and Written Opinion dated Oct. 7, 2008 for PCT/CA2008/001281 filed Jul. 11, 2008 and published as WO 2009/009876 on Jan. 22, 2009 (Medicago, Inc. // D'Aoust et al.) (15 pages).
International Preliminary Report on Patentability dated Jan. 11, 2011 for PCT/CA2009/000941 filed Jul. 7, 2009 and published as WO 2010/003235 on Jan. 14, 2010 (Medicago, Inc. // Couture et al.) (1 pages).
International Search Report and Written Opinion dated Sep. 10, 2009 for PCT/CA2009/000941 filed Jul. 7, 2009 and published as WO 2010/003235 on Jan. 14, 2010 (Medicago, Inc. // Couture et al.) (13 pages).
International Preliminary Report on Patentability dated Nov. 5, 2010 for application PCT/CA2009/001040 filed Jul. 15, 2009 and published as WO 2010/006452 (Medicago, Inc. // Couture et al.) (14 pages).
International Search Report and Written Opinion dated Nov. 10, 2009 for PCT/CA2009/001040 filed Jul. 15, 2009 and published as WO 2010/006452 on Jan. 14, 2010 (Medicago, Inc. // Couture et al.) (13 pages).
International Preliminary Report on Patentability dated Jul. 27, 2010 for PCT/CA2009/000032 filed Jan. 12, 2009 and published as WO 2009/076778 on Jun. 25, 2009 (Medicago, Inc. // D'Aoust et al.) (9 pages).
International Search Report and Written Opinion dated Apr. 30, 2009 for PCT/CA2009/000032 filed Jan. 12, 2009 and published as WO 2009/076778 on Jun. 25, 2009 (Medicago, Inc. // D'Aoust et al.) (17 pages).
International Preliminary Report on Patentability dated Nov. 5, 2010 for PCT/CA2009/000926 filed Jul. 2, 2009 and published as WO 2010/003225 on Jan. 14, 2010 (Medicago, Inc. // D'Aoust et al.) (15 pages).
International Search Report and Written Opinion dated Oct. 1, 2009 for PCT/CA2009/000926 filed Jul. 2, 2009 and published as WO 2010/003225 on Jan. 14, 2010 (Medicago, Inc. // D'Aoust et al.) (17 pages).
International Search Report dated Jan. 6, 2011 for PCT/CA2010/001488 filed Sep. 21, 2010 and published as WO 2011/035422 on Mar. 31, 2011 (Medicago, Inc. // Vezina et al.) (5 pages).
Written Opinion dated Jan. 6, 2011 for PCT/CA2010/001488 filed Sep. 21, 2010 and published as WO 2011/035422 on Mar. 31, 2011 (Medicago, Inc. // Vezina et al.) (6 pages).
International Preliminary Report on Patentability dated Mar. 27, 2012 for PCT/CA2010/001488 filed Sep. 21, 2010 and published as WO 2011/035422 on Mar. 31, 2011 (Medicago, Inc. // Vezina et al.) (7 pages).
International Search Report dated Nov. 30, 2010 for PCT/CA2010/001489 filed Sep. 21, 2010 and published as WO 2011/035423 on Mar. 31, 2011 (Medicago, Inc. // Vezina et al.) (4 pages).
Written Opinion dated Nov. 30, 2010 for PCT/CA2010/001489 filed Sep. 21, 2010 and published as WO 2011/035423 on Mar. 31, 2011 (Medicago, Inc. // Vezina et al.) (6 pages).
International Preliminary Report on Patentability dated Mar. 27, 2012 for PCT/CA2010/001489 filed Sep. 21, 2010 and published as WO 2011/035423 on Mar. 31, 2011 (Medicago, Inc. // Vezina et al.) (7 pages).
Air GM. Sequence relationships among the hemagglutinin genes of 12 subtypes of influenza A virus, Proc Natl Acad Sci USA 78, pp. 7639-7643 (1981).
Arntzen, et al. Plant-derived vaccines and antibodies: potential and limitations, Vaccine 23, pp. 1753-1756 (2005).

(56) References Cited

OTHER PUBLICATIONS

Ausubel, et al. Chapter 9: Transfection by Electroporation, Current Protocols in Molecular Biology, John Wiley & Sons, New York (1998 and Supplements in 2001).
Aymard-Henry M, et al. Influenzavirus neuraminidase and neuraminidase-inhibition test procedures. Bull. Org. mond. Sante. Bull. Wid Hlth Org. 48, pp. 199-202 (1973).
Bao, et al. The influenza virus resource at the National Center for Biotechnology Information, J Virol 82, pp. 596-601 (2008).
Berger, et al. Plant sterols: factors affecting their efficacy and safety as functional food ingredients, Lipids in Health and Disease 3, pp. 1-19 (2004).
Berman, et al. Correspondence: announcing the worldwide Protein Data Bank, Nat Struct Biol 10, p. 980 (2003).
Bilang, et al. The 3'-terminal region of the hygromycin-B-resistance gene is important for its activity in Escherichia coli and Nicotiana tabacum, Gene 100, pp. 247-250 (1991).
Bollag, et al. Purified JC virus T antigen derived from insect cells preferentially interacts with binding site II of the viral core origin under replication conditions, Virology 218, pp. 81-93 (1996).
Borisjuk, et al. Expression of avian flu antigen for bird immunization, Plant Biology & Botany Abstract Search (1 page) (2007).
Bouic PJD, et al. Plant sterols and sterolins: a review of their immune-modulating properties, Alt Med Rev 4, pp. 170-177 (1999).
Bouic PJD. Sterols and sterolins: new drugs for the immune system?, Drug Discovery Today 7, pp. 775-778 (2002).
Bouic PJD. The role of phytosterols and phytosterolins in immune modulation: a review of the past 10 years, Curr Opin Clin Nutrition Metabolic Care 4, pp. 471-475 (2001).
Bright RA, et al. Impact of glycosylation on the immunogenicity of a DNA-based influenza H5 HA vaccine, Virology 308, pp. 270-278 (2003).
Bright RA, et al. Influenza virus-like particles elicit broader immune responses than whole virion inactivated influenza virus or recombinant hemagglutinin, Vaccine 25, pp. 3871-3878 (2007).
Brigneti, et al. Viral pathogenicity determinants are suppressors of transgene silencing in Nicotiana benthamiana, EMBO J 17, pp. 6739-6746 (1998).
Chandler GL. Influenza hemagglutinin expression in Nicotiana tabacum and Nicotiana benthamiana, Dissertation, Baylor University (70 pages) (2007).
Chandrasekaran, et al. Glycan topology determines human adaptation of avian H5N1 virus hemagglutinin, Nat Biotechnol 26, pp. 107-113 (2008).
Charland N, et al. An innovative VLP-based technology to respond to global influenza vaccine needs, Seasonal and Pandemic Influenza Conference (2 pages) (2008).
Chen BJ, et al. Influenza virus hemagglutinin and neuraminidase, but not the matrix protein, are required for assembly and budding of plasmid-derived viruslike particles, J Virol 81, pp. 7111-7123 (2007).
Chen, et al. Stabilizing the glycosylation pattern of influenza B hemagglutinin following adaptation to growth in eggs, Vaccine 26, pp. 361-371 (2008).
Chiba M, et al. Diverse suppressors of RNA silencing enhance agroinfection by a viral replicon, Virology 346, pp. 7-14 (2006).
Cosgrove, D. Loosening of Plant Cell Walls by Expansins, Nature, vol. 407, pp. 321-326 (2000).
Crawford, et al. Baculovirus-derived hemagglutinin vaccines protect against lethal influenza infections by avian H5 and H7 subtypes, Vaccine 17, pp. 2265-2274 (1999).
Cross, et al. Studies on influenza haemagglutinin fusion peptide mutants generated by reverse genetics, EMBO J 20, pp. 4432-4442 (2001).
D'Aoust MA, et al. Influenza virus-like particles produced by transient 1-38 expression in Nicotiana benthamiana induce a protective immune response against a lethal viral challenge in mice, Plant Biotechnol J 6, pp. 930-940 (2008).

D'Aoust MA, et al. The production of hemagglutinin-based virus-like 1-38 particles in plants: a rapid, efficient and safe response to pandemic influenza, Plant Biotechnol J 8, pp. 607-619 (2010).
Davey MR, et al. Plant protoplasts: status and biotechnological perspectives, Biotechnology Advances 23, pp. 131-171 (2005).
DeBlock M, et al. Transformation of Brassica napus and Brassica oleracea using Agrobacterium tumefaciens and the expression of the bar and neo genes in the transgenic plants, Plant Physiology 91, pp. 694-701 (1989).
Diaz-Vivancos P, et al. The apoplastic antioxidant system in Prunus: response to long-term plum pox virus infection, J Exp Bot 57, pp. 3813-3824 (2006).
Firek et al. Secretion of a functional single-chain Fv protein in transgenic tobacco plants and cell suspension cultures, Plant Molecular Biology, vol. 23, Issue 4, pp. 861-870 (1993).
Fischer R, et al. Affinity-purification of a TMV-specific recombinant full-size antibody from a transgenic tobacco suspension culture, J Immunol Meth 226, pp. 1-10 (1999).
Fischer, et al. Towards molecular farming in the future: moving form diagnostic protein and antibody production in microbes to plants, Biotechnology and Applied Biochemistry, vol. 30, pp. 101-108 (1999).
Flandorfer, et al. Chimeric influenza A viruses with a functional influenza B virus neuraminidase or hemagglutinin, J Virol 77, pp. 9116-9123 (2003).
Frugis G, et al. MsJ1, an alfalfa DnaJ-like gene, is tissue-specific and transcriptionally regulated during cell cycle, Plant Mol Biol 40, pp. 397-408 (1999).
Galarza, et al. Virus-like particle (VLP) vaccine conferred complete protection against a lethal influenza virus challenge, Viral Immunol 18, pp. 244-251 (2005).
Gallagher, et al. Addition of carbohydrate side chains at novel sites on influenza virus hemagglutinin can modulate the folding, transport, and activity of the molecule, J Cell Biol 107, pp. 2059-2073 (1988).
Gallagher, et al. Glycosylation requirements for intracellular transport and function of the hemagglutinin of influenza virus, J Virol 66, pp. 7136-7145 (1992).
Gamblin, et al. The structure and receptor binding properties of the 1918 influenza hemagglutinin, Science 303, pp. 1838-1842 (2004).
Garcea & Gissmann. Virus-like particles as vaccines and vessels for the delivery of small molecules, Pharmaceut Biotechnol 15, pp. 513-517 (2004).
Garten, et al. Antigenic and genetic characteristics of swine-origin 2009 A(H1N1) Influenza viruses circulating in Humans. Science, vol. 325, pp. 197-201 (2009).
Garten, et al. Emergence of a Novel Swine-Origin Influenza a (H1N1) Virus in Humans. New England Journal of Medicine, 360(25): 2605-2515. (2009).
Garten. Influenza A Virus (A/California/04/2009 H1N1) segment 4 hamegglutinin (HA) gene, Genbank Acces. FJ966082 (2009).
Gillim-Ross, et al. Emerging respiratory viruses: challenges and vaccine strategies, Clin Microbiol Rev 19, pp. 614-636 (2006).
Giridhar G, et al. Increased protoplast yield from oat leaves and bean internodes by non-injurious mechanical perturbation, Protoplasma 151, pp. 151-157 (1989).
Giritch, et al. Rapid High-Yield Expression of Full-Size IgG Antibodies in Plants Coinfected with Noncompeting Viral Vectors, PNAS, vol. 103, No. 40, pp. 14701-14706 (2006).
Golovkin, et al. Expression of avian flu antigen for bird immunization, Plant Biol Bot, 1 page. (2007) (Abstract).
Gomez-Puertas, et al. Efficient formation of influeza virus-like particles: dependence on the expression levels of viral proteins, J Gen Virol 80, pp. 1635-1645 (1999).
Gomez-Puertas, et al. Influenza virus matrix protein is the major driving force in virus budding, J Virol 74, pp. 11536-11547 (2000).
Gomord & Faye. Posttranslational modification of therapeutic proteins in plants, Curr Opin Plant Biol 7, pp. 171-181 (2004).
Gomord, et al. Biopharmaceutical Production in Plants: Problems, Solutions and Opportunities, Trends in Biotechnology, vol. 23, No. 11, pp. 559-565 (2005).

(56) References Cited

OTHER PUBLICATIONS

Greco R, et al. Production of recombinant HIV-1/HBV virus-like particles in Nicotiana tabacum and Arabidopsis thaliana plants for a bivalent plant-based vaccine, Vaccine 25, pp. 8228-8240 (2007).
Grgacic & Anderson. Virus-like particles: Passport to immune recognition, Methods 40, pp. 60-65 (2006).
Grierson & Covey. Chapter 7: Genetic Transformation of Plants by Agrobacterium, in Plant Molecular Biology (19 pages) (1988).
Grierson & Covey. Chapter 8: Plant Viruses, in Plant Molecular Biology (26 pages) (1988).
Grierson, et al. Chapter 9: Genetic Engineering of Plants, in Plant Molecular Biology (20 pages) (1988).
Guerche, et al. Direct gene transfer by electroporation in Brassica napus, Plant Science 52, pp. 111-116 (1987).
Gupta, et al. O-Glycbase version 4.0: a revised database of O-glycosylated proteins, Nucl Acids Res 27, pp. 370-372 (1999).
Hahn BS, et al. Expression of hemagglutinin-neuraminidase protein of Newcastle disease virus in transgenic tobacco, Plant Biotechnol Rep 1, pp. 85-92 (2007).
Hamilton A, et al. Two classes of short interfering RNA in RNA silencing, EMBO J 21, pp. 4671-4679 (2002).
Harbury, et al. A switch between the two-, three-, and four-stranded coiled coils in GCN4 leucine zipper mutants, Science 262, pp. 1401-1407 (1993).
Hartl FU. Molecular chaperones in cellular protein folding, Nature 381, pp. 571-580 (1996).
Hellwig, et al. Plant Cell Cultures for the Production of Recombinant Proteins, Nature Biotechnology, vol. 22, No. 11, pp. 1415-1422 (2004).
Horimoto, et al. Generation of influenza A viruses with chimeric (Type A/B) hemagglutinins, J Virol 77, pp. 8031-8038 (2003).
Horsch, et al. A simple and general method for transferring genes into plants, Science 227, pp. 1229-1231 (1985).
Houston, N., et al. Phylogenetic Analyses Identify 10 Classes of the Protein Disulfide Isomerase Family in Plants, Including Single-Domain Protein Disulfide Isomerase-Related Proteins. Plant Physiology, vol. 137, pp. 762-778 (2005).
Howell, et al. Cloned Cauliflower Mosaic Virus DNA infects turnips (*Brassica rapa*), Science 208, p. 1265 (1980).
Huang Z, et al. Virus-like particle expression and assembly in plants: 1-38 hepatitis B and Norwalk viruses, Vaccine 23, pp. 1851-1858 (2005).
Huang, et al. A DNA replicon system for rapid high-level production of virus-like particles in plants, Biotechnol Bioeng 103, 706-714 (2009).
Huang, et al. High Level Rapid Production of Full-Size Monoclonal Antibodies in Plants by a Single-Vector DNA Replicon System, Biotechnology System, Biotechnology and Bioengineering, vol. 106, No. 1, (19 pages) (2010).
Huang, et al. Plant-derived measles virus hemagglutinin protein induces neutralizing antibodies in mice, Vaccine 19, pp. 2163-2171 (2001).
Hull, et al. Human-Derived, Plant-Produced monoclonal Antibody for the Treatment of Anthrax, Vaccine 23, pp. 2082-2086 (2005).
Influenza A virus (A/California/4/2009(H1N1)) segment 4 hemagglutinin (HA) gene, Complete DNA Sequence, GenBank (2 pages) (Aug. 2010).
Ito T, et al. Receptor specificity of Influenza A viruses correlates with the agglutination of erythrocytes from different animal species, Virology 227, pp. 493-499 (1997).
Johansen, et al. Silencing on the Spot. Induction and Suppression of RNA Silencing in the Agrobacterium-Mediated Transient Expression System, Plant Physiology, vol. 126, No. 3, pp. 930-938 (2001).
Johansson BE. Immunization with influenza A virus hemagglutinin and neuraminidase produced in recombinant baculovirus results in a balanced and broadened immune response superior to conventional vaccine, Vaccine 17, pp. 2073-2080 (1999).
Kanda Y, et al. Comparison of biological activity among nonfucosylated therapeutic IgG1 antibodies with three different N-linked Fc oligosaccharides: the high-mannose, hybrid, and complex types, Glycobiol 17, pp. 104-118 (2007).
Kang SM, et al. Influenza vaccines based on virus-like particles, Virus Res 143, pp. 140-146 (2009).
Kaufman PB, et al. Chapter 16: Gene Tranfer and Expression in Plants, in Handbook of Molecular and Cellular Methods in Biology and Medicine (29 pages) (1995).
Klein, et al. High-velocity microprojectiles for delivering nucleic acids into living cells, Nature 327, pp. 70-73 (1987).
Knossow, et al. Variation and infectivity neutralization in influenza, Immunology 119, pp. 1-7 (2006).
Kobayashi, et al. Chaperones Hsp70 and Hsp40 Suppress Aggregate Formation and Apoptosis in Cultured Neuronal Cells Expressing Truncated Androgen Receptor Protein with Expanded Polyglutamine Tract, J Biol.1 Chem., vol. 275, No. 12, pp. 8772-8778 (2000).
Latham, et al. Formation of wild-type and chimeric influenza virus-like particles following simultaneous expression of only four structural proteins, J Virol 75, pp. 6154-6165 (2001).
Lefebvre, et al. Characterization of lipid rafts from Medicago truncatula root plasma membranes: a proteomic study reveals the presence of a raft-associated redox system, Plant Physiol 144, pp. 402-418 (2007).
Lin, et al. Genomic analysis of the Hsp70 superfamily in Arabidopsis thaliana, Cell Stress & Chaperones, pp. 201-208 (2001).
Liu & Lomonossoff. Agroinfection as a rapid method for propagating Cowpea mosaic virus-based constructs, J Virol Meth 105, pp. 343-348 (2002).
Low D, et al. Future of antibody purification, J Chromatography B 848, pp. 48-63 (2007).
Ma, et al. The production of recombinant pharmaceutical proteins in plants, Nature Reviews Genetics, vol. 4, pp. 794-805 (2003).
Macala, et al. Analysis of brain lipids by high performance thin-layer chromatography and densitometry, J Lipid Res 24, pp. 1243-1250 (1983).
Macario, AJL. Heat-shock proteins and molecular chaperones: implications for pathogenesis, diagnostics, and therapeutics, Int J Clin Lab Res 25, pp. 59-70 (1995).
Mansour, et al. Plasma membrane lipid alterations induced by NaCl in winter wheat roots, Physiologia Plantarum 92, pp. 473-478 (1994).
Marozin S, et al. Antigenic and genetic diversity among swine influenza A H1N1 and H1N2 viruses in Europe, J Gen Virol 83, pp. 735-745 (2002).
Mason HS, et al. Expression of hepatitis B surface antigen in transgenic plants, Proc Natl Acad Sci USA 89, pp. 11745-11749 (1992).
Mason HS, et al. Expression of Norwalk virus capsid protein in transgenic tobacco and potato and its oral immunogenicity in mice, Proc Natl Acad Sci USA 93, pp. 5335-5340 (1996).
Mattanovich, et al. Efficient transformation of *Agrobacterium* spp. by electroporation, Nucl Acids Res 17, p. 6747 (1989).
McCauley & Mahy. Structure and function of the influenza virus genome, Biochem J 211, pp. 281-294 (1983).
McCormick AA, et al. Rapid production of specific vaccines for lymphoma by expression of the tumor-derived single-chain Fv epitopes in tobacco plants, Proc Natl Acad Sci USA 96, pp. 703-708 (1999).
Medeiros R, et al. Hemagglutinin residues of recent human A (H3N2) Influenza viruses that contribute to the inability to agglutinate chicken erythrocytes, Virology 289, pp. 74-85 (2001).
Mena I, et al. Rescue of a synthetic chloramphenicol acetyltransferase RNA into influenza virus-like particles obtained from recombinant plasmids, J Virol 70, pp. 5016-5024 (1996).
Mett, et al. A plant-produced influenza subunit vaccine protects ferrets against virus challenge, Influenza and Other Respiratory Viruses 2, pp. 33-40 (2008).
Miki & Iyer. Chapter 35: Fundamentals of Gene Transfer in Plants, in Plant Metabolism (23 pages) (1997).
Moehnke, et al. The expression of a mountain cedar allergen comparing plant-viral apoplastic and yeast expression systems, Biotechnol Lett 30, pp. 1259-1264 (2008).

(56) References Cited

OTHER PUBLICATIONS

Mongrand S, et al. Lipid rafts in higher plant cells: purification and characterization of Triton X-100-insoluble microdomains from Tobacco plasma membrane, J Bilo Chem 279, pp. 36277-36286 (2004).
Musiychuk K, et al. A launch vector for the production of vaccine antigens in plants, Influenza Other Resp Vir 1, pp. 19-25 (2007).
Nakahara, et al. Glycoconjugate Data Bank: Structures—an annotated glycan primary structure verification service, Nucl Acids Res 36, pp. D368-D371 (2008).
Nayak & Reichl. Neuraminidase activity assays for monitoring MDCK cell culture derived influenza virus, J Virol Meth 122, pp. 9-15 (2004).
Nemchinov, et al. Transient expression of the ectodomain of matrix protein 2 (M2e) of avian influenza A virus in plants. Protein Expression and Purification, vol. 56, pp. 153-159 (2007).
Neuhause G, et al. Transgenic rapeSeed plants obtained by the microinjection of DNA into microspore-derived embryoids, Theor Appl Genet 75, pp. 30-36 (1987).
Neumann, et al. Plasmid-driven formation of influenza virus-like particles, J Virol 74, pp. 547-551 (2000).
Newell JM, et al. Vacuole development in cultured evacuolated oat mesophyll protoplasts, J Exp Botany 49, pp. 817-827 (1998).
Nishimura, et al. Isolation of intact plastids from protoplasts from Castor Bean endosperm, Plant Physiol 62, pp. 40-43 (1978).
Nuttall, et al. ER-resident chaperone interactions with recombinant antibodies in transgenic plants, Eur J Biochem 269, pp. 6042-6051 (2002).
Olsen, et al. Immunogenicity and efficacy of baculovirus-expressed and DNA-based equine influenza virus hemagglutinin vaccines in mice, Vaccine 15, pp. 1149-1156 (1997).
Parsell DA & Lindquist S. The function of heat-shock proteins in stress tolerance: degradation and reactivation of damaged proteins, Ann Rev Genet 27, pp. 437-496 (1993).
Paszkowski & Saul. Direct Gene Transfer to Plants, in Methods for Plant Molecular Biology (19 pages) (1988).
Pereira-Leal JB, et al. The origins and evolution of functional modules: lessons from protein complexes, Philos Trans R Soc Lond B Biol Sci 361, pp. 507-517 (2006).
Petersen & Alfermann. Chapter 17: Plant Cell Cultures. Biotechnology Set, Second Edition, Section 1.3, pp. 578-580 (2008).
Plotkin, et al. Hemagglutinin sequence clusters and the antigenic evolution of influenza A virus, Proc Natl Acad Sci USA 99, pp. 6263-6268 (2002).
Potrykus I, et al. Protoplasts: Isolation, Culture, Plant Regeneration, in Methods for Plant Molecular Biology (31 pages) (1988).
Potter & Heller. Transfection by electroporation, Curr Prot Mol Biol (12 pages) (2003).
Power JB, et al. Fusion and Transformation of Plant Protoplasts, in Methods for Plant Molecular Biology (19 pages) (1988).
Pushko P, et al. Influenza virus-like particles comprised of the HA, NA, and M1 proteins of H9N2 influenza virus induce protective immune responses in BALB/c mice, Vaccine 23, pp. 5751-5759 (2005).
Pwee, et al. The pea plastocyanin promoter directs cell-specific but not full light-regulated expression in transgenic tobacco plants, Plant J 3, pp. 437-449 (1993).
Quan FS, et al. Virus-like particle vaccine induces protective immunity against homologous and heterologous strains of influenza virus, J Virol 81, pp. 3514-3524 (2007).
Razdan MK. Chapter 12: Somatic Hybridisation and Cybridisation, in Introduction to Plant Tissue Culture (30 pages) (2003).
Regnard, et al. High Level Protein Expression in Plants Through the Use of a Novel Autonomously Replicating Geminivirus Shuttle Vector, Plant Biotechnology Journal, vol. 8, pp. 38-46 (2010).
Rivard, et al. An in-built proteinase inhibitor system for the protection of recombinant proteins recovered from transgenic plants, Plant Biotechnology Journal, vol. 4, No. 3, pp. 359-368 (2006).
Rowe, et al. Detection of antibody to avian influenza A (H5N1) virus in human serum by using a combination of serologic assays, J Clin Microbiol 37, pp. 937-943 (1999).
Roy, et al. Virus-like particles as a vaccine delivery system: myths and facts, Human Vaccines 4, pp. 5-12 (2008).
Saelens, et al. Protection of Mice Against a Lethal Influenza Virus Challenge After Immunization with Yeast-Derived Secreted Influenza Virus Hemagglutinin, Eur. J. Biochem, vol. 260, pp. 166-175 (1999).
Sainsbury F & Lomonossoff GP. Extremely high-level and rapid transient protein production in plants without the use of viral replication, Plant Physiol 148, pp. 1212-1218 (2008).
Sainsbury F, et al. Expression of multiple proteins using full-length and deleted versions of cowpea mosaic virus RNA-2, Plant Biotechnol J 6, pp. 82-92 (2008).
Saint-Jore-Dupas C, et al. From planta to pharma with glycosylation in the toolbox, TRENDS in Biotechnol 25, pp. 317-323 (2007).
Selenko N, et al. CD20 antibody (C2B8)-induced apoptosis of lymphoma cells promotes phagocytosis by dendritic cells and cross-priming of CD8+ cytotoxic T cells, Leukemia 15, pp. 1619-1626 (2001).
Salzberg, et al. Genome analysis linking recent European and African influenza (H5N1) viruses, Emerg Infect Dis 13, pp. 713-718 (2007).
Santi L, et al. An efficient plant viral expression system generating orally immunogenic Norwalk virus-like particles, Vaccine 26, pp. 1846-1854 (2008).
Scheid OM, et al. Reversible inactivation of a transgene in Arabidopsis thaliana, Mol Gen Genet 228, pp. 104-112 (1991).
Schillberg S, et al. Apoplastic and cytosolic expression of full-size antibodies and antibody fragments in Nicotiana tabacum, Transgenic Res 8, pp. 255-263 (1999).
Schillberg S, et al. Molecular farming of recombinant antibodies in plants, Cell Mol Life Sci 60, pp. 433-445 (2003).
Schuler & Zielinski. Chapter 8: Transformation of Leaf Discs with Agrobacterium, in Methods in Plant Molecular Biology (14 pages) (1989).
Shoji Y, et al. Plant-expressed HA as a seasonal influenza vaccine candidate, Vaccine 26, pp. 2930-2934 (2008).
Shorrosh BS & Dixon RA. Molecular cloning of a putative plant endomembrane protein resembling vertebrate protein disulfide-isomerase and a phosphatidylinositol-specific phospholipase C, Proc Natl Acad Sci USA 88, pp. 10941-10945 (1991).
Shorrosh, B. et al. Sequence analysis and developmental expression of an alfalfa protein disulfide isomerase. Plant Molecular Biology, vol. 19, pp. 319-321 (1992).
Skehel & Wiley. Receptor binding and membrane fusion in virus entry: the influenza hemagglutinin, Ann Rev Biochem 69, pp. 531-569 (2000).
Smith ML, et al. Structural characterization of plant-derived hepatitis B surface antigen employed in oral immunization studies, Vaccine 21, pp. 4011-4021 (2003).
Spitsin, et al. Immunological assessment of plant-derived avian flu H5/HA1 variants, Vaccine, vol. 27, No. 9, pp. 1289-1292 (2009).
Squires B, et al. BioHealthBase: informatics support in the elucidation of influenza virus host—pathogen interactions and virulence, Nucl Acids Res 36, pp. D497-D503 (2008).
Sriraman, et al. Recombinant anti-hCG antibodies retained in the endoplasmic reticulum of transformed plants lack core-xylose and core-$\alpha$(1,3)-fucose residues, Plant Biotechnol J 2, pp. 279-287 (2004).
Staehelin LA. The plant ER: a dynamic organelle composed of a large number of discrete functional domains, Plant J 11, pp. 1151-1165 (1997).
Suzuki Y. Sialobiology of influenza: molecular mechanism of host range variation of influenza viruses, Biol Pharm Bull 28, pp. 399-408 (2005).
Szyperski T, et al. Structure comparison of human glioma pathogenesis-related protein GliPR and the plant pathogenesis-related protein P14a indicates a functional link between the human immune system and a plant defense system, Proc Natl Acad Sci 95, pp. 2262-2266 (1998).

(56) References Cited

OTHER PUBLICATIONS

Tacket CO, et al. Human immune responses to a novel Norwalk virus vaccine delivered in transgenic potatoes, J Infect Dis 182, pp. 302-305 (2000).
Toukach, et al. Sharing of worldwide distributed carbohydrate-related digital resources: online connection of the Bacterial Carbohydrate Structure DataBase and Glycosciences.de, Nucl Acids Res 35, pp. D280-D286 (2007).
Treanor, et al. Safety and immunogenicity of a baculovirus-expressed hemagglutinin influenza vaccine: a randomized controlled trial, JAMA 297, pp. 1577-1582 (2007).
Vaccaro L, et al. Plasticity of influenza haemagglutinin fusion peptides and their interaction with lipid bilayers, Biophys J 88, pp. 25-36 (2005).
van Ree R, et al. β(1,2)-xylose and α(1,3)-fucose residues have a strong contribution in IgE binding to plant glycoallergens, J Biol Chem 275, pp. 11451-11458 (2000).
Varsani, et al. Expression of Human papillomavirus type 16 major capsid protein in transgenic Nicotiana tabacum cv. Xanthi, Arch Viral 148, pp. 1771-1786 (2003).
Vezina, et al. Transient co-expression for fast and high-yield production of antibodies with human-like N-glycans in plants, Plant Biotechnol J 7, pp. 442-455 (2009).
Vigerust, et al. N-Linked Glycosylation Attenuates H3N2 Influenza Viruses, Journal of Virology, vol. 81, No. 16, pp. 8593-8600 (2007).
Voinnet O, et al. An enhanced transient expression system in plants based on suppression of gene silencing by the p19 protein of tomato bushy stunt virus, Plant J 33, pp. 949-956 (2003).
Wagner, et al. Interdependence of hemagglutinin glycosylation and neuraminidase as regulators of influenza virus growth: a study by reverse genetics, J Virol 74, pp. 6316-6323 (2000).
Wakefield, et al. RNA-binding properties of influenza A virus matrix protein M1, Nucl Acids Res 17, pp. 8569-8580 (1989).
Wang, et al. Expression and purification of an influenza hemagglutinin—one step closer to a recombinant protein-based influenza vaccine, Vaccine 24, pp. 2176-2185 (2006).
Wei, et al. Comparative efficacy of neutralizing antibodies elicited by recombinant hemagglutinin proteins from avian H5N1 influenza virus, J Virol 82, pp. 6200-6208 (2008).
Weldon, et al. Enhanced Immunogenicity of Stabilized Trimeric Soluble Influenza Hemagglutinin, PLOS One, vol. 5, No. 9, e12466, pp. 1-8 (2010).
Wilson IBH, et al. Core α1,3-fucose is a key part of the epitope recognized by antibodies reacting against plant N-linked oligosaccharides and is present in a wide variety of plant extracts, Glycobiol 8, pp. 651-661 (1998).
Wydro M, et al. Optimization of transient Agrobacterium-mediated gene expression system in leaves of Nicotania benthamiana, Acta Biochimica Polonica 53, pp. 289-298 (2006).
Preliminary Amendment dated Mar. 22, 2012 for U.S. Appl. No. 13/497,757, filed Sep. 21, 2010 (Vezina et al.) (4 pages).
Preliminary Amendment dated Mar. 22, 2012 for U.S. Appl. No. 13/497,767, filed Mar. 22, 2012 (D'Aoust et al.) (4 pages).
Preliminary Amendment dated Jan. 23, 2013 for U.S. Appl. No. 13/748,531, filed Jan. 23, 2013 (D'Aoust et al.) (3 pages).
Requirement for Restriction/Election dated Mar. 25, 2013 for U.S. Appl. No. 13/748,531, filed Jan. 23, 2013 (D'Aoust et al.) (9 pages).
Response to Requirement for Restriction/Election dated Apr. 25, 2013 for U.S. Appl. No. 13/748,531, filed Jan. 23, 2013 (D'Aoust et al.) (3 pages).
Non-Final Rejection dated Sep. 23, 2013 for U.S. Appl. No. 13/748,531, filed Jan. 23, 2013 (D'Aoust et al.) (10 pages).
Preliminary Amendment dated Jan. 13, 2010 for U.S. Appl. No. 12/669,033, filed Jun. 11, 2010 (D'Aoust et al.) (7 pages).
Requirement for Restriction/Election dated Aug. 13, 2012 for U.S. Appl. No. 12/669,033, filed Jun. 11, 2010 (D'Aoust et al.) (8 pages).
Response to Requirement for Restriction/Election dated Sep. 11, 2012 for U.S. Appl. No. 12/669,033, filed Jun. 11, 2010 (D'Aoust et al.) (5 pages).
Non-Final Rejection dated Oct. 4, 2012 for U.S. Appl. No. 12/669,033, filed Jun. 11, 2010 (D'Aoust et al.) (10 pages).
Response to Non-Final Rejection dated Nov. 2, 2012 for U.S. Appl. No. 12/669,033, filed Jun. 11, 2010 (D'Aoust et al.) (2 pages).
Miscellaneous Communication dated Dec. 5, 2012 for U.S. Appl. No. 12/669,033, filed Jun. 11, 2010 (D'Aoust et al.) (2 pages).
Notice of Abandonment dated Jul. 10, 2013 for U.S. Appl. No. 12/669,033, filed Jun. 11, 2010 (D'Aoust et al.) (2 pages).
Notice of Abandonment dated Jul. 25, 2013 for U.S. Appl. No. 12/863,772, filed Jul. 20, 2010 (D'Aoust et al.) (2 pages).
Non-Final Rejection dated Dec. 14, 2012 for U.S. Appl. No. 12/863,772, filed Jul. 20, 2010 (D'Aoust et al.) (8 pages).
Response to Requirement for Restriction/Election dated Oct. 29, 2012 for U.S. Appl. No. 12/863,772, filed Jul. 20, 2010 (D'Aoust et al.) (3 pages).
Requirement for Restriction/Election dated Sep. 27, 2012 for U.S. Appl. No. 12/863,772, filed Jul. 20, 2010 (D'Aoust et al.) (9 pages).
Preliminary Amendment dated Jul. 20, 2010 for U.S. Appl. No. 12/863,772, filed Jul. 20, 2010 (D'Aoust et al.) (7 pages).
1st Preliminary Amendment dated Jan. 4, 2013 for U.S. Appl. No. 13/734,886, filed Jan. 4, 2013 (D'Aoust et al.) (3 pages).
2nd Preliminary Amendment dated Mar. 22, 2013 for U.S. Appl. No. 13/734,886, filed Jan. 4, 2013 (D'Aoust et al.) (13 pages).
3rd Preliminary Amendment dated Aug. 22, 2013 for U.S. Appl. No. 13/734,886, filed Jan. 4, 2013 (D'Aoust et al.) (5 pages).
Non-Final Rejection dated Nov. 25, 2013 for U.S. Appl. No. 13/734,886, filed Jan. 4, 2013 (D'Aoust et al.) (12 pages).
Decision regarding Petition dated Nov. 26, 2013 for U.S. Appl. No. 13/380,346, filed Apr. 17, 2012 (Couture et al.) (3 pages).
Amendment in Response to Decision regarding Petition with renewed Petition dated Nov. 16, 2013 for U.S. Appl. No. 13/380,346, filed Apr. 17, 2012 (Couture et al.) (13 pages).
Non-Final Office Action dated Nov. 5, 2013 for U.S. Appl. No. 13/380,346, filed Apr. 17, 2012 (Couture et al.) (12 pages).
Decision regarding Petition dated Oct. 10, 2013 for U.S. Appl. No. 13/380,346, filed Apr. 17, 2012 (Couture et al.) (3 pages).
Preliminary Amendment dated Aug. 20, 2013 for U.S. Appl. No. 13/380,346, filed Apr. 17, 2012 (Couture et al.) (26 pages).
Request for Participation in PPH Program dated Aug. 20, 2013 for U.S. Appl. No. 13/380,346, filed Apr. 17, 2012 (Couture et al.) (2 pages).
Preliminary Amendment dated Mar. 20, 2012 for U.S. Appl. No. 13/380,346, filed Apr. 17, 2012 (Couture et al.) (4 pages).
Office Action dated May 21, 2013 by the Australian Intellectual Property Office for AU patent application No. 2008278222 filed on Jul. 11, 2008 (Medicago, Inc. // D'Aoust et al.) (3 pages).
Office Action dated Mar. 1, 2013 by the Canadian Intellectual Property Office for CA patent application No. 2,707,235 filed on Jan. 12, 2009 (Medicago, Inc. // D'Aoust et al.) (2 pages).
Office Action dated Sep. 28, 2012 by the Canadian Intellectual Property Office for CA patent application No. 2,707,235 filed on Jan. 12, 2009 (Medicago, Inc. // D'Aoust et al.) (2 pages).
Office Action dated Jun. 7, 2012 by the Canadian Intellectual Property Office for CA patent application No. 2,707,235 filed on Jan. 12, 2009 (Medicago, Inc. // D'Aoust et al.) (3 pages).
Office Action dated Jun. 1, 2011 by the Canadian Intellectual Property Office for CA patent application No. 2,707,235 filed on Jan. 12, 2009 (Medicago, Inc. // D'Aoust et al.) (5 pages).
Office Action dated Mar. 1, 2013 by the Canadian Intellectual Property Office for CA patent application No. 2,693,956 filed on Jul. 11, 2008 (Medicago, Inc. // D'Aoust et al.) (2 pages).
Office Action dated Oct. 16, 2012 by the Canadian Intellectual Property Office for CA patent application No. 2,693,956 filed on Jul. 11, 2008 (Medicago, Inc. // D'Aoust et al.) (2 pages).
Office Action dated Jan. 20, 2012 by the Canadian Intellectual Property Office for CA patent application No. 2,693,956 filed on Jul. 11, 2008 (Medicago, Inc. // D'Aoust et al.) (2 pages).
Office Action dated Sep. 22, 2011 by the Canadian Intellectual Property Office for CA patent application No. 2,693,956 filed on Jul. 11, 2008 (Medicago, Inc. // D'Aoust et al.) (3 pages).
Office Action dated Jan. 26, 2011 by the Canadian Intellectual Property Office for CA patent application No. 2,693,956 filed on Jul. 11, 2008 (Medicago, Inc. // D'Aoust et al.) (3 pages).

(56) References Cited

OTHER PUBLICATIONS

Office Action dated Nov. 27, 2012 by the State Intellectual Property Office of People's Republic of China for CN patent application No. 200980109781.5 filed on Jan. 12, 2009 (Medicago, Inc. // D'Aoust et al.) (5 pages).
Office Action dated Jan. 21, 2012 by the State Intellectual Property Office of People's Republic of China for CN patent application No. 200980109781.5 filed on Jan. 12, 2009 (Medicago, Inc. // D'Aoust et al.) (9 pages).
Office Action dated Feb. 21, 2013 by the State Intellectual Property Office of People's Republic of China for CN patent application No. 200880107072.9 filed on Jan. 12, 2009 (Medicago, Inc. // D'Aoust et al.) (6 pages).
Office Action dated Jul. 24, 2012 by the State Intellectual Property Office of People's Republic of China for CN patent application No. 200880107072.9 filed on Jan. 12, 2009 (Medicago, Inc. // D'Aoust et al.) (10 pages).
Office Action dated Sep. 27, 2011 by the State Intellectual Property Office of People's Republic of China for CN patent application No. 200880107072.9 filed on Jan. 12, 2009 (Medicago, Inc. // D'Aoust et al.) (8 pages).
Office Action dated May 30, 2013 by the State Intellectual Property Office of People's Republic of China for CN patent application No. 200980134868.8 filed on Jul. 2, 2009 (Medicago, Inc. // D'Aoust et al.) (5 pages).
Office Action dated Jul. 16, 2012 by the State Intellectual Property Office of People's Republic of China for CN patent application No. 200980134868.8 filed on Jul. 2, 2009 (Medicago, Inc. // D'Aoust et al.) (6 pages).
Office Action dated Mar. 1, 2013 by the State Intellectual Property Office of People's Republic of China for CN patent application No. 201080042333.0 (Medicago, Inc. // D'Aoust et al.) (12 pages).
Office Action dated Dec. 13, 2011 by the Eurasian Patent Office for EA patent application No. 201000195/28 (Medicago, Inc. // D'Aoust et al.) (4 Pages).
Office Action dated Jun. 13, 2012 by the Eurasian Patent Office for application No. 201000195/28 (Medicago, Inc. // D'Aoust et al) (1 Page).
Office Action dated Aug. 28, 2012 by the Eurasian Patent Office for application No. 201001198 filed Feb. 7, 2009 (Medicago, Inc. // D'Aoust et al) (5 Pages).
Office Action dated Apr. 24, 2013 by the Eurasian Patent Office for application No. 201001198 filed Feb. 7, 2009 (Medicago, Inc. // D'Aoust et al) (3 Pages).
Office Action dated Nov. 18, 2011 by the Egyptian Patent Office for EG patent application No. PCT 1222/2010 filed on Jan. 12, 2009 (Medicago, Inc. // D'Aoust et al.) (9 pages).
Office Action dated Oct. 26, 2012 by the European Patent Office for EP patent application No. 2008783201.0 filed on Jul. 11, 2008 (Medicago, Inc. // D'Aoust et al.) (3 pages).
Decision to Grant dated May 31, 2013 by the European Patent Office for EP patent application No. 2008783201.0 filed on Jul. 11, 2008 (Medicago, Inc. // D'Aoust et al.) (2 pages).
Extended European Search Report dated Sep. 13, 2010 by the European Patent Office for EP patent application No. 2008783201.0 filed on Jul. 11, 2008 (Medicago, Inc. // D'Aoust et al.) (9 pages).
European Search Report dated May 26, 2011 by the European Patent Office for EP patent application No. 2008783201.0 filed on Jul. 11, 2008 (Medicago, Inc. // D'Aoust et al.) (4 pages).
Extended European Search Report dated Mar. 7, 2011 by the European Patent Office for EP patent application No. 2009700061.6 filed on Jan. 12, 2009 (Medicago, Inc. // D'Aoust et al.) (11 pages).
Decision to Grant dated Aug. 17, 2012 by the European Patent Office for EP patent application No. 2009700061.6 filed on Jan. 12, 2009 (Medicago, Inc. // D'Aoust et al.) (1 page).
Extended European Search Report dated Aug. 9, 2011 by the European Patent Office for EP patent application No. 2009793741.1 filed on Jul. 2, 2009 (Medicago, Inc. // D'Aoust et al.) (9 pages).
Extended European Search Report dated Jan. 28, 2013 by the European Patent Office for EP patent application No. 10818190.0 filed on Sep. 21, 2010 (Medicago, Inc. // Vezina et al.) (6 pages).
Extended European Search Report dated Jan. 3, 2013 by the European Patent Office for EP patent application No. 10818191.8 filed on Sep. 21, 2010 (Medicago, Inc. // Vezina et al.) (5 pages).
Extended European Search Report dated Feb. 15, 2013 by the European Patent Office for EP patent application No. 12181077.4 filed on Jul. 2, 2009 (Medicago, Inc. // D'Aoust et al.) (8 pages).
Office Action dated Sep. 18, 2012 by the Indonesian Patent Office for ID application No. ID W-0020102481 filed Jul. 11, 2008 (Medicago, Inc. // D'Aoust et al.) (2 Pages).
Office Action dated Oct. 25, 2012 by the Registrar of Patents of Israel for IL patent application No. 210215 filed on Jul. 2, 2009 (Medicago, Inc. // D'Aoust et al.) (2 pages).
Office Action dated May 9, 2012 by the Registrar of Patents of Israel for IL patent application 206967 filed on Jan. 12, 2009 (Medicago, Inc. // D'Aoust et al.) (2 pages).
Office Action dated May 8, 2012 by the Registrar of Patents of Israel for IL patent application 203018 filed on Jan. 12, 2009 (Medicago, Inc. // D'Aoust et al.) (2 pages).
Office Action dated Mar. 6, 2013 by the Mexican Patent Office for MX patent application No. MX/a/2010/000525 filed on Jul. 11, 2008 (Medicago, Inc. // D'Aoust et al) (4 pages).
Office Action dated Mar. 6, 2013 by the Mexican Patent Office for MX patent application No. MX/a/2010/007962 filed on Jan. 12, 2009 (Medicago, Inc. // D'Aoust et al) (4 pages).
Office Action dated Mar. 6, 2013 by the Mexican Patent Office for MX application No. MX/a/2010/000459 filed on Jul. 22, 2009 (Medicago, Inc. // D'Aoust et al) (3 pages).
Examination Report dated Nov. 14, 2012 by the Intellectual Property Office of New Zealand for NZ patent application 598481 (2 pages).
Examination Report dated Nov. 15, 2012 by the Intellectual Property Office of New Zealand for NZ patent application 598508 (2 pages).
Examination Report dated Apr. 15, 2011 by the Intellectual Property Office of New Zealand for NZ patent application 590144 filed on Jul. 2, 2009 (Medicago, Inc. // D'Aoust et al.) (3 pages).
Examination Report dated Mar. 21, 2011 by the Intellectual Property Office of New Zealand for NZ patent application 587108 filed on Jan. 12, 2009 (Medicago, Inc. // D'Aoust et al.) (2 pages).
Examination Report dated Jun. 27, 2012 by the Intellectual Property Office of New Zealand for NZ patent application 587108 filed on Jan. 12, 2009 (Medicago, Inc. // D'Aoust et al.) (2 pages).
Examination Report dated Jan. 28, 2013 by the Intellectual Property Office of New Zealand for NZ patent application 587108 filed on Jan. 12, 2009 (Medicago, Inc. // D'Aoust et al.) (2 pages).
Examination Report dated Nov. 8, 2010 by the Intellectual Property Office of New Zealand for NZ patent application 582360 filed on Jul. 11, 2008 (Medicago, Inc. // D'Aoust et al.) (9 pages).
Office Action dated Apr. 5, 2013 by the Russian Patent Office for RU patent application RU 2011105073/10 (2 pages).
Singapore Written Opinion dated May 2, 2011 by the Danish Patent Office for SG patent application 201000090-9 filed on Jul. 11, 2008 (Medicago, Inc. // D'Aoust et al.) (16 pages).
Certificate of Grant of Patent dated Apr. 30, 2012 by the Intellectual Property Office of Singapore for application 201000090-9 filed on Jul. 11, 2008 (Medicago, Inc. // D'Aoust et al.) (2 pages).
Written Opinion dated Apr. 18, 2012 by the Intellectual Property Office of Singapore for application 201009568-5 filed on Jul. 11, 2008 (Medicago, Inc. // D'Aoust et al.) (20 pages).
Non-Final Rejection dated Aug. 28, 2014 by the U.S. Patent and Trademark Office for U.S. Appl. No. 13/497,757 (Applicant Medicago, Inc. // 1st Named Inventor—L.P. Vezina) (60 pages).
Non-Final Rejection dated Sep. 4, 2014 by the U.S. Patent and Trademark Office for U.S. Appl. No. 13/497,767 (Applicant Medicago, Inc. // 1st Named Inventor—L.P. Vezina) (95 pages).
Anonymous: Protoplast preparation (from plant tissue), Dec. 1, 2006 (URL: http://www.ivaan.com/protocols/128.html).
Biemelt, Sophia, et al. Production of Human Papillomavirus Type 16 Virus-Like particles in Transgenic Plants. J. of Virology, Sep. 2003, pp. 9211-9220.

(56) References Cited

OTHER PUBLICATIONS

Wickramasinghe, S.R., et al. Tangential Flow Microfiltration and Ultrafiltration for HumanInfluenza A Virus Concentration and Purification. Biotechnology and Bioengineering, vol. 92:2, Oct. 20, 2005, pp. 199-208.
Yigzaw, Y., et al. Exploitation of the Adsorptive Properties of Depth Filters for Host Cell Protein Removal during Monoclonal Antibody Purification. Biotechnol. Prog. 2006, vol. 22, pp. 288-296.
Notice of Acceptance dated Dec. 17, 2014 for Australian patent application AU 2010300033 (Applicant Medicago, Inc. // 1st Named Inventor—L.P. Vezina) (3 pages).
Exam Report dated Dec. 24, 2014 for Australian patent application AU 2010300034 (Applicant Medicago, Inc. // 1st Named Inventor—L.P. Vezina) (4 pages).
Decision on Rejection dated May 28, 2014 by the State Intellectual Property Office of People's Republic of China for patent application CN 201080042333.0 (Medicago, Inc.) (Translation by for Foreign Associate—5 pages).
Office Action dated Nov. 15, 2014 by the State Intellectual Property Office of People's Republic of China for patent application CN 201080042336.4 (Medicago, Inc.) (Translation by Foreign Associate—11 pages).
Office Action dated Aug. 13, 2014 by the State Intellectual Property Office of People's Republic of China for patent application CN 201280014186.5 (Medicago, Inc.) (Translation by Foreign Associate—10 pages).
Article 94(3) Communication dated Aug. 18, 2014 by the European Patent Office for EP 10818191.8 (Medicago, Inc. // Vezina et al.) (5 pages).
Article 94(3) Communication dated Oct. 6, 2014 by the European Patent Office for EP 10818190.0 (Medicago, Inc. // Vezina et al.) (5 pages).
Supplemental Search Report dated Sep. 9, 2014 by the European Patent Office for EP 12759964.5 (Medicago, Inc. // Vezina et al.) (7 pages).
Office Action dated Sep. 28, 2014 by the State of Isreal, Registrar of Patents for Israeli patent application IL 218393 (Translation by Foreign Associate—2 pages).
Office Action dated Oct. 21, 2014 re by the State of Isreal, Registrar of Patents for Israeli patent application IL 218422 (Translation by Foreign Associate—2 pages).
Second Office Action dated Aug. 27, 2014 for MX patent application MX/a/2012/003372 (Applicant—Medicago, Inc. // 1st Named Inventor—L.P. Vezina) (Translated Summary by Foreign Associate—3 pages).
Office Action dated Jul. 8, 2014 for MX patent application MX/a/2012/003373 (Applicant—Medicago, Inc. // 1st Named Inventor—L.P. Vezina).
Office Action dated Feb. 10, 2015 for MX patent application MX/a/2012/003373 (Applicant—Medicago, Inc. // 1st Named Inventor—L.P. Vezina) (Translated Summary by Foreign AssociateZ—4 pages).
Office Action dated Sep. 29, 2014 for Russian patent application RU 2012115661 (Applicant—Medicago, Inc. // 1st Named Inventor—L.P. Vezina) (Translated by Foreign Associate—8 pages).
Office Action dated Jun. 19, 2014 for Russian patent application RU 2012115996 (Applicant—Medicago, Inc. // 1st Named Inventor—L.P. Vezina) (Translated by Foreign Associate—1 page).
Office Action dated Nov. 12, 2014 for Russian patent application RU 2012115996 (Applicant—Medicago, Inc. // 1st Named Inventor—L.P. Vezina) (Translated by Foreign Associate—3 pages).
Abdel-Salam, et al., (2004) "Purification, serology and molecular detection of Egyptian isolates of banana bunchy top babuvirus and faba bean necrotic yellows nanovirus", Arab J. Biotech, 7(1), pp. 141-155.
Takahashi, et al., (2007) "A high-throughput screen of cell-death-inducing factors in Nicotiana benthamiana identifies a novel MAPKK that mediates INF1-induced cell death signaling and non-host resistance to Pseudomonas cichorii", The Plant Journal, 49, pp. 1030-1040.
Webby, et al., (1992) "Purification of the NY-RMV and NY-SGV Isolates of Barley Yellow Dwarf Virus and the Production and Properties of their Antibodies", Plant Disease, pp. 1125-1132.
Decision on Rejection dated May 28, 2015 by the State Intellectual Property Office of the People's Republic of China for application CN 201080042336.4 (Applicant—Medicago, Inc., (7 pages—English Translation).
Office Action dated Mar. 13, 2015 by the State Intellectual Property Office of the People's Republic of China for application CN 201280014186.5 (Applicant—Medicago, Inc., (14 pages—Chiense Language and English Translation).
Communication Pursuant to Article 94(3) EPC dated Sep. 25, 2015 by the European Patent Office for EP 10818190.0 which was filed Sep. 21, 2010 and published as WO 2011/035422 on Mar. 31, 2011 (1st Named Inventor—Vezina; Applicant—Medicago, Inc.) (6 pages).
Communication Pursuant to Article 94(3) EPC dated Oct. 7, 2015 by the European Patent Office for EP 12759964.5, (Applicant—Medicago, Inc.) (6 pages).
Office Action dated Jun. 24, 2015 by the Federal Service for Intellectual Property of the Russian Federation for application RU 2012115661 (2 pages—English Translation).
Notice of Allowance dated May 5, 2015 by the Federal Service for Intellectual Property of the Russian Federation for application RU 012115996 (9 pages—Translation).
Final Office Action issued by the USPTO dated Jun. 24, 2015 for U.S. Appl. No. 13/497,767, filed Mar. 22, 2012 and published as US-2013-0067807-A1 on Mar. 22, 2013 (1st Named Inventor—Vezina; Applicant—Medicago, Inc.) (9 pages).
Final Office Action issued by the USPTO dated Jun. 25, 2015 for U.S. Appl. No. 13/497,757, filed Mar. 22, 2012 and published as US-2012-0178149-A1 on Mar. 22, 2013 (1st Named Inventor—Vezina; Applicant—Medicago, Inc.) (22 pages).
Fourth Office Action dated Aug. 9, 2016 by the State Intellectual Property Office of the People's Republic of China for CN Application No. 201280014186.5, which was filed on Mar. 23, 2012 and published as CN 103502261-A on Jan. 8, 2014 (Applicant—Medicago, Inc.) (Original—5 pages // 10 pages).
Communication pursuant to Article 94(3) EPC dated May 23, 2016 by the European Patent Office for EP Application No. 12759964.5, which was filed on Mar. 23, 2012 and published as EP 2688903 on Jan. 29, 2014 (Applicant—Medicago, Inc.) (5 pages).
Rejection Decision dated Jul. 11, 2016 by the Taiwan Patent Office for TW Application No. 101109798, which was filed on Mar. 22, 2012 (Applicant—Medicago, Inc.) (5 pages).
Examination Report was issued on by the Korean Patent Office for KR Application No. UAE/P/0287/2012, which was dated Mar. 21, 2012 and (Applicant—Medicago, Inc.) (6 pages).
Office Action dated Oct. 4, 2016 by the Canadian Patent Office for CA Application No. 2,772,964, which was filed on Sep. 21, 2010 and published as 2,772,964 on Mar. 31, 2011(Applicant—Medicago, Inc.) (4 pages).
Notice of Re-Examination dated Sep. 20, 2016 by the State Intellectual Property Office of the People's Republic of China for CN Application No. 201080042336.4, which was filed on Sep. 21, 2010 and published as CN 102549008-A on Jul. 4, 2012 (Applicant—Medicago Inc.) (11 pages).
Communication pursuant to Article 94(3) EPC dated Jul. 26, 2016 by the European Patent Office for EP Application No. 10818191.8, which was filed on Sep. 21, 2010 and published as EP 2480560 A1 on Aug. 1, 2012 (Applicant—Medicago, Inc.) (4 pages).
Office Action dated Jun. 16, 2016 by the Intellectual Property Office of the Philippines Bureau of Patents for PH Application No. 1/2012/500565, which was filed on Mar. 20, 2012(Applicant—Medicago Inc.) (3 pages).
Examination Report dated Nov. 10, 2016 by the Intellectual Property Office of Singapore for SG Application No. 201201471-8, which was filed on Sep. 21, 2010 (Applicant—Medicago Inc.) (11 pages).
Written Opinion dated May 17, 2016 by the Intellectual Property Office of Singapore for SG Application No. 201201471-8, which was filed on Sep. 21, 2010 (Applicant—Medicago Inc.) (11 pages).

(56) References Cited

OTHER PUBLICATIONS

Final Rejection dated Nov. 25, 2016 by the U.S. Patent and Trademark Office for U.S. Appl. No. 13/497,767, filed Mar. 22, 2012 and published as US 2013-0067807 A1 on Mar. 21, 2013 (Inventor—Louis-Philippe Vezina et al) (12 pages).
Examination Report dated Oct. 28, 2016 by the Korean Intellectual Property Office for KR Application No. UAE/P/0286/2012 which was filed on Mar. 21, 2012 (Applicant—Medicago) (9 pages).
Notice of Reexamination dated May 26, 2016 by the State Intellectual Property Office of the People's Republic of China for CN Application No. 201080042333.0, which was filed on Sep. 31, 010 and published as 102549148A on Jul. 4, 2012 (Applicant—Medicago Inc.) (4 pages).
Decision of Reexamination dated Dec. 21, 2016 by the State Intellectual Property Office of the People's Republic of China for CN Application No. 201080042333.0, which was filed on Sep. 31, 010 and published as 102549148A on Jul. 4, 2012 (Applicant—Medicago Inc.) (1 page).
Communication pursuant to Article 94(3) EPC dated Jul. 27, 2016 by the European Patent Office for EP Application No. 10818190.0, which was filed on Sep. 21, 2010 (Applicant—Medicago Inc.) (5 pages).
Notice for Grounds of Refusal dated Sep. 29, 2016 by the Korean Intellectual Property Office for KR Application No. 10-2012-7009357, which was filed on Apr. 12, 2012 (Applicant—Medicago Inc.) (8 pages).
Substantive Examination Report dated Jun. 28, 2016 by the Intellectual Property Office of the Philippines Bureau of Patents for PH Application No. 1/2012/500566, which was filed on Mar. 20, 2012(Applicant—Medicago Inc.) (4 pages).
Final Rejection dated Dec. 15, 2016 by the U.S. Patent and Trademark Office for U.S. Appl. No. 13/497,757, filed Mar. 22, 2012 and published as US 2013-0067807 A1 on Mar. 21, 2013 (Inventor—Louis-Philippe Vezina et al) (15 pages).
Notice of Defects in Patent Application dated Jul. 27, 2016 by the State of Israel Ministry of Justice Registrar of Patents for IL Application No. 218393 (Applicant—Medicago Inc.) (4 pages).
Notice of Defects in Patent Application dated May 23, 2016 by the State of Israel Ministry of Justice Registrar of Patents for IL Application No. 218422 (Applicant—Medicago Inc.) (2 pages).
D'Aoust, Marc-André, et al. Influenza virus-like particles produced by transient expression in Nicotiana benthamiana induce a protective immune response against a lethal viral challenge in mice. Plant Biotechnology Journal, (2008), 6.9: 930-940.
Diaz-Vivancos P (2006) The apoplastic antioxidant system in Prunus: response to long-term plum pox virus infection. J Exp. Bot. 57:3813-3824.
Fischer, R. Affinity-purification of a TMV-specific recombinant full-size antibody from a transgenic tobacco suspension culture. Journal of immunological methods, (1999), 226.1: 1-10.
Low, D. et al., 'Future of antibody purification', J. Chromatography B, (2007), vol. 848, No. 1, pp. 48-63.

Santi et al., An efficient plant viral expression system generating orally immunogenic Norwalk virus-like particles, Vaccine.(2008) 26(15):1846-54.
Twyman et al., "Molecular farming of recombinant antibodies in plants", Cell. Mol. Life Sci., 60, pp. 433-445, (2003).
Schillberg, S., et al. Apoplastic and cytosolic expression of full-size antibodies and antibody fragments in Nicotiana tabacum. Transgenic Research, (1999), 8.4: 255-263.
Takahashi et al., "A high-throughput screen of cell-death-inducing factors in Nicotiana benthamiana identifies a novel MAPKK that mediates INF1-induced cell death signaling and non-host resistance to Pseudomonas cichorii" The Plant Journal, 49, pp. 1030-1040, (2007).
Examination Report dated Apr. 15, 2016 by the Australian Patent Office for U.S. Appl. No. 14/006,552, filed Sep. 20, 2013, and published as US 2014-0024104 A1 on Jan. 23, 2014. (Inventor—Manon Couture; Applicant—Medicago Inc.) (4 pages).
Office Action dated Nov. 26. 2015 by the State Intellectual Property Office of People's Republic of China for Application No. 201280014186.5 (Applicant—Medicago Inc.) (11 Pages).
Office Action dated Feb. 9, 2016 by the Japaense Patent Office for Application No. 2014-500218 (Applicant—Medicago Inc.) (3 Pages).
Office Action dated Dec. 23, 2015 by the Taiwan Patent Office for Application No. 101109798 (Applicant—Medicago Inc.) (4 Pages).
Certificate of Grant dated Nov. 12, 2015 Re: AU2010300034 (Inventor: Vezina, Louis-Philippe et al) (1 Page).
Office Action dated Nov. 17, 2015 by the European Patent Office for Application No. 10818191.8 (Applicant—Medicago Inc.) (6 Pages).
Office Action dated Dec. 3, 2015 by the Indonesian Patent Office for Application No. W-00201201507 (Applicant—Medicago Inc.) (1 Page).
Office Action dated Jan. 12, 2016 by the U.S. Patent and Trademark Office for U.S. Appl.No. 13/497,767, filed Mar. 22, 2012, and published as US 2013-0067807 A1 onMar. 21, 2013. (Inventor—Louis-Philippe Vezina, et al) (16 pages).
Substantive Examination Adverse Report dated Mar. 31, 2016 by the Intellectual Property Corporation of Malaysia for Application No. PI2012001251, (Applicant—Medicago Inc.) (3 pages).
Office Action dated Feb. 22, 2016 by the U.S. Patent and Trademark Office for U.S. Appl. No. 13/497,757, filed Mar. 22, 2012, and published as US-2012-0178149-A1 on Jul. 12, 2012. (Inventor—Louis-Philippe Vezina, et al) (17 pages).
Power, J.B., et al, "A Simple Method for the Isolation of Very Large Numbers of Leaf Protoplasts by Using Mixtures of Cellulase and Pectinase" Biochem J., 111(5), 1969, 33P.
Waterhouse, F.M., et al Purification of Particles of Subterranean Clover Red Leaf Virus Using an Industrial-Grade Cellulase. Journal of Virological Methods 8 (1984) pp. 321-329.
Takebe, I., et al, "Isolation of tobacco mesophyll cells in intact and active state" Plant and Cell Physiol., 9, (1968) pp. 115-124.

* cited by examiner

Figure 2A

TTAATTAAGAATTCGAGCTCCACCGCGGAAACCTCCTCGGATTCCATTGCCCAGCTATCTGTCACTTTA
TTGAGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATATCTCCACTGACGTAAGGGATG
ACGCACAATCCCACTATCCTTCGCAAGACCCTTCCTCTATATAAGGAAGTTCATTTCATTTGGAGAGGT
ATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAACGTTTTCTTTCACTGAAGCGAAATCAAAGATCTCTTTGTGGACACGTA
GTGCGGCGCCATTAAATAACGTGTACTTGTCCTATTCTTGTCGGTGTGGTCTTGGGAAAAGAAAGCTTG
CTGGAGGCTGCTGTTCAGCCCCATACATTACTTGTTACGATTCTGCTGACTTTCGGCGGGTGCAATATC
TCTACTTCTGCTTGACGAGGTATTGTTGCCTGTACTTCTTTCTTCTTCTTGCTGATTGGTTCTATAA
GAAATCTAGTATTTTCTTTGAAACAGAGTTTTCCCGTGGTTTTCGAACTTGGAGAAAGATTGTTAAGCT
TCTGTATATTCTGCCCAAATTTGTCGGGCCCATGGAGAAAATAGTGCTTCTTCTTGCAATAGTCAGTCT
TGTTAAAAGTGATCAGATTTGCATTGGTTACCATGCAAACAATTCAACAGAGCAGGTTGACACAATCA
TGGAAAAGAACGTTACTGTTACACATGCCCAAGACATACTGGAAAAGACACACAACGGGAAGCTCTGC
GATCTAGATGGAGTGAAGCCTCTAATTTTAAGAGATTGTAGTGTAGCTGGATGGCTCCTCGGGAACCC
AATGTGTGACGAATTCATCAATGTACCGGAATGGTCTTACATAGTGGAGAAGGCCAATCAACCAATG
ACCTCTGTTACCCAGGGAGTTTCAACGACTATGAAGAACTGAAACACCTATTGAGCAGAATAAACCAT
TTTGAGAAAATTCAAATCATCCCCAAAAGTTCTTGGTCCGATCATGAAGCCTCATCAGGAGTTAGCTCA
GCATGTCCATACCTGGGAAGTCCCTCCTTTTTAGAAATGTGGTATGGCTTATCAAAAAGAACAGTACA
TACCCAACAATAAAGAAAAGCTACAATAATACCAACCAAGAGGATCTTTTGGTACTGTGGGAATTCA
CCATCCTAATGATGCGGCAGAGCAGACAAGGCTATATCAAAACCCAACCACCTATATTTCCATTGGGA
CATCAACACTAAACCAGAGATTGGTACCAAAAATAGCTACTAGATCCAAAGTAAACGGGCAAAGTGGA
AGGATGGAGTTCTTCTGGACAATTTTAAAACCTAATGATGCAATCAACTTCGAGAGTAATGGAAATTTC
ATTGCTCCAGAATATGCATACAAAATTGTCAAGAAAGGGGACTCAGCAATTATGAAAAGTGAATTGGA
ATATGGTAACTGCAACACCAAGTGTCAAACTCCAATGGGGGCGATAAACTCTAGTATGCCATTCCACA
ACATACACCCTCTCACCATCGGGGAATGCCCCAAATATGTGAAATCAAACAGATTAGTCCTTGCAACA
GGGCTCAGAAATAGCCCTCAAAGAGAGAGCAGAAGAAAAAAGAGAGGACTATTTGGAGCTATAGCAG
GTTTTATAGAGGGAGGATGGCAGGGAATGGTAGATGGTTGGTATGGGTACCACCATAGCAATGAGCAG
GGGAGTGGGTACGCTGCAGACAAAGAATCCACTCAAAAGGCAATAGATGGAGTCACCAATAAGGTCA
ACTCAATCATTGACAAAATGAACACTCAGTTTGAGGCCGTTGGAAGGGAATTTAATAACTTAGAAAGG
AGAATAGAGAATTTAAACAAGAAGATGGAAGACGGGTTTCTAGATGTCTGGACTTATAATGCCGAACT
TCTGGTTCTCATGGAAAATGAGAGAACTCTAGACTTTCATGACTCAAATGTTAAGAACCTCTACGACAA
GGTCCGACTACAGCTTAGGGATAATGCAAAGGAGCTGGGTAACGGTTGTTTCGAGTTCTATCACAAAT
GTGATAATGAATGTATGGAAAGTATAAGAAACGGAACGTACAACTATCCGCAGTATTCAGAAGAAGCA
AGATTAAAAAGAGAGGAAATAAGTGGGGTAAAATTGGAATCAATAGGAACTTACCAAATACTGTCAAT
TTATTCAACAGTGGCGAGTTCCCTAGCACTGGCAATCATGATGGCTGGTCTATCTTTATGGATGTGCTC
CAATGGATCGTTACAATGCAGAATTTGCATTTAAAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATTTAATTT
CTTTGTGAGCTCCTGTTTAGCAGGTCGTCCCTTCAGCAAGGACACAAAAAGATTTTAATTTTATTAAAA
AAAAAAAAAAAAAGACCGGGAATTCGATATCAAGCTTATCGACCTGCAGATCGTTCAAACATTTGGC
AATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATCG
CGCGCGGTGTCATCTATGTTACTAGATTCTAGAGTCTCAAGCTTGGCGCGCC

Figure 2B

MEKIVLLLAIVSLVKSDQICIGYHANNSTEQVDTIMEKNVTVTHAQDILEKTHNGKLCDLDGVKPLILRDCS
VAGWLLGNPMCDEFINVPEWSYIVEKANPTNDLCYPGSFNDYEELKHLLSRINHFEKIQIIPKSSWSDHEASS
GVSSACPYLGSPSFFRNVVWLIKKNSTYPTIKKSYNNTNQEDLLVLWGIHHPNDAAEQTRLYQNPTTYISIG
TSTLNQRLVPKIATRSKVNGQSGRMEFFWTILKPNDAINFESNGNFIAPEYAYKIVKKGDSAIMKSELEYGN
CNTKCQTPMGAINSSMPFHNIHPLTIGECPKYVKSNRLVLATGLRNSPQRESRRKKRGLFGAIAGFIEGGWQ
GMVDGWYGYHHSNEQGSGYAADKESTQKAIDGVTNKVNSIIDKMNTQFEAVGREFNNLERRIENLNKKM
EDGFLDVWTYNAELLVLMENERTLDFHDSNVKNLYDKVRLQLRDNAKELGNGCFEFYHKCDNECMESIR
NGTYNYPQYSEEARLKREEISGVKLESIGTYQILSIYSTVASSLALAIMMAGLSLWMCSNGSLQCRICI

Figure 5

```
AGAGGTACCCCGGGCTGGTATATTTATATGTTGTCAAATAACTCAAAAACCATAAAAGTTTAAGTTAGC
AAGTGTGTACATTTTTACTTGAACAAAAATATTCACCTACTACTGTTATAAATCATTATTAAACATTAG
AGTAAAGAAATATGGATGATAAGAACAAGAGTAGTGATATTTTGACAACAATTTTGTTGCAACATTTG
AGAAAATTTTGTTGTTCTCTCTTTTCATTGGTCAAAAACAATAGAGAGAGAAAAAGGAAGAGGGAGAA
TAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCAT
TAGAGAGATGTACCATTAGAGAATTTTTGGCAAGTCATTAAAAAGAAAGAATAAATTATTTTTAAAAT
TAAAAGTTGAGTCATTTGATTAAACATGTGATTATTTAATGAATTGATGAAAGAGTTGGATTAAAGTTG
TATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGA
TAACATCCAATCCAACCAATCACAACAATCCTGATGAGATAACCCACTTTAAGCCCACGCATCTGTGGC
ACATCTACATTATCTAAATCACACATTCTTCCACACATCTGAGCCACACAAAAACCAATCCACATCTTT
ATCACCCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTCTTGCAATA
GTCAGTCTTGTTAAAAGTGATCAGATTTGCATTGGTTACCATGCAAACAATTCAACAGAGCAGGTTGAC
ACAATCATGGAAAAGAACGTTACTGTTACACATGCCCAAGACATACTGGAAAAGACACACAACGGGAA
GCTCTGCGATCTAGATGGAGTGAAGCCTCTAATTTTAAGAGATTGTAGTGTAGCTGGATGGCTCCTCGG
GAACCCAATGTGTGACGAATTCATCAATGTACCGGAATGGTCTTACATAGTGGAGAAGGCCAATCCAA
CCAATGACCTCTGTTACCCAGGGAGTTTCAACGACTATGAAGAACTGAAACACCTATTGAGCAGAATA
AACCATTTTGAGAAAATTCAAATCATCCCCAAAAGTTCTTGGTCCGATCATGAAGCCTCATCAGGAGTT
AGCTCAGCATGTCCATACCTGGGAAGTCCCTCCTTTTTAGAAATGTGGTATGGCTTATCAAAAAGAAC
AGTACATACCCAACAATAAAGAAAAGCTACAATAATACCAACCAAGAGGATCTTTTGGTACTGTGGGG
AATTCACCATCCTAATGATGCGGCAGAGCAGACAAGGCTATATCAAAACCCAACCACCTATATTTCCAT
TGGGACATCAACACTAAACCAGAGATTGGTACCAAAAATAGCTACTAGATCCAAAGTAAACGGGCAAA
GTGGAAGGATGGAGTTCTTCTGGACAATTTTAAAACCTAATGATGCAATCAACTTCGAGAGTAATGGA
AATTTCATTGCTCCAGAATATGCATACAAAATTGTCAAGAAAGGGGACTCAGCAATTATGAAAAGTGA
ATTGGAATATGGTAACTGCAACACCAAGTGTCAAACTCCAATGGGGGCGATAAACTCTAGTATGCCAT
TCCACAACATACACCCTCTCACCATCGGGGAATGCCCCAAATATGTGAAATCAAACAGATTAGTCCTTG
CAACAGGGCTCAGAAATAGCCCTCAAAGAGAGAGCAGGAAGAAAAAAGAGAGGACTATTTGGAGCTAT
AGCAGGTTTTATAGAGGGAGGATGGCAGGGAATGGTAGATGGTTGGTATGGGTACCACCATAGCAATG
AGCAGGGGAGTGGGTACGCTGCAGACAAAGAATCCACTCAAAAGGCAATAGATGGAGTCACCAATAA
GGTCAACTCAATCATTGACAAAATGAACACTCAGTTTGAGGCCGTTGGAAGGGAATTTAATAACTTAG
AAAGGAGAATAGAGAATTTAAACAAGAAGATGGAAGACGGGTTTCTAGATGTCTGGACTTATAATGCC
GAACTTCTGGTTCTCATGGAAAATGAGAGAACTCTAGACTTTCATGACTCAAATGTTAAGAACCTCTAC
GACAAGGTCCGACTACAGCTTAGGGATAATGCAAAGGAGCTGGGTAACGGTTGTTTCGAGTTCTATCA
CAAATGTGATAATGAATGTATGGAAAGTATAAGAAACGGAACGTACAACTATCCGCAGTATTCAGAAG
AAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGAT
GTGCTCCAATGGATCGTTACAATGCAGAATTTGCATTTAAGAGCTCTAAGTTAAAATGCTTCTTCGTCT
CCTATTTATAATATGGTTTGTTATTGTTAATTTTGTTCTTGTAGAAGAGCTTAATTAATCGTTGTTGTTA
TGAAATACTATTTGTATGAGATGAACTGGTGTAATGTAATTCATTTACATAAGTGGAGTCAGAATCAG
AATGTTTCCTCCATAACTAACTAGACATGAAGACCTGCCGCGTACAATTGTCTTATATTTGAACAACTA
AAATTGAACATCTTTTGCCACAACTTTATAAGTGGTTAATATAGCTCAAATATATGGTCAAGTTCAATA
GATTAATAATGGAAATATCAGTTATCGAAATTCATTAACAATCAACTTAACGTTATTAACTACTAATTT
TATATCATCCCCTTTGATAAATGATAGTACA
```

```
CACTTTGTGAGTCTACACTTTGATTCCCTTCAAACACATACAAAGAGAAGAGACT
AATTAATTAATTAATCATCTTGAGAGAAAATGGATTTTCAGGTGCAGATTATCAG
CTTCCTGCTAATCAGTGCTTCAGTCATAATGTCCAGAGGACAAATTGTTCTCTCC
CAGTCTCCAGCAATCCTGTCTGCATCTCCAGGGGAGAAGGTCACAATGACTTGCA
GGGCCAGCTCAAGTGTAAGTTACATCCACTGGTTCCAGCAGAAGCCAGGATCCTC
CCCCAAACCCTGGATTTATGCCACATCCAACCTGGCTTCTGGAGTCCCTGTTCGC
TTCAGTGGCAGTGGGTCTGGGACTTCTTACTCTCACAATCAGCAGAGTGGAGG
CTGAAGATGCTGCCACTTATTACTGCCAGCAGTGGACTAGTAACCCACCCACGTT
CGGAGGGGGGACCAAGCTGGAAATCAAACGTACGGTGGCTGCACCATCTGTCTTC
ATCTTCCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGATAACGC
CCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACA
AAGTCTACGCCTGCGAAGTCACCCATCAGGGCCTGAGCTCGCCCGTCACAAAGAG
CTTCAACAGGGGAGAGTGTTGAGACGTCGTTAAAATGCTTCTTCGTCTCCTATTT
ATAATATGGTTTGTTATTGTTAATTTTGTTCTTGTAGAAGAGCTTAATTAATCGT
TGTTGTTATGAAATACTATTTGTATGAGATGAACTGGTGTAATGTAATTCATTTA
CATAAGTGGAGTCAGAATCAGAATGTTTCCTCCATAACTAACTAGACATGAAGAC
CTGCCGCGTACAATTGTCTTATATTTGAACAACTAAAATTGAACATCTTTTGCCA
CAACTTTATAAGTGGTTAATATAGCTCAAATATATGGTCAAGTTCAATAGATTAA
TAATGGAAATATCAGTTATCGAAATTCATTAACAATCAACTTAACGTTATTAACT
ACTAATTTTATATCATCCCCTTTGATAAATGATAGTACACCAATTAGGAAGGAGA
ATTC
```

590 (LC fragment; SEQ ID NO.15).

Figure 9

```
CACTTTGTGAGTCTACACTTTGATTCCCTTCAAACACATACAAAGAGAAGAGACTAATTAATTAA
TTAATCATCTTGAGAGAAAATGGGTTGGAGCCTCATCTTGCTCTTCCTTGTCGCTGTTGCTACGC
GTGTCCTGTCCCAGGTACAACTGCAGCAGCCTGGGGCTGAGCTGGTGAAGCCTGGGGCCTCAGTG
AAGATGTCCTGCAAGGCTTCTGGCTACACATTTACCAGTTACAATATGCACTGGGTAAAACAGAC
ACCTGGTCGGGGCCTGGAATGGATTGGAGCTATTTATCCCGGAAATGGTGATACTTCCTACAATC
AGAAGTTCAAAGGCAAGGCCACATTGACTGCAGACAAATCCTCCAGCACAGCCTACATGCAGCTC
AGCAGCCTGACATCTGAGGACTCTGCGGTCTATTACTGTGCAAGATCGACTTACTACGGCGGTGA
CTGGTACTTCAATGTCTGGGGCGCAGGGACCACGGTCACCGTCTCTGCAGCTAGCACCAAGGGCC
CATCGGTCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCAGCAGCGTGGTGACCG
TGCCCTCCAGCAGCTTGGGCACCCAGACCTACATCTGCAACGTGAATCACAAGCCCAGCAACACC
AAGGTGGACAAGAAAGTTGAGCCCAAATCTTGTGACAAAACTCACACATGCCCACCGTGCCCAGC
ACCTGAACTCCTGGGGGGACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGAGCAGTA
CAACAGCACGTACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTCCAAAGCC
AAAGGGCAGCCTAGGGAACCACAAGTGTACACTCTTCCACCATCTAGGGATGAGCTTACTAAGAA
CCAAGTTTCTCTTACTTGTCTTGTGAAGGGATTTTATCCATCTGACATCGCCGTGGAATGGGAAT
CCAACGGACAACCAGAGAACAATTACAAGACTACTCCACCAGTTCTTGATTCTGATGGATCCTTC
TTTCTTTATTCCAAGCTTACTGTTGATAAGTCCAGATGGCAGCAAGGAAATGTGTTCTCTTGTTC
TGTTATGCACGAAGCTCTTCATAATCATTATACTCAAAAGTCCCTTTCTCTTTCTCCTGGAAAGT
GAGACGTCGTTAAAATGCTTCTTCGTCTCCTATTTATAATATGGTTTGTTATTGTTAATTTTGTT
CTTGTAGAAGAGCTTAATTAATCGTTGTTGTTATGAAATACTATTTGTATGAGATGAACTGGTGT
AATGTAATTCATTTACATAAGTGGAGTCAGAATCAGAATGTTTCCTCCATAACTAACTAGACATG
AAGACCTGCCGCGTACAATTGTCTTATATTTGAACAACTAAAATTGAACATCTTTTGCCACAACT
TTATAAGTGGTTAATATAGCTCAAATATATGGTCAAGTTCAATAGATTAATAATGGAAATATCAG
TTATCGAAATTCATTAACAATCAACTTAACGTTATTAACTACTAATTTTATATCATCCCCTTTGA
TAAATGATAGTACACCAATTAGGAAGGAGAATTC
```

592 (HC fragment; SEQ ID NO :16).

Figure 10

Figure 14
(Prior ART)
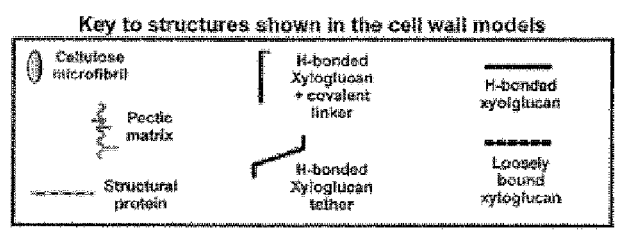
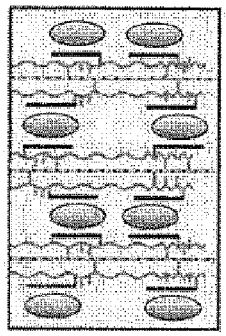
Figure 14A
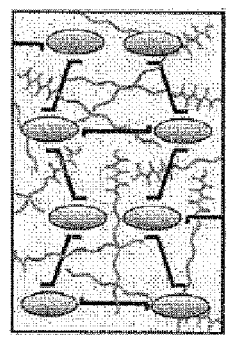
Figure 14B
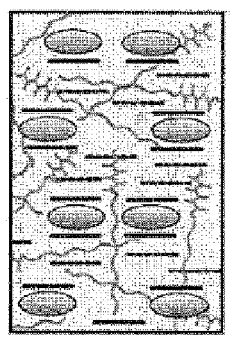
Figure 14C
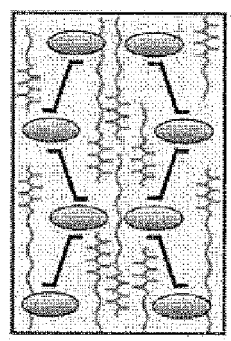
Figure 14D Figure 15
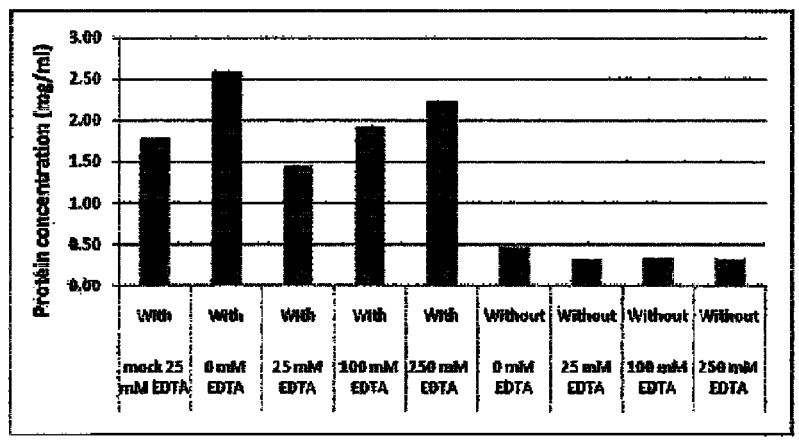
Figure 15A
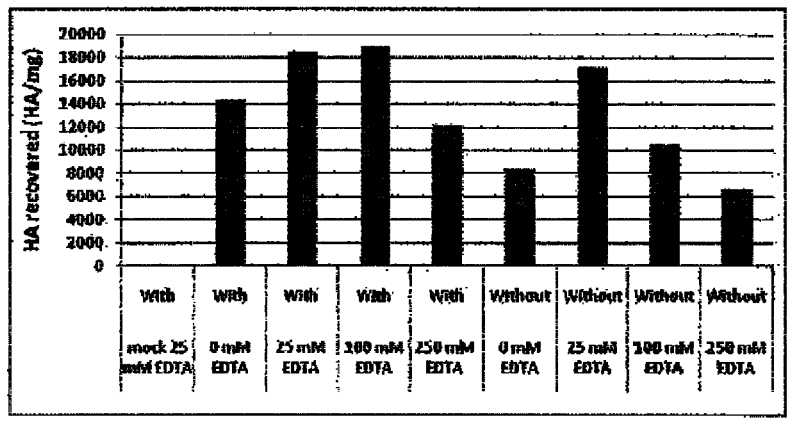
Figure 15B

METHOD FOR RECOVERING PLANT-DERIVED PROTEINS

CROSS REFERENCE TO RELATED APPLICATIONS

The present application is a National Phase Application of International Application No. PCT/CA2012/050180, filed Mar. 23, 2012, which claims the benefit of U.S. Patent Application No. 61/466,889, filed Mar. 23, 2011, which applications are incorporated herein fully by this reference.

FIELD OF INVENTION

The present invention relates to methods of recovering plant-derived proteins. More specifically, the present invention provides methods to obtain proteins, including protein suprastructures, from plants and plant tissues.

BACKGROUND OF THE INVENTION

Current recombinant expression strategies in host cells such as E. coli, insect cell culture, and mammalian cell culture express and secrete proteins at very high level in the culture media. Using these systems high levels of expression, proper protein folding and post-translational modification of proteins, is achieved. Furthermore, purification of the expressed protein is simplified since intracellular proteins may be readily segregated from other components (DNA, vesicle, membranes, pigments, and so on). For plant or yeast expression systems, the cell wall prevents secretion of expressed protein into the culture media.

Different approaches are widely used in science to generate cell-extracts. Mechanical approaches to disrupt cell wall and liberate its content are not usually selective for certain class of protein or cellular components. Directing expression of a protein of interest into the cell culture media, allowing intracellular contaminants to be removed by centrifugation or by filtration, allow simple and fast enrichment of the protein of interest. It may also be desirable to separate a protein or a protein suprastructure of interest, including protein rosettes, nanoparticles, large protein complexes, antibodies or virus-like particles (VLPs), and the like, from some, or all of the proteins, DNA, membrane fragments, vesicles, pigments, carbohydrates, etc. present in the plant or plant matter before the protein or protein suprastructure of interest is used in vaccine formulation.

Immunoglobulins (IgGs) are complex heteromultimeric proteins with characteristic affinity for specific antigenic counterparts of various natures. Today, routine isolation of IgG-producing cell lines, and the advent of technologies for IgG directed evolution and molecular engineering have profoundly impacted their evolution as biotherapeutics and in the general life science market. Therapeutic monoclonal IgG (monoclonal antibodies, mAbs) dominate the current market of new anti-inflammatory and anti-cancer drugs and hundreds of new candidates are currently under research and clinical development for improved or novel applications. The annual market demand for mAbs ranges from a few grams (diagnostics), a few kilograms (anti-toxin) to up to one or several hundreds of kilograms (bio-defense, anti-cancer, anti-infectious, anti-inflammatory). Methods to produce modified glycoproteins from plants is described in WO 2008/151440 (which is incorporated herein by reference).

A method for extracting protein from the intercellular space of plants, comprising a vacuum and centrifugation process to provide an interstitial fluid extract comprising the protein of interest is described in PCT Publication WO 00/09725 (to Turpen et al.). This approach is suitable for small proteins (of 50 kDa or smaller) that pass through network of microfibers under vacuum and centrifugation, but is not suitable for larger proteins, superstructure proteins, protein rosettes, nanoparticles, large protein complexes, such as antibodies or VLPs.

McCormick et al 1999 (Proc Natl Acad Sci USA 96:703-708) discloses use of a rice amylase signal peptide fused to a single-chain Fv (scFv) epitope to target the expressed protein to the extracellular compartment, followed by vacuum infiltration of leaf and stem tissue for recovery of the scFv polypeptides. Moehnke et al., 2008 (Biotechnol Lett 30:1259-1264) describes use of the vacuum infiltration method of McCormick to obtain a recombinant plant allergen from tobacco using an apoplastic extraction. PCT Publication WO 2003/025124 (to Zhang et al) discloses expression of scFv immunoglobulins in plants, targeting to the apoplastic space using murine signal sequences.

Virus-like particles (VLPs) may be employed to prepare vaccines, such as influenza vaccines for example. Suprastructures such as VLPs mimic the structure of the viral capsid, but lack a genome, and thus cannot replicate or provide a means for a secondary infection. VLPs offer an improved alternative to isolated (soluble) recombinant antigens for stimulating a strong immune response. VLPs are assembled upon expression of specific viral proteins and present an external surface resembling that of their cognate virus but, unlike true viral particle, do not incorporate genetic material. The presentation of antigens in a particulate and multivalent structure similar to that of the native virus achieves an enhanced stimulation of the immune response with balanced humoral and cellular components. Such improvement over the stimulation by isolated antigens is believed to be particularly true for enveloped viruses as enveloped VLPs present the surface antigens in their natural membrane-bound state (Grgacic and Anderson, 2006, Methods 40, 60-65). Furthermore, influenza VLPs, with their nanoparticle organization, have been shown to be better vaccine candidates compared to recombinant hemagglutinin HA (i.e. monomeric HA, or HA organized into rosettes; assembly of 3-8 trimers of HA), and they are able to activate both humoral and cellular immune response. (Bright, R. A., et. al., 2007, Vaccine 25, 3871-3878).

The production of influenza HA VLPs that comprise a lipid envelope has been previously described by the inventors in WO 2009/009876 and WO 2009/076778 (to D'Aoust et al.; both of which are incorporated herein by reference). For enveloped viruses, it may be advantageous for a lipid layer or membrane to be retained by the virus. The composition of the lipid may vary with the system (e.g. a plant-produced enveloped virus would include plant lipids or phytosterols in the envelope), and may contribute to an improved immune response.

The assembly of enveloped VLPs in transgenic tobacco expressing the HBV surface antigen (HBsAg) was described by Mason et al. (1992, Proc. Natl. Acad. Sci. USA 89, 11745-11749). Plant-produced HBV VLPs were shown to induce potent B- and T-cell immune responses in mice when administered parenterally (Huang et al., 2005, Vaccine 23, 1851-1858) but oral immunization through feeding studies only induced a modest immune response (Smith et al., 2003, Vaccine 21, 4011-4021). Greco (2007, Vaccine 25, 8228-8240) showed that human immunodeficiency virus (HIV) epitopes in fusion with HBsAg accumulated as VLP when expressed in transgenic tobacco and Arabidopsis, creating a bivalent VLP vaccine.

Expression of the viral capsid protein (NVCP) in transgenic tobacco and potato plants resulted in the assembly of non-enveloped VLPs (Mason et al., 1996, Proc. Natl. Acad. Sci. USA 93, 5335-5340). NVCP VLPs have been produced in agroinfiltrated N. benthamiana leaves (Huang et al. 2009, Biotechnol. Bioeng. 103, 706-714) and their immunogenicity upon oral administration demonstrated in mice (Santi et al., 2008, Vaccine 26, 1846-1854). Administration of 2 or 3 doses of raw potatoes containing 215-751 μg of NVCP in the form of VLPs to healthy adult volunteers resulted in development of an immune response in and 95% of the immunized volunteers (racket et al. 2000, J. Infect. Dis. 182, 302-305). Non-enveloped VLPs have also been obtained from the expression of HBV core antigen (HBcAg; Huang et al., 2009, Biotechnol. Bioeng. 103, 706-714), and the human papillomavirus (HPV) major capsid protein L1 (Varsani et al., 2003, Arch. Virol. 148, 1771-1786).

A simpler protein, or protein suprastructure production system, for example, one that relies on the expression of only one or a few proteins is desirable. Production of proteins, or protein suprastructures, for example but not limited to protein rosettes, nanoparticles, large protein complexes such as antibodies or VLPs, in plant systems is advantageous, in that plants may be grown in a greenhouse or field, and do not require aseptic tissue culture methods and handling.

Methods of recovering proteins or protein suprastructures that are substantially free of, or easily separated from plant proteins, yet retain the structural and characteristics of the proteins or protein suprastructures are desired.

SUMMARY OF THE INVENTION

The present invention relates to methods of recovering plant-derived proteins. More specifically, the present invention provides methods to recover proteins, including protein suprastructures from plants and plant tissues.

It is an object of the invention to provide an improved method of recovering plant-derived proteins.

The present invention provides a method (A) of preparing plant-derived proteins, proteins, or suprastructure proteins, comprising, obtaining a plant or plant matter comprising the plant-derived proteins, proteins, or suprastructure proteins, localized within the apoplast; treating the a plant or plant matter to loosen the cell wall to produce a apoplastic content fraction and a plant cell fraction, the apoplastic content fraction comprising plant-derived proteins, proteins, or suprastructure proteins; and recovering the apoplastic content fraction. The method may further comprise a step of purifying the plant derived proteins, proteins, or suprastructure proteins, from the apoplastic content fraction. The plant-derived proteins, proteins, or suprastructure proteins, may be a chimeric plant-derived proteins, proteins, or suprastructure protein. The plant-derived proteins, proteins, or suprastructure proteins, may be heterologous to the plant. The plant derived proteins, proteins, or suprastructure proteins, may include a protein rosette, a protein complex, a proteasome, a metabolon, a transcription complex, a recombination complex, a photosynthetic complex, a membrane transport complex, a nuclear pore complex, a protein nanoparticle, a glycoprotein, an antibody, a polyclonal antibody, a monoclonal antibody, a single chain monoclonal antibody, a virus like particle (VLP), a viral envelope protein, a viral structural protein, a viral capsid protein, and a viral coat protein, a chimeric protein, a chimeric protein complex, a chimeric protein nanoparticle, a chimeric glycoprotein, a chimeric antibody, a chimeric monoclonal antibody, a chimeric single chain monoclonal antibody, a chimeric hemagglutinin, a viral envelope protein, a viral structural protein, a viral capsid protein, and a viral coat protein. The plant derived monoclonal antibody may comprise a chimeric mouse human monoclonal antibody, for example but not limited to C2B8. The plant derived VLPs may comprise influenza hemagglutinin.

The apoplastic content fraction, and the cell fraction may be produced by treating the plant or plant matter chemically, enzymatically, physically, or a combination thereof. For example the plant or plant matter may be treated with a cell wall loosening composition. The cell wall loosening composition may comprise one or more than one compound selected from a chelator, a hydroxyl radical, indole-3-acetic acid, expansin, pectinase, cellulase, lipase, protease, and a combination thereof. As one of skill would understand, cellulase is a mixture of enzymes and may include one or more endo-1,4-beta-glucanases, cellobiohydrolases (exoccellualses), beta-glucosidases, cellobiose dehydrogenases (oxidative cellulase), cellulose phosphorylases, and hemicellulases.

Furthermore, the apoplastic content fraction and the cell fraction may be produced by infiltrating the cell wall loosening composition by pressure or vacuum infiltration into the plant or plant matter. More specifically, the cell wall loosening composition may comprise one or more enzyme for example one or more than one pectinase, one or more than one cellulase, or one or more than one pectinase and one or more than one cellulase. Therefore, the apoplastic content fraction and the cell fraction may be produced for example by enzymatic infiltration.

The apoplastic content fraction, and the cell fraction may also be produced by treating the plant or plant matter by sonication, or with a cell wall loosening composition combined with sonication.

Plant or plant matter may be obtained by growing, harvesting or growing and harvesting the plant. The plant matter may comprise some or all of the plant, one ore more than one plant cell, leaves, stems, roots or cultured plant cells.

The present invention provides a method of preparing plant derived proteins, proteins, or suprastructure proteins, as described above, wherein a nucleic acid encoding the plant derived proteins, proteins, or suprastructure proteins, is introduced into the plant in a transient manner. Alternatively, the nucleic acid is stably integrated within a genome of the plant.

The present invention also provides a method of preparing plant derived proteins, proteins, or suprastructure proteins, as described above, further comprising a step of purifying the plant derived proteins, proteins, or suprastructure proteins, from the apoplastic content fraction. The step of purifying may comprise filtering the apoplastic content fraction using depth filtration to produce a clarified extract, followed by chromatography of the clarified extract using a cation exchange resin, affinity chromatography, size exclusion chromatography, or a combination thereof.

Without wishing to be bound by theory, proteins obtained from the apoplastic content fraction are more homogenous, as the intermediate forms of post-translationally modified proteins, or proteins comprising other types of processing that occurs in various intracellular compartments, for example the mitochondria, chloroplast, and other organelles are not co-extracted. A higher degree of homogeneity of a recombinant protein typically results in a higher quality of a preparation comprising the protein, and may result in a product with beneficial properties including higher potency, longer half-life, or better immunogenic capacity. For example, blood proteins containing high-mannose glycosylation are eliminated in blood circulation more rapidly than proteins comprising complex glycosylation. A glycosylated protein produce in the apoplastic content fraction exhibits more complex-type glycosylation. Therefore, a protein prepared using the methods described herein, involving cell-wall loosening, exhibit, for example, a better half life in circulation.

The plant derived proteins, proteins, or suprastructure proteins, may include protein rosettes, protein complexes, protein nanoparticles, antibodies, monoclonal antibodies, VLPs. The VLPs may comprise one or more influenza HA polypeptides. The suprastructure protein may be a chimeric suprastructure protein, for example, the monoclonal antibody may be a chimeric monoclonal antibody, or the influenza HA polypeptide, may be a chimeric HA polypeptide. If the suprastructure protein is a VLP, then the plant-derived VLP may further comprise hemagglutinating activity. Plant or plant matter may be obtained by growing, harvesting or growing and harvesting the plant. The plant matter may comprise some or all of the plant, or one or more than one plant cell, leaves, stems, roots or cultured cells.

The present invention also provides a method (B) of preparing plant derived proteins, proteins, or suprastructure proteins, comprising obtaining a plant or plant matter comprising plant-derived proteins, proteins, or suprastructure proteins, treating the plant matter using a cell wall loosening composition, sonication, or a combination thereof, to produced a plant cell fraction and a apoplastic content fraction, and filtering the apoplastic content fraction to produced a filtered fraction and recovering the plant-derived proteins, proteins, or suprastructure proteins, from the filtered fraction.

Without wishing to be bound by theory, plant-made VLPs comprising plant derived lipids, may induce a stronger immune reaction than VLPs made in other manufacturing systems and that the immune reaction induced by these plant-made VLPs is stronger when compared to the immune reaction induced by live or attenuated whole virus vaccines.

The composition of a protein extract obtained from a host cell is complex and typically comprises intercellular and intracellular components along with a protein or suprastructure of interest that is to be isolated. Preparation of a apoplastic content fraction, followed by a step to segregate the cell wall components together with the intracellular proteins and components is advantageous since the protein or suprastructure of interest can be enriched and increase efficiency within a manufacturing process. Having a simpler process, comprising fewer efficient steps, may result in significant yield increases, and cost reduction. It has also been found that the process of loosening the cell wall obtains similar or increased suprastructure protein yield when compared to methods involving digested cell walls (e.g. as described in PCT/CA2010/001489, or PCT/CA2010/001488). Without wishing to be bound by theory, the step of cell wall loosening may loosen the polymeric components of the cells wall and assist in release of the proteins, or suprastructure proteins, otherwise associated within the cell wall. This protocol may also minimize contamination of the proteins, or suprastructure proteins, within intracellular components.

The methods described herein result in less disruption, and contamination of a plant-derived suprastructure protein extract when compared to methods for preparing plant-derived suprastructure protein involving homogenization, blending or grinding. The methods described herein provide a apoplastic content fraction of the plant tissue while maintaining the integrity of protoplasts and their components. The method as described herein is effective in purifying proteins, or suprastructure proteins, even if the protoplasts, or a portion of the protoplasts, lose their integrity and are no longer intact.

These methods provide a higher yield of proteins, or suprastructure proteins, when compared to methods of suprastructure protein extraction involving standard tissue disruption techniques, for example, homogenization, blending or grinding. The greater yield may be due to, in part, a reduction of the shearing forces that disrupt the structural integrity of the proteins, or suprastructure proteins, and in the case of VLPs, the lipid envelope. Preparation of proteins, or suprastructure proteins, from a apoplastic content fraction may be advantageous, as apoplastic content fractions are significantly reduced, or free of, cytoplasmic proteins. Therefore, separation of the suprastructure protein from other proteins and matter, including monomers, dimmers, trimers or fragments of the suprastructure protein, in the apoplastic content fraction is easily carried out. However, increased yields of proteins, or suprastructure proteins, may also be obtained using the methods described herein, even if the protoplast preparation, or a portion of the protoplast preparation, is not intact.

Glycoproteins, including suprastructure glycoproteins, for example monoclonal antibodies, that are secreted into the apoplast comprises a higher percentage of N-glycans that have completed their maturation and comprise terminal N-acetyglucosamine or galactose residues (complex N-glycans), compared to extraction methods that do not loosen the cell wall, for example blender extracted plants. Suprastructure glycoproteins, for example monoclonal antibodies, comprising complex N glycans have been found to exhibit the beneficial property of increased half life in the blood stream when compared to monoclonal antibodies comprising terminal mannose residues (immature N glycans).

By loosening of the cell wall, it may be possible to liberate a pool of apoplastic antibodies comprising N-glycans that have completed their maturation. This method of extraction may allow the recovery of an enriched population, or a homogeneous population of glycosylated antibodies bearing complex N-glycans, separating the immature forms of the glycosylated antibodies in the protoplast fraction. If the pool of antibodies bearing immature N-glycans is desired, the protoplast fraction can be retained and antibodies purified from the protoplast fraction.

The VLPs of the present invention are also characterized as exhibiting a greater hemagglutinating activity than those obtained using standard tissue disruption techniques. This improved hemagglutinating activity may result from a greater yield of intact VLPs (fewer HA monomers or trimers free in solution), a greater yield of intact VLPs with intact lipid envelopes, or a combination thereof.

Vaccines made using VLPs provide the advantage, when compared to vaccines made of whole viruses, that they are non-infectious. Therefore, biological containment is not an issue and it is not required for production. Plant-made VLPs provide a further advantage by allowing the expression system to be grown in a greenhouse or field, thus being significantly more economical and suitable for scale-up.

Additionally, plants do not comprise enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2 shows A) the nucleic acid sequence (SEQ ID NO. 1) of a portion of construct for expressing H5/Indo (construct number 685) from PacI (upstream of the 35S promoter) to AscI (immediately downstream of the NOS terminator). Coding sequence of H5 from A/Indonesia/5/2005 is underlined. FIG. 2B shows the amino acid sequence (SEQ ID NO. 2) of H5 A/Indonesia/5/05 hemagglutinin encoded by construct number 685.

FIG. 3 shows characterization of hemagglutinin (HA)-containing structures by size exclusion chromatography (SEC). Following centrifugation of the digested plant extract, the pellet was resuspended and fractionated by SEC.

FIG. 5 shows the nucleic acid sequence (SEQ ID NO: 9) of an HA expression cassette comprising alfalfa plastocyanin promoter and 5' UTR, hemagglutinin coding sequence of H5 from A/Indonesia/5/2005 (Construct #660), alfalfa plastocyanin 3' UTR and terminator sequences.

FIG. 9 shows the sequence of the DNA fragment synthesized for the assembly of construct #590 (LC fragment; (SEQ ID NO.15).

FIG. 10 shows the sequence of the DNA fragment synthesized for the assembly of construct #592 (HC fragment) (SEQ ID NO.16).

FIG. 14A shows a model (covalently cross-linked model) of a plant cell wall. In this model, cell wall matrix polymers (xyloglucan, pectin, and glycoprotein) are covalently linked to one another. The binding of xyloglucan to cellulose microfibrils results in a non-covalently cross-linked cellulose-hemicellulose network that gives the wall tensile strength. FIG. 14B shows an alternate model (Tether model) of a plant cell wall. In this model, xyloglucan molecules are hydrogen bonded to and cross-link cellulose microfibrils. The cellulose-xyloglucan network is meshed in a non-covalently cross-linked pectic network. FIG. 14C shows another alternate model (Diffuse layer model) of a plant cell wall. In this model, xyloglucan molecules are hydrogen bonded to the surface of cellulose microfibrils but do not directly cross link them. The tightly-bound xyloglucan is surrounded by a layer of less-tightly bound polysaccharides. The cellulose and xyloglucan are embedded in a pectic matrix. FIG. 14D shows an alternate model (stratified layer model) of a plant cell wall. In this model xyloglucan molecules are hydrogen bonded to and cross-link cellulose microfibrils. The cellulose-xyloglucan lamellae are separated by strata of pectic polysaccharides.

FIG. 15 shows protein released upon plant treatment with EDTA containing buffer, with or without the usage of cell-wall depolymerization enzymes. FIG. 15A Protein concentration was measured using the Bradford assay. FIG. 15B HA activity is expressed as the inverse of the lowest quantity of protein extractable to hemagglutinate red blood cells.

DETAILED DESCRIPTION

Figure 1:
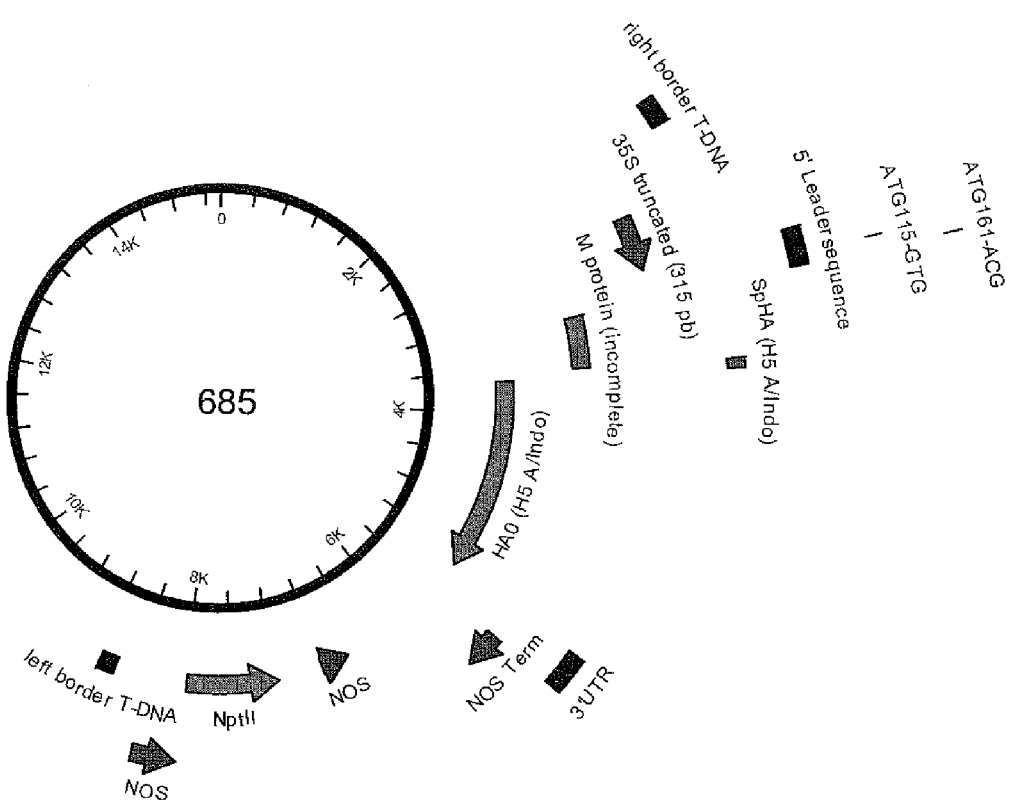
FIG. 1 shows a schematic representation of CPMVHT-based expression cassette (construct 685) for the expression of H5 A/Indonesia/5/05 hemagglutinin.

The present invention relates to methods of recovering plant-derived proteins. More specifically, the present invention provides methods to recover proteins, or protein suprastructures, from plants and plant tissues.

The following description is of a preferred embodiment.

The present invention provides a method for recovering plant-derived proteins or protein suprastructures of interest. The protein of interest may be present in the apoplast or extracellular compartment, corresponding to the plant cell portion excluding the protoplast/spheroplast compartment. The method involves loosening the cell wall, for example by degrading, partially degrading, cleaving, partially cleaving or otherwise structurally changing cell wall polymeric components and their associated linkages, within the cell wall, breaking intermolecular non-covalent, or covalent, bonds within, or between, cell wall polymers. The method may, or may not involve the release of protoplast or spheroplast from the plant cell.

By the term "protoplast" is meant a plant cell that has had its cell wall completely or significantly removed, for example from about 50% to about 100%, or any amount therebetween of the cell wall, may be removed. For example from about 50, 55, 60, 65, 70, 75, 80, 85, 90, 95 100%, or any amount therebetween of the cell wall, may be removed. A spheroplast may have partial removal of the cell wall, for example from about 10% to about 49%, or any amount therebetween of the cell wall, may be removed. For example from about 10, 15, 20, 25, 30, 35, 40, 45, 49%, or any amount therebetween of the cell wall, may be removed.

The "apoplast" is the portion of the plant cell comprised between the plasma membrane and the cell wall, and includes the cell wall and intercellular spaces of the plant. While it is preferred that the integrity of the protoplasts (and/or spheroplasts) be maintained during digestion and further processing, it is not required that the protoplasts remain intact in order to enrich for proteins, or suprastructure proteins as described herein. Preferably, the plasma membrane of the protoplast or spheroplast has not been degraded, partially degraded, cleaved, partially cleaved or otherwise structurally changed, loosened or had its integrity changed, but, for example, about 5, 10, 15, 20, 25, 30, 35, 40, 45, 50, 55, 60, 65, 70, 75, 80, 85, 90, 95% or any amount therebetween of the plasma membrane may be degraded, cleaved, structurally changed, loosened or removed.

By the term "cell wall" is meant the structure forming the outer cell compartment of a plant cell, and located outside of the plasma membrane, bordering the apoplast. Without being bound by theory, the cell wall is thought to be made of a matrix of polymers such as cellulose microfibrils linked via hemicellulosic tethers to form a cellulose-hemicellulose network embedded in a pectin matrix (see FIGS. 14A-14D for several non-limiting models of a plant cell wall). Cell wall components can include, as non-limitative examples, polysaccharides, cellulose, hemicellulose (such as xylan, xyloglucan, glucuronoxylan, arabinoxylan, glucuronarabinoxylan, mannan, glucomannan, galactomannan, galactoglucomannan), pectin (such as homogalacturonans, rhamnogalacturonans I, rhamnogalacturonans II, oligogalacturonides, substituted galacturonans, xylogalacturonans, apiogalacturonans), polymers, lignin, cutin, suberin, glycoproteins, hydroxyproline-rich glycoproteins, arabinogalactan proteins, glycine-rich proteins, proline-rich proteins, extensins, expansins, minerals, calcium, calcium pectate, magnesium, magnesium pectate, borate, phenolic esters, ferulic acid, coumaric acid.

Structurally, the cell wall components, particularly the cellulose-hemicellulose network embedded in the pectin matrix forms contributes in the semi-permeable nature of the cell wall. In a physiological environment, the cell wall normally allows for the passage of small molecules via the meshes formed by the cell wall components. Loosening the cell wall involves a loosening of the interactions of cell wall components with one another, and results, directly or indirectly, as an enlarging or stretching of the meshes, thus allowing the passage of larger molecules than those who would normally be allowed to pass through the cell wall. The passage of large molecules through the loosened cell wall can be facilitated by forces acting on the normal passage of small molecules through the non-loosened cell wall, such as for example turgor pressure, osmotic pressure and hydrostatic pressure. The present method can include the use of reagents, chemicals or biological, that will act on one or more of those forces to further facilitate the passage of large molecules.

By "cell wall loosening" it is meant a modification of the cell wall that results in structural changes in the cell wall, that may result in relaxation of wall tension, wall stress relaxation, irreversible wall extension (wall creep), or degradation, partial or complete, of one or more components of the cell wall. For example, and without wishing to be bound by theory, cell wall loosening may arise as a result of breaking bonds between various components within the cell wall, for example, load-bearing bonds within the cell wall. Structural change may take place for example by cleaving, partially cleaving, degrading or partially degrading cell wall components, breaking intermolecular non-covalent, or covalent, bonds within, or between, cell wall components, or other modifications that weaken the cell wall, disrupt the cell wall matrix, or a combination thereof. Loosening may occur in localized regions of the wall, at target components within the cell wall, or loosening may be generally dispersed throughout the cell wall. Cell wall loosening, for example, may take place upon physical treatment of the plant cell such as sonication, chemical, enzymatic, both chemical and enzymatic treatment with a cell wall loosening composition, or a combination of sonication and treatment with a cell wall loosening composition, or a combination of infiltration (using vacuum or pressure) and treatment with a cell wall loosening composition. Loosening of the cell wall may result in partial digestion of the cell wall. Plant cells that have undergone a treatment to loosen the cell wall may still comprise the plant cell wall, or part of the plant cell wall, in a modified form. Further, the loosening of the cell wall can include a partial degradation or removal of the cell wall, such as from 0% to about 60% or any amount therebetween of the cell wall that is degraded or removed, from 0% to about 30% or any amount therebetween of the cell wall that is degraded or removed, or from 0, 5, 10, 15, 20, 25, 30, 35, 40, 45, 50, 55, 60, 65, 70, 75, 80, 85, 90% or any amount therebetween, of the cell wall that is degraded or removed. However, protoplasts, spheroplasts, or both protoplasts and spheroplasts may also be produced. Some plant cells within a population of cells following one or more treatments as described herein to loosen the cell wall may comprise protoplasts, for example from about 0% to about 50%, or any amount therebetween of the cell population may comprise protoplasts, for example 0% to about 30% or any amount therebetween, from 0% to about 10% or any amount therebetween of the cell population may comprise protoplasts, or from 0, 5, 10, 15, 20, 25, 30, 35, 40, 45, 50% or any amount therebetween, of the cell population may comprise protoplasts. Similarly, some plant cells may comprise spheroplasts, for example from about 0% to about 90%, or any amount therebetween of the cell population may comprise sphroplasts, for example 0% to about 60% or any amount therebetween, from 0% to about 30% or any amount therebetween of the cell population may comprise spheroplasts, or from 0, 5, 10, 15, 20, 25, 30, 35, 40, 45, 50, 55, 60, 65, 70, 75, 80, 85, 90% or any amount therebetween, of the cell population may comprise spheroplasts.

By the term "cell wall loosening composition" is meant any composition that results in cell wall loosening, for example, that modifies the cell wall such that components within the cell wall are cleaved, partially cleaved, degraded or partially degraded, or that break intermolecular non-covalent, or covalent, bonds within, or between, cell wall components, or other modifications that weaken the cell wall, disrupt the cell wall matrix, or a combination thereof. Examples of cell wall loosening compositions include chemicals that disrupt or hydrolyze cell wall components, enzymes that disrupt or hydrolyze cell wall components, biologicals that disrupt or hydrolyze cell wall components, or any combination of at least two of chemicals, biological and enzymes that disrupt or hydrolyze cell wall components. Non limiting examples of chemicals include chelators, for example a divalent cation chelator such as EDTA or EGTA, proton donors, a hydroxyl radical, potassium hydroxide, indole-3-acetic acid, imidazole, and a combination thereof. Non limiting examples of biologicals include auxin, expansin, for example one or more alpha-expansin or beta-expansin, and a combination thereof. Non limiting examples of enzymes include glycanases, galacturonases, polygalacturonases, xylanases, pectinases, pectolyases, pectozymes, pectinesterases, methyltransferases, cellulases, glucanases, endo-1,4-beta-glucanases, xyloglucan transglucosylhydrolases, xyloglucan endoglucanases, xyloglucan endotransglucosylase, cellobiohydrolases (exocellulases), glycoside hydrolases, beta-glucosidases, cellobiose dehydrogenases (oxidative cellulase), cellulose phosphorylases, hemicellulases, lipases, proteases, and a combination thereof. As described in the Examples below (for example, Example 1) a non-limiting example of an enzyme mixture that may be used is a pectinase, MACEROZYME (Yakult Pharmaceuticals) and a cellulase composition, Onozuka R-10 (Yakult Pharmaceuticals). In another non-limiting example (Example 17; FIG. 16) an enzyme mixture that may be used comprises a pectinase used alone or in combination, for example Biocatalysts 162L, Biocatalysts 444L, Biocatalysts PDN33. The pectianse, or pectinase composition, may also be used along with cellulase, for example Multifect CX CG, Multifect CX B (Genencor), or a combination thereof. If the cell wall loosening composition comprises an enzyme mixture that may be used for protoplast preparations (e.g. as described in Examples below: "VLP extraction by cell wall digestion", Example 1 and Example 17; also see PCT/CA2010/001489, or PCT/CA2010/001488; which are incorporated herein by reference), then the amount of enzyme used, and/or the digestion time or any other digestion parameter, is less than that typically used to prepare protoplasts. For example, the amount of enzyme used may be from 0.1 to about 75%, or any amount therebetween of the amount that would normally be used to prepare protoplasts. For example, the amount of enzyme used as a cell wall loosening composition will produce a plant cell composition comprising from 0 to about 50% or any amount therebetween of protoplasts. Alternatively, the amount of enzyme used as a cell wall loosening composition may be similar to that used to prepare protoplasts (e.g. as described in Examples "VLP extraction by cell wall digestion", and Example 1; and PCT/CA2010/001489, or PCT/CA2010/001488; which are incorporated herein by reference), but the duration of incubation is reduced by about 30 to about 80%, or any amount therebetween, of the duration that would normally be used to prepare protoplasts.

The cell wall loosening composition, for example an enzyme solution or digestion solution, may be infiltrated in a whole plant, a plant organ, or whole leaf using for example vacuum infiltration (see Example 17; for example using conditions similar to that as described in D'Aoust et al., 2008 Plant Biotechnology J. 6:930-940; WO 00/063400; WO 00/037663 which are incorporated herein by reference) or pressure infiltration (for example using a pressure from about 1 to about 150 kPa or any amount therebetween for about 1 min to 10 hours). By whole plant it is meant a plant comprising roots, stem and leaves. By a plant organ it is meant the root system, the aerial portion of a plant (stem with leaves), the stem with leaves removed, the flower, or one or more leaves (with or without the petiole). By whole leaf (or whole leaves) it is meant a leaf or one or more leaves (with or without the petiole) that is removed from the plant but is otherwise intact in that it is not cut into smaller pieces. As described herein, infiltration of a cell wall loosening composition within for example, a whole plant, or one or more whole leaves, allows the release of proteins, suprastructure proteins or VLPs from whole plants or leaves. Without wishing to be bound by theory, when a cell wall loosening composition is not infiltrated within a whole leaf, there is a need to increase entry points within the leaf for the composition so that the enzyme composition can digest the tissue gradually. For example when cell wall loosening composition is provided as a solution in which leaves are soaked, enzymatic digestion occurs from the exposed margins towards the inner part of the leaf tissue. This process is enhanced using mechanical agitation resulting in the release of protoplasts or spheroplasts from the pectocellulosic matrix. Infiltration of a cell wall loosening composition may require reduced mechanical agitation, both in intensity and duration, and help maintain protoplast integrity, and increase protoplast yield. When enzymes are infiltrated within a leaf (or organ or whole plant) continuous agitation of the leaf (organ or plant) may be carried out, but agitation may not be required.

By treating the cell wall with a cell wall loosening composition the plant-derived proteins or protein suprastructures of interest may be more readily released. By using a method comprising a step of cell wall loosening, the plant-derived proteins or protein suprastructures of interest may be enriched since the cell wall and protoplast compartment that contains a majority of the host-cell proteins are segregated from the released plant-derived proteins or protein suprastructures of interest.

By "plant-derived protein", "protein" or "protein of interest" (these terms are used interchangeably), it is meant a protein, or protein subunit encoded by a nucleotide sequence, or coding region, that is to be expressed within a plant or portion of the plant, including proteins and protein subunits that are exogenous to the plant or portion of the plant. Proteins may have a molecular weight from about 1 to about 100 kDa or any amount therebetween, for example, 1, 2, 4, 6, 8, 10, 12, 14, 16, 18, 20, 22, 24, 26, 28, 30, 35, 40, 45, 50, 55, 60, 65, 70, 75, 80, 85, 90, 95, 100 kDa, or any amount therebetween. A protein may be monomeric, dimeric, trimeric, or multimeric.

A protein suprastructure, also termed suprastructure protein, protein superstructure, or superstructure protein, is a protein structure comprised of two or more polypeptides. The polypeptides may be the same, or different; if different, they may be present in a ratio of about 1:1 to about 10:1 or greater. Suprastructure proteins, may include, but are not limited to protein rosettes, protein complexes, protein nanoparticles, glycoproteins, antibodies, polyclonal antibodies, monoclonal antibodies, single chain monoclonal antibodies, or virus like particles, proteasomes, metabolons, transcription complexes, recombination complexes, photosynthetic complexes, membrane transport complexes, nuclear pore complexes, chimeric proteins, chimeric protein complexes, chimeric protein nanoparticles, chimeric glycoproteins, chimeric antibodies, chimeric monoclonal antibodies, chimeric single chain monoclonal antibodies, or chimeric hemagglutinin (HA). If the protein suprastructure is a VLP, the VLP may be selected from the group of viral envelope proteins, viral structural proteins, viral capsid proteins, and viral coat proteins. The plant derived VLPs may comprise influenza (HA).

Typically a protein suprastructure (protein superstructure), when assembled, is large, for example having a molecular weight greater than 75 kDa, for example from about 75 to about 1500 kDa or any molecular weight therebetween. For example, the protein suprastructure may have a molecular weight from about 75, 80, 85, 90, 100, 110, 120, 130, 140, 150, 160, 170, 180, 200, 220, 240, 260, 280, 300, 320, 340, 360, 380, 400, 425, 450, 475, 500, 525, 550, 575, 600, 625, 650, 675, 700, 725, 750, 775, 800, 850, 900, 950, 1000, 1100, 1150, 1200, 1250, 1300, 1350, 1400, 1450, 1500 kDa, or any amount therebetween, Subunits that combine together to make up the protein suprastructure may be of a smaller molecular weight, for example each subunit having a molecular weight from about 1 kDa to about 500 kDa, or any amount therebetween. A protein suprastructure may comprise a protein exhibiting a secondary structure, with one or more amino acids hydrogen bonded, for example with residues in protein helices, a tertiary structure, having a 3-dimensional configuration, or a quaternary structure having an arrangement of multiple folded proteins or coiled protein molecules that form a multi-subunit complex.

A multiprotein complex (or a protein complex) may comprise a group of two or more associated polypeptide chains. If the different polypeptide chains contain different protein domains, then the resulting multiprotein complex can have multiple catalytic functions. The protein complex may also be a multienzyme polypeptide, comprising multiple catalytic domains within a single polypeptide chain.

Protein complexes are typically in the form of quaternary structure. Examples of protein complexes that typically may not survive intact using standard protein isolation protocols, but that may be obtained using the methods described herein include proteasomes (for degradation of peptides and proteins), metabolons (for oxidative energy production), ribosomes (for protein synthesis; e.g. as described in Pereira-Leal, J. B.; et. al., 2006, Philos Trans R Soc Lond B Biol Sci., 361(1467):507-517), transcription complexes, recombination complexes, photosynthetic complexes, membrane transport complexes, nuclear pore complexes. The present method may be used to obtained protein complexes that are characterized as having stable or weaker protein domain-protein domain interactions.

Examples of a protein, or a protein suprastructure, include, for example but not limited to, an industrial enzyme for example, cellulase, xylanase, protease, peroxidase, subtilisin, a protein supplement, a nutraceutical, a value-added product, or a fragment thereof for feed, food, or both feed and food use, a pharmaceutically active protein, for example but not limited to growth factors, growth regulators, antibodies, antigens, and fragments thereof, or their derivatives useful for immunization or vaccination and the like. Additional proteins of interest may include, but are not limited to, interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

A non-limiting example of a protein suprastructure is an antibody. Antibodies are glycoproteins that have a molecular weight from about 100 to about 1000 kDa, or any amount therebetween. Antibodies comprise four polypeptide chains, two light chains and two heavy chains, which are connected by disulfide bonds. For example, which is not to be considered limiting, each light chain may have a molecular weight of approx. 25 kDa, for example from about 20 to about 30 kDa or any amount therebetween, or more for example from about 20 to about 300 kDa or any amount therebetween, and is composed of two domains, one variable domain ($V_L$) and one constant domain ($C_L$). Each heavy chain may have a molecular weight of approx. 50 kDa, for example from about 30 to about 75 kDa, or any amount therebetween, or more for example from about 30 to about 500 kDa or any amount therebetween, and consists of a constant and variable region. The heavy and light chains contain a number of homologous sections consisting of similar but not identical groups of amino acid sequences. These homologous units consist of about 110 amino acids and are called immunoglobulin domains. The heavy chain contains one variable domain ($V_H$) and either three or four constant domains ($C_H1$, $C_H2$, $C_H3$, and $C_H4$, depending on the antibody class or isotype). The region between the $C_H1$ and $C_H2$ domains is called the hinge region and permits flexibility between the two Fab arms of the Y-shaped antibody molecule, allowing them to open and close to accommodate binding to two antigenic determinants separated by a fixed distance.

Another non-limiting example of a protein suprastructure is a VLP. The VLP may comprise an HA0 precursor form, or the HA1 or HA2 domains retained together by disulphide bridges form. A VLP may have an average size of about 20 nm to 1 µm, or any amount therebetween, for example 60, 65, 70, 75, 80, 85, 90, 95, 100, 105, 110, 120, 130, 140, 150 160, 170, 180, 190, or 200 nm, or any amount therebetween, for example 100 nm, and may include a lipid membrane.

The proteins, or suprastructure proteins, may further comprise one or more lipids, phospholipids, nucleic acids, membranes or the like. Two or more polypeptides may be connected by a covalent bond, a disulfide bridge, charge interaction, hydrophobic attraction, van der waals forces, hydrogen bonds or the like. An example of a protein suprastructure is a monoclonal antibody, a chimeric monoclonal antibody, a single chain monoclonal antibody, or a virus like particle (VLP) which may be enveloped, or non-enveloped, for example, a viral envelope protein, a viral structural protein, a viral capsid protein, or a viral coat protein.

Proteins, or suprastructure proteins, may be produced in suitable host cells including plant host cells, and if desired further purified. While a chimeric monoclonal antibody, an influenza VLP, and chimeric influenza VLP are exemplified herein, the methods described herein may be used for any cytosolic plant-derived protein or suprastructure protein, or any plant-derived protein or suprastructure protein that localize in, or are secreted to, the apoplast.

The present invention also provides a method of recovering plant-derived proteins, proteins, or suprastructure proteins from plant or plant matter, that involves obtaining plant or plant matter comprising plant-derived proteins, proteins, or suprastructure proteins localized within the apoplastic content; treating the plant or plant matter with a cell wall loosening composition, sonication, or both a cell wall loosening composition and sonication, to produce a plant or plant matter having a loosened cell wall, thus allowing, stimulating, increasing or enhancing the release of the apoplastic content through the cell wall, thereby producing an apoplastic content fraction; filtering the apoplastic content fraction to produced a filtered fraction and recovering the plant-derived proteins, proteins, or suprastructure proteins, from the filtered fraction. If desired, the plant derived proteins, proteins, or suprastructure proteins, may be purified from the filtered fraction. Alternative methods known in the art for recovering proteins or suprastructure proteins from the apoplastic content fraction can be used, including, for example, centrifugation and decantation.

The present invention also provides a method of recovering a protein or suprastructure protein, wherein the protein or suprastructure protein comprises a plant derived lipid envelope, for example a VLP comprising a plant-derived lipid envelope. The method includes obtaining a plant, or plant matter comprising the suprastructure protein of interest, for example the VLP, treating the plant or plant matter with a cell wall loosening composition, sonication, or both a cell wall loosening composition and sonication, to produce a plant or plant matter having a loosened cell wall, thus allowing, stimulating, increasing or enhancing the release of the apoplastic content through the cell wall, thereby producing an apoplastic content fraction, and separating suprastructure protein of interest comprising a plant-derived lipid envelope. from the apoplastic content fraction.

Standard reference works setting forth the general principles of plant tissue culture, cultured plant cells, and production of protoplasts, spheroplasts and the like include: *Introduction to Plant Tissue Culture*, by M K Razdan 2$^{nd}$ Ed. (Science Publishers, 2003; which is incorporated herein by reference), or see for example, the following URL: molecular-plant-biotechnology.info/plant-tissue-culture/protoplast-isolation.htm. Methods and techniques relating to protoplast (or spheroplast) production and manipulation are reviewed in, for example, Davey M R et al., 2005 (Biotechnology Advances 23.131-171; which is incorporated herein by reference). Standard reference works setting forth the general methods and principles of protein biochemistry, molecular biology and the like include, for example Ausubel et al, Current Protocols In Molecular Biology, John Wiley & Sons, New York (1998 and Supplements to 2001; which is incorporated herein by reference); Sambrook et al, Molecular Cloning: A Laboratory Manual, 2d Ed., Cold Spring Harbor Laboratory Press, Plainview, N.Y., 1989 (which is incorporated herein by reference); Kaufman et al, Eds., Handbook Of Molecular And Cellular Methods In Biology And Medicine, CRC Press, Boca Raton, 1995 (which is incorporated herein by reference); McPherson, Ed., Directed Mutagenesis: A Practical Approach, IRL Press, Oxford, 1991 (which is incorporated herein by reference).

Enzymes useful for modifying and thereby loosening the cell wall are known to one of skill in the art and may include cellulase (EC 3.2.1.4), pectinase (EC 3.2.1.15), xylanase (EC 3.2.1.8), chitinases (EC 3.2.1.14), hemicellulase, xyloglucan endotransglycosylase glucanases, xyloglucan endotransglycosylase, endoglycanases such as $\beta$-1,3-glucanase and fl-1,4-mannanase, xyloglucan endotransglucosylase/hydrolases or a combination thereof. Cellulase is a mixture of enzymes and may include one or more endo-1,4-beta-glucanases, cellobiohydrolases (exocellulases), beta-glucosidases, cellobiose dehydrogenases (oxidative cellulase), cellulose phosphorylases, and hemicellulases. Non-limiting examples of suitable enzymes that may be used as a cell wall loosening composition include a multi-component enzyme mixture comprising cellulase, hemicellulase, and pectinase, for example MACEROZYME™ (containing approximately: Cellulase: 0.1 U/mg, Hemicellulase: 0.25 U/mg, and Pectinase: 0.5 U/mg). Other examples of commercial enzymes, enzyme mixtures and suppliers are listed in Table 1 (see: *Introduction to Plant Tissue Culture*, by M K Razdan 2$^{nd}$ Ed., Science Publishers, 2003).

Alternate names, and types of cellulases include endo-1, 4-$\beta$-D-glucanase; $\beta$-1,4-glucanase; $\beta$-1,4-endoglucan hydrolase; cellulase A; cellulosin AP; endoglucanase D; alkali cellulase; cellulase A 3; celludextrinase; 9.5 cellulase; avicelase; pancellase SS and 1,4-(1,3;1,4)-$\beta$-D-glucan 4-glucanohydrolase. Alternate names, and types of pectinases (polygalacturonases) include pectin depolymerase; pectinase; endopolygalacturonase; pectolase; pectin hydrolase; pectin polygalacturonase; endo-polygalacturonase; poly-$\alpha$-1,4-galacturonide glycanohydrolase; endogalacturonase; endo-D-galacturonase and poly(1,4-$\alpha$-D-galacturonide) glycanohydrolase. Alternate names, and types of xylanases include hemicellulase, endo-(1→4)-$\beta$-xylan 4-xylanohydrolase; endo-1,4-xylanase; xylanase; $\beta$-1,4-xylanase; endo-1,4-xylanase; endo-$\beta$-1,4-xylanase; endo-1,4-$\beta$-D-xylanase; 1,4-$\beta$-xylan xylanohydrolase; $\beta$-xylanase; $\beta$-1,4-xylan xylanohydrolase; endo-1,4-$\beta$-xylanase; $\beta$-D-xylanase. Alternate names, and types of chitinases include chitodextrinase; 1,4-$\beta$-poly-N-acetylglucosaminidase; poly-$\beta$-glucosaminidase; $\beta$-1,4-poly-N-acetyl glucosamidinase; poly[1,4-(N-acetyl-$\beta$-D-glucosaminide)]glycanohydrolase.

TABLE 1

Non-limiting examples of commercially available enzymes for cell wall loosening

| Enzyme | Source | Supplier |
|---|---|---|
| Cellulases | | |
| Cellulase ONOZUKA R-10 | *Trichoderma viride* | Kinki Yakult Mfg. Col. Ltd. 8-12, Shinglkancho Nishinomiya, Japan |
| Cellulase ONOZUKA RS | *T. viride* | Yakult Honsha Co., Tokyo, Japan |
| Cellulase YC | *T. viride* | Seishin Pharma Co. Ltd. 9-500-1, Nagareyama Nagareyama-shi, Chiba-kan, Japan |
| Cellulase CEL | *T. viride* | Cooper Biomedical Inc. Malvern, PA, USA |
| Cellulysin | *T. viride* | Calbiochem, San Diego, CA, USA |
| Driselase | *Irpex locteus* | Kyowa Hakko Kogyo Co. Ltd., Tokyo, Japan |
| Melcelase P-1 | *T. viride* | Meiji Seiki Kaisha Ltd. No. 8, 2-Chome Kyobashi, Chou-Ku, Japan |
| Multifect CX GC | *T. viride* | Genencor |
| Multifect CX B | *T. viride* | Genencor |
| Hemicellulases | | |
| Hellcase | *Helix pomatia* | Industrie Biologique Francaise, Gennevilliers, France |
| Hemicellulase | *Aspergillus niger* | Sigma Chemical Co., St. Louis, MO, USA |
| Hemicellulase H-2125 | *Rhizopus* sp. | Sigma, Munchen |
| Rhozyme HP 150 | *Aspergillus niger* | Genencor Inc., South San Francisco, CA, USA |
| Pectinases | | |
| MACERASE | *Rhizopus arrhizus* | Calbiochem, San Diego, CA, USA |
| MACEROZYME R-10 | *R. arrhizus* | Yakult Honsha Co., Tokyo, Japan |
| Multifect Pectinase FE | *A. niger* | Genencor |
| PATE | *Bacillus polymyza* | Farbwerke-Hoechst AG, Frankfurt, FRG |
| Pectinol | *Aspergillus* sp. | Rohm and Haas Co. Independence Hall West, Philadelphia, PA 19105, USA |
| Pectolyase Y-23 | *Aspergillus joponicus* | Seishin Pharma Co. Ltd., Japan |
| Zymolyase | *Arthrobacter luteus* | Sigma Chemical Co., USA |
| Biocatalyst 162L | | Biocatalysts |
| Biocatalyst 444L | | Biocatalysts |
| Biocatalyst PDN33 | | Biocatalysts |

Choice of a particular enzyme or combination of enzymes, and concentration and reaction conditions may depend on the type of plant tissue used from which the cell and loosened fraction comprising the VLPs is obtained. A mixture of cellulase, hemicellulase and pectinase, for example, a pectinase MACEROZYME™ or Multifect, may be used in a concentration ranging from 0.01% to 2.5% (v/v), for example 0.01, 0.02, 0.04, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5% (v/v), or any amount therebetween. MACEROZYME™ or Multifect may be used alone, or in combination with other enzymes, e.g cellulase, pectinase, hemicellulase, or a combination thereof. Cellulase may be used in a concentration ranging from 0.1% to 5%, for example 0.1, 0.25, 0.5, 0.75, 1.0, 1.25, 1.5, 1.75, 2.0, 2.25, 2.5, 2.75. 3.0. 3.25, 3.5, 3.75, 4.0, 4.25, 4.5, 4.75, 5.0% (w/v) or any amount therebetween. Furthermore, pectinase, for example but not limited to Biocatalysts 162L and 144L (comprising polygalacturonidase and pectin lyase activity), may be used alone, or in combination with other enzymes, e.g cellulase, pectinase, hemicellulase, or a combination thereof. Pectinase (comprising polygalacturonidase and pectin lyase activity) may be used in a concentration ranging from 0.1% to 5%, for example 0.1, 0.25, 0.5, 0.75, 1.0, 1.25, 1.5, 1.75, 2.0, 2.25, 2.5, 2.75. 3.0. 3.25, 3.5, 3.75, 4.0, 4.25, 4.5, 4.75, 5.0% (w/v) or any amount therebetween.

The enzyme solution (alternately referred to as a cell wall loosening composition) will generally comprise a buffer or buffer system, an osmoticum, and one or more than one salts, divalent cations or other additives. The buffer or buffer system is selected to maintain a pH in the range suitable for enzyme activity and the stability of the protein(s), or VLP, to purify, for example, within the range of about pH 5.0 to about 8.0, or any value therebetween. The selected pH used may vary depending upon the VLP to be recovered, for example the pH may be 5.0, 5.2, 5.4, 5.6, 5.8, 6.0, 6.2, 6.4, 6.6, 6.8, 7.0, 7.2, 7.4, 7.6, 7.8, 8.0, or any pH therebetween. Examples of buffers or buffer systems include, but are not limited to, MES, phosphate, citrate and the like. One or more buffers or buffer systems may be combined in an enzyme solution (cell wall loosening solution); the one or more buffers may be present at a concentration from 0 mM to about 200 mM, or any amount therebetween, for example 10, 20, 30, 40, 50, 60, 70, 80, 90, 100, 110, 120, 130, 140, 150, 160, 170, 180 or 190 mM or any amount therebetween. Depending on the suitability, an osmoticum component can be added if desired. The osmoticum and its concentration are selected to raise the osmotic strength of the enzyme solution. Examples of osmoticum include mannitol, sorbitol or other sugar alcohols, polyethylene glycol (PEG) of varying polymer lengths, and the like. Concentration ranges of osmoticum may vary depending on the plant species, the type of osmoticum used, and the type of plant tissue selected (species or organ of origin e.g. leaf or stem)—generally the range is from 0 M to about 0.8 M, for example 0.05, 0.1, 0.15, 0.2, 0.25, 0.3. 0.35, 0.4, 0.5, 0.6, 0.7, or 0.75 M, or any amount therebetween, for example, 0, 50, 100, 150, 200, 250, 300, 350, 400, 450, 500, 550, 600 nM mannitol, or any amount therebetween. The concentration of osmoticum may also be expressed as a percentage (w/v). For some plant or tissue types, it may be beneficial to employ a slightly hypertonic preparation, which may facilitate separation of plant cell plasma membrane from the cell wall. The osmoticum can also be omitted during the step of cell wall loosening.

Chemical compositions and compounds useful for modifying and thereby loosening the cell wall comprise for example but are not limited to chelators, divalent chelators, hydroxyl radicals, indole-3-acetic acid and expansins. Examples of a chelators include, for example but are not limited to, ethylenediamine tetraacetic acid (EDTA) and ethylene glycol tetraacetic acid (EGTA). The chelators may be present at a concentration from 0 mM to about 500 mM, or any amount therebetween, for example 10, 20, 30, 40, 50, 60, 70, 80, 90, 100, 110, 120, 130, 140, 150, 160, 170, 180, 190, 200, 250, 300, 350, 400, 450, 500 mM or any amount therebetween. The one or more than one chelator may be combined with an additional chemical compound, an enzymatic solution or a combination of an additional chemical compound, an enzymatic solution, to provide a cell wall loosening composition. Examples for expansins include, for example but are not limited to expansin A, expansin B, expansin like A, expansin like B and expansin like X. Expansin may be used in a concentration ranging from 0.1% to 5%, for example 0.1, 0.25, 0.5, 0.75, 1.0, 1.25, 1.5, 1.75, 2.0, 2.25, 2.5, 2.75. 3.0. 3.25, 3.5, 3.75, 4.0, 4.25, 4.5, 4.75, 5.0% (w/v). The one or more than one expansin may be combined with an enzymatic solution to provide a cell wall loosening composition.

The cell wall might be loosened by non-enzymatic cleave of wall polymers. Example for such non-enzymatic cleavage include the cleavage by hydroxyl radicals. Hydroxyl radicals may be produced by the reduction of $H_2O_2$ with for example ascorbate in the presence of an catalytic amount of Cu or Fe ions (Fenton's reagent). Methods and techniques relating to hydroxyl radical-induced cell-wall loosening are reviewed in, for example, Schopf, Peter (The Plant Journal, 2001, 28(6), 679-688, which is incorporated herein by reference).

Alternatively, the cell wall might be loosened by indole-3-acetic acid (auxin) adding from about 0 to about 200 µM, or any amount therebetween, for example 5, 10, 15, 20, 25, 50, 75, 100, 125, 150, 175, 200 µM, or any amount therebetween. Indole-3-acetic acid may be combined with an enzymatic solution to provide a cell wall loosening composition.

The cell wall might further be loosened by a physical treatment of the plant cells such as sonication. A variety of ultrasonic baths are commercially available and may be used with the present invention. The term ultrasonic refers to frequencies just above the range of human hearing, hence about 20 kHz. Alternatively, ultrasonic energy can be delivered directly to the solution or suspension of cells through, for example, a transducer. A solution or suspension of cells can be placed in, for example, a vessel or well or a series of vessels or wells comprising a medium capable of transmitting ultrasonic energy. A non-limiting example of a medium is a cell wall loosening composition. The well is either attached to or is in proximity to a suitable transducer or other device capable of translating input energy into ultrasonic energy. The cells can be placed directly into the well or series of wells which act as sample holders, or, alternatively the cells can be placed in containers and submerged in liquid contained within the well. The well can be capped with a suitable closure to prevent leakage or aerosolization. A range of sonication frequencies are suitable for sonication of the plant sample, ultrasonic energy ranging from about 5 KHZ to about 60 KHZ or any amount therebetween, for example 10, 15, 20, 25, 30, 35, 40, 45, 50, 55 KHZ may be used. Sonication may proceed from about 5 seconds to about 10 minutes or any time therebetween.

Another parameter that may be adjusted to assist in loosening of the cell wall is temperature. Temperature may be controlled during the cell wall loosening step. Useful temperature range is between 4° C. and 40° C. or any temperature therebetween, for example from about 4° C. to about 15° C., or any amount therebetween, or from about 4° C. to about 22° C., or any temperature therebetween. Depending to the temperature chosen, the other cell wall loosening experimental parameters may be adjusted to maintain optimal extraction conditions.

Cations, salts or both may be added to improve plasma membrane stability, for example divalent cations, such as $Ca^{2+}$, or $Mg^{2+}$, at 0.5-50 mM, or any amount therebetween, salts, for example $CaCl_2$, NaCl, $CuSO_4$, $KNO_3$, and the like, from about 0 to about 750 mM, or any amount therebetween, for example 10, 20, 30, 40, 50, 100, 200, 300, 400, 500, 600, 700 or 750 mM. Other additives may also be added including a chelator for example, but not limited to, EDTA, EGTA, from about 0 to about 200 mM, or any amount therebetween, for example 5, 10, 15, 20, 25, 50, 75, 100, 125, 150, 175, 200 mM, or any amount therebetween, a reducing agent to prevent oxidation such as, but not limited to, sodium bisulfite or ascorbic acid, at 0.005-0.4% or any amount therebetween, for example 0.01, 0.02, 0.03, 0.04, 0.05, 0.06, 0.07, 0.08, 0.09, 0.1, 0.15, 0.2, 0.25, 0.3, 0.35, 0.4%, or any amount therebetween, specific enzyme inhibitors (see below), and if desired, an inhibitor of foliar senescence, for example, cycloheximide, kinetin, or one or more polyamines.

The cell wall loosening composition may also comprise one or more osmoticum, for example mannitol from about 0 to about 600 mM, NaCl from about 0 to about 500 mM, EDTA from about 0 to about 50 mM, cellulase from about 1% to about 2% v/v, pectinase from about 0 to about 1% v/v, sodium metabisulfite from about 0.03 to about 0.04%, citrate from about 0 to about 125 mM or NaPO4 from about 0 to 75 mM. However, as the method described herein loosens the cell wall, rather than completely digesting the cell wall, the use of an osmoticum in the cell wall loosening composition is optional.

The plant matter may be treated to enhance access of the enzymes or enzyme composition to the plant cell wall. For example, the epidermis of the leaf may be removed or 'peeled' before treatment with an enzyme composition. The plant matter may be cut into small pieces (manually, or with a shredding or cutting device such as an Urschel slicer); the cut up plant matter may be further infiltrated with a chemical, enzyme composition, or both chemical and enzyme mixture, under a partial vacuum (Nishimura and Beevers 1978, Plant Physiol 62:40-43; Newell et al., 1998, J. Exp Botany 49:817-827). Mechanical perturbation of the plant matter may also be applied to the plant tissues (Giridhar et al., 1989. Protoplasma 151:151-157) before or during treatment with an enzyme composition. Furthermore, cultured plant cells, either liquid or solid cultures, may be used to prepare a plant preparation comprising loosened cell walls.

It may be desired to use an enzyme composition that lacks, or that has inactivated lipases or proteases. For example, one or more protease, or lipase inhibitors may be included in the enzyme composition. Examples of lipase inhibitors include RHC80267 (SigmaAldrich); examples of protease inhibitors include E-64, Na$_2$EDTA, Pepstatin, aprotinin, PMSF, Pefabloc, Leupeptin, bestatin and the like.

Any suitable method of mixing or agitating the plant matter in the enzyme composition may be used. For example, the plant matter may be gently swirled or shaken in a tray or pan or via a rotary shaker, tumbled in a rotating or oscillating drum.

As a non-limiting example, an enzyme composition comprising 1.5% cellulase (Onozuka R-10) and 0.375% MACEROZYME™ in 500 mM mannitol, 10 m CaCl$_2$ and 5 mM MES (pH 5.6) may be used as a cell wall loosening composition for use with plant tissues, for example, *Nicotiana* tissues. As described herein, the concentration of mannitol may also be varied from about 0 to about 500 mM, or any amount therebetween. One of skill in the art, provided with the information disclosed herein, will be able to determine a suitable enzyme composition for the age and strain of the *Nicotiana* sp, or for another plant species used for the production of VLPs. As another non limiting example, an enzyme composition comprising either one or more pectinase from 1 to 4% (v/v), or any amount therebetween, for example 1.0, 1.2, 1.4, 1.6, 1.8, 2.0, 2.2, 2.4, 2.6, 2.8, 3.0, 3.2, 3.4, 3.6, 3.8, 4.0% (v/v) or any amount therebetween. For example 1 to 4% or any amount therebetween, each of Biocatalysts 162L, Biocatalysts 444L, or a combination thereof, in a 600 mM Mannitol, 75 mM Citrate, 0.04% sodium bisulfite pH 6.0 buffer may be used as a cell wall loosening composition for use with plant tissues, for example, *Nicotiana* tissues. Furthermore, a composition comprising one or more pectinases (for example Biocatalysts 162L, Biocatalysts 444L, or a combination thereof each at 1% to 4% v/v, or any amount therebetween) along with one or more cellulase, from 1% to 4% (v/v) or any amount therebetween, each, for example Multifect CX CG, Multifect CX B (Genencor), or a combination thereof in a 600 mM Mannitol, 75 mM Citrate, 0.04% sodium bisulfite pH 6.0 buffer may be used as a cell wall loosening composition for use with plant tissues, for example, *Nicotiana* tissues.

By "apoplastic content fraction" it is meant a fraction that is obtained following loosening or partial loosening of the cell wall, using a cell wall loosing composition or otherwise modifying the cell wall to loosen the cell wall, for example sonication, or a combination of a cell wall loosing composition and sonication. The apoplastic content fraction may be obtained following incubation of the plant or plant material with a cell wall loosening composition, sonication, or a combination thereof to obtain a plant incubation mixture, and filtering, centrifuging, or a combination thereof, the plant incubation mixture to produce a apoplastic content fraction. The apoplastic content fraction typically comprises soluble components present in the apoplast. The apoplastic content fraction may also comprise some components arising from disruption of the cell wall.

Without wishing to be bound by theory, the step of cell wall loosening may loosen the polymeric components of the cells wall and assist in release of plant proteins, proteins, or suprastructure proteins, otherwise trapped within the cell wall. This protocol also minimizes contamination of the plant proteins, or suprastructure proteins, with the intracellular components. The plant proteins, proteins or suprastructure proteins of interest may be separated from cellular debris following loosening of the cell wall using low speed centrifugation followed by filtration, depth filtration, sedimentation, precipitation for example, but not limited to ammonium sulfate precipitation, or a combination thereof to obtain a apoplastic content fraction comprising the plant proteins, proteins or suprastructure proteins of interest.

Since the method described herein loosens the cell wall, rather than completely digesting the cell wall, an osmoticum may not be needed. If an osmoticum is used, the cell fraction comprising organells, protoplasts and cell wall, may be separated from the apoplastic content fraction using any suitable technique, for example but not limited to, centrifugation, filtration, depth filtration, sedimentation, precipitation, or a combination thereof to obtain a loosened protoplast fraction comprising the plant proteins or suprastructure proteins of interest and/or comprising protoplasts/spheroplasts that comprise the proteins or suprastructure proteins of interest.

The separated fraction may be for example a supernatant (if centrifuged, sedimented, or precipitated), or a filtrate (if filtered), and is enriched for proteins, or suprastructure proteins. The separated fraction may be further processed to isolate, purify, concentrate or a combination thereof, the proteins, or suprastructure proteins, by, for example, additional centrifugation steps, precipitation, chromatographic steps (e.g. size exclusion, ion exchange, affinity chromatography), tangential flow filtration, or a combination thereof. The presence of purified proteins, or suprastructure proteins, may be confirmed by, for example, native or SDS-PAGE, Western analysis using an appropriate detection antibody, capillary electrophoresis, or any other method as would be evident to one of skill in the art.

During synthesis, plant proteins, proteins, or suprastructure proteins of interest, may be secreted outside of the plasma membrane. If the suprastructure protein is a VLP, they are of an average size of about 20 nm to 1 µm, or any amount therebetween. If the suprastructure protein is an antibody, they are of a molecular weight from about 100 kDa to about 1000 kDa, or any amount therebetween. Due to their size, once synthesized, proteins, or suprastructure proteins, may remain trapped between the plasma membrane and cell wall and may be inaccessible for isolation or further purification using standard mechanical methods used to obtain plant proteins. In order to maximize yields, minimize contamination of the suprastructure protein fraction with cellular proteins, maintain the integrity of the proteins, or suprastructure proteins, and, where required, the associated lipid envelope or membrane, methods of loosening the cell wall to release the proteins, or suprastructure proteins, that minimize mechanical damage to the protoplast and/or spheroplasts may be useful, such as the chemical methods, enzymatic methods, or a combination thereof, described herein. However, it is not required that the integrity of all of the protoplasts be retained during the procedure.

A suprastructure protein, for example, a VLP produced in a plant may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol (Mongrand et al., 2004, J. Biol Chem 279:36277-86).

Polypeptide expression may be targeted to any intracellular or extracellular space, organelle or tissue of a plant as desired. In order to localize the expressed polypeptide to a particular location, the nucleic acid encoding the polypeptide may be linked to a nucleic acid sequence encoding a signal peptide or leader sequence. A signal peptide may alternately be referred to as a transit peptide, signal sequence, or leader sequence. Signal peptides or peptide sequences for directing localization of an expressed polypeptide to the apoplast include, but are not limited to, a native (with respect to the protein) signal or leader sequence, or a heterologous signal sequence, for example but not limited to, a rice amylase signal peptide (McCormick 1999, Proc Natl Acad Sci USA 96:703-708), a protein disulfide isomerase signal peptide (PDI) having the amino acid sequence:

```
MAKNVAIFGLLFSLLLLVPSQIFAEE;,    SEQ ID NO. 10
``` a plant pathogenesis related protein (PRP; Szyperski et al. PNAS 95:2262-2262), for example, Tobacco plant pathogenesis related protein 2 (PRP), a human monoclonal antibody signal peptide (SP, or leader sequence), or any signal peptide that is native with respect to the protein.

In some examples, an expressed polypeptide may accumulate in specific intercellular or extracellular space (such as the apoplast), organelle or tissue, for example when the polypeptide is expressed and secreted in the absence of a signal peptide or transit peptide.

The term "virus like particle" (VLP), or "virus-like particles" or "VLPs" refers to structures that self-assemble and comprise viral surface proteins, for example an influenza HA protein, or a chimeric influenza HA protein. VLPs and chimeric VLPs are generally morphologically and antigenically similar to virions produced in an infection, but lack genetic information sufficient to replicate and thus are non-infectious.

By "chimeric protein" or "chimeric polypeptide", it is meant a protein or polypeptide that comprises amino acid sequences from two or more than two sources, for example but not limited to, two or more influenza types or subtypes, that are fused as a single polypeptide. The chimeric protein or polypeptide may include a signal peptide that is the same (i.e. native) as, or heterologous with, the remainder of the polypeptide or protein. The chimeric protein or chimeric polypeptide may be produced as a transcript from a chimeric nucleotide sequence, and remain intact, or if required, the chimeric protein or chimeric polypeptide may be cleaved following synthesis. The intact chimeric protein, or cleaved portions of the chimeric protein, may associate to form a multimeric protein. A chimeric protein or a chimeric polypeptide may also include a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide. A non-limiting example a chimeric protein is a chimeric monoclonal antibody, for example C2B8, or a chimeric VLP, for example but not limited to proteins and VLPs produced constructs numbered 690, 691, 696, 734, 737, 745 or 747 (Table 2) as described in U.S. provisional application 61/220,161 and PCT/CA2010/000983 (which are incorporated herein by reference).

The protein or suprastructure protein maybe a glycoprotein, and the method as described herein involving extraction by cell wall loosening can be applied to plants co-expressing a glycoprotein and one or more enzymes for modifying N-glycosylation profile as described in WO 20008/151440 (*Modifying glycoprotein production in plants*; which is incorporated herein by reference) for favoring the recovery of glycoproteins bearing modified mature N-glycans. For example, mature N-glycans could be exempt of xylose and fucose residues, or exhibit reduced fucosylated, xylosylated, or both, fucosylated and xylosylated, N-glycans. Alternatively, a protein of interest comprising a modified glycosylation pattern may be obtained, wherein the protein lacks fucosylation, xylosylation, or both, and comprises increased galatosylation The modified N-glycosylation profile may be obtained by co-expressing within a plant, a portion of a plant, or a plant cell, a nucleotide sequence encoding a first nucleotide sequence encoding a hybrid protein (GNT1-GalT), comprising a CTS domain (i.e. the cytoplasmic tail, transmembrane domain, stem region) of N-acetylglucosaminyl transferase (GNT1) fused to a catalytic domain of beta-1,4galactosyl-transferase (GalT), the first nucleotide sequence operatively linked with a first regulatory region that is active in the plant, and a second nucleotide sequence for encoding the suprastructure protein of interest, the second nucleotide sequence operatively linked with a second regulatory region that is active in the plant, and co-expressing the first and second nucleotide sequences to synthesize a suprastructure protein of interest comprising glycans with the modified N-glycosylation profile, as described in WO 20008/151440.

The suprastructure protein may be influenza hemagglutinin (HA), and each of the two or more than two amino acid sequences that make up the polypeptide may be obtained from different HA's to produce a chimeric HA, or chimeric influenza HA. A chimeric HA may also include a amino acid sequence comprising heterologous signal peptide (a chimeric HA pre-protein) that is cleaved after synthesis. Examples of HA proteins that may be used in the invention described herein may be found in WO 2009/009876; WO 2009/076778; WO 2010/003225 (which are incorporated herein by reference). A nucleic acid encoding a chimeric polypeptide may be described as a "chimeric nucleic acid", or a "chimeric nucleotide sequence". A virus-like particle comprised of chimeric HA may be described as a "chimeric VLP". Chimeric VLPs are further described in PCT Application No. PCT/CA2010/000983 filed Jun. 25, 2010, and U.S. Provisional Application No. 61/220,161 (filed Jun. 24, 2009; which is incorporated herein by reference). VLPs can be obtained from expression of native or chimeric HA.

The HA of the VLPs prepared according to a method provided by the present invention, include known sequences and variant HA sequences that may be developed or identified. Furthermore, VLPs produced as described herein do not comprise neuraminidase (NA) or other components for example M1 (M protein), M2, NS and the like. However, NA and M1 may be co-expressed with HA should VLPs comprising HA and NA be desired.

Generally, the term "lipid" refers to a fat-soluble (lipophilic), naturally-occurring molecules. A chimeric VLP produced in a plant according to some aspects of the invention may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including phospholipids, tri-, di- and monoglycerides, as well as fat-soluble sterol or metabolites comprising sterols. Examples include phosphatidylcholine (PC), phosphatidylethanolamine (PE), phosphatidylinositol, phosphatidylserine, glycosphingolipids, phytosterols or a combination thereof. A plant-derived lipid may alternately be referred to as a 'plant lipid'. Examples of phytosterols include campesterol, stigmasterol, ergosterol, brassicasterol, delta-7-stigmasterol, delta-7-avenasterol, daunosterol, sitosterol, 24-methylcholesterol, cholesterol or beta-sitosterol (Mongrand et al., 2004, J. Biol Chem 279:36277-86). As one of skill in the art will readily understand, the lipid composition of the plasma membrane of a cell may vary with the culture or growth conditions of the cell or organism, or species, from which the cell is obtained.

Plasma membranes generally comprise lipid bilayers, as well as proteins for various functions. Localized concentrations of particular lipids may be found in the lipid bilayer, referred to as 'lipid rafts'. These lipid raft microdomains may be enriched in sphingolipids and sterols. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

VLPs comprising a lipid envelope has been previously described in WO 2009/009876; WO 2009/076778, and WO 2010/003225 (which are incorporated herein by reference). With reference to influenza virus, the term "hemagglutinin" or "HA" as used herein refers to a structural glycoprotein of influenza viral particles. The HA of the present invention may be obtained from any subtype. For example, the HA may be of subtype H1, H2, H3, H4, H5, H6, H7, H8, H9, H10, H11, H12, H13, H14, H15, or H16, or of influenza types B or C. The recombinant HA of the present invention may also comprise an amino acid sequence based on the sequence of any hemagglutinin. The structure of influenza hemagglutinin is well-studied and demonstrates a high degree of conservation in secondary, tertiary and quaternary structure. This structural conservation is observed even though the amino acid sequence may vary (see, for example, Skehel and Wiley, 2000 Ann Rev Biochem 69:531-69; Vaccaro et al 2005; which is incorporated herein by reference). Nucleotide sequences encoding HA are well known, and are available for example, from the BioDefense and Public Health Database (now Influenza Research Database; Squires et al., 2008 Nucleic Acids Research 36:D497-D503) for example at URL: biohealthbase.org/GSearch/home.do?decorator=Influenza) or the databases maintained by the National Center for Biotechnology Information (NCBI; for example at URL: ncbi.nlm.nih.gov/sites/entrez?db=nuccore&cmd=search&term=influenza), both of which are incorporated herein by reference.

The present invention also pertains to methods of preparing, recovering, isolating, or both preparing, recovering and isolating VLPs, including influenza VLPs of viruses which infect humans, or host animals, for example primates, horses, pigs, birds, sheep, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like. Some influenza viruses may infect more than one host animal. Amino acid variation is tolerated in hemagglutinins of influenza viruses. This variation provides for new strains that are continually being identified. Infectivity between the new strains may vary. However, formation of hemagglutinin trimers, which subsequently form VLPs is maintained. The present invention also includes methods of recovering any plant-derived VLPs, regardless of the HA subtype or sequence, or chimeric HA comprising the VLP, or species of origin.

Correct folding of the suprastructure protein may be important for stability of the protein, formation of multimers, formation and function of the protein. Folding of a protein may be influenced by one or more factors, including, but not limited to, the sequence of the protein, the relative abundance of the protein, the degree of intracellular crowding, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., Cold Spring Harbor Laboratory Res. 25:59-70. 1995; Parsell, D. A. & Lindquist, S. Ann. Rev. Genet. 27:437-496 (1993); U.S. Pat. No. 5,232,833). Chaperone proteins, for example but not limited to Hsp40 and Hsp70 may be used to ensure folding of a chimeric HA (PCT Application No. PCT/CA2010/000983 filed Jun. 25, 2010, and U.S. Provisional Application No. 61/220,161, filed Jun. 24, 2009; WO 2009/009876 and WO 2009/076778, all of which are incorporated herein by reference). Protein disulfide isomerase (PDI; Accession No. Z11499) may also be used.

Once recovered, proteins, or suprastructure proteins, may be assessed for structure, size potency or activity by, for example but not limited to, electron microscopy, light scattering, size exclusion chromatography, HPLC, Western blot analysis, electrophoresis, ELISA, activity based assays, e.g. hemagglutination assay, or any other suitable assay. These and other methods for assessing size, concentration, activity and composition of VLPs are known in the art.

For preparative size exclusion chromatography, a preparation comprising proteins, or suprastructure proteins, may be obtained by the methods described herein, and insoluble material removed by centrifugation. Precipitation with PEG or ammonium sulphate may also be of benefit. The recovered protein may be quantified using conventional methods (for example, Bradford Assay, BCA), and the extract passed through a size exclusion column, using for example SEPHACRYL™, SEPHADEX™, or similar medium, chromatography using an ion exchange column, or chromatography using an affinity column, and the active fractions collected. Protein complexes may also be obtained using affinity based magnetic separation for example, with Dynabeads™ (Invitrogen), and eluting the protein complex from the Dynabeads™. A combination of chromatographic and separation protocols may also be used. Following chromatography, or separation, fractions may be further analyzed by protein electrophoresis, immunoblot, ELISA, activity based assays as desired, to confirm the presence of the suprastructure protein.

If the suprastructure protein is a VLP, then a hemagglutination assay may be used to assess the hemagglutinating activity of the VLP-containing fractions, using methods well-known in the art. Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (Ito T. et al, 1997, Virology, 227:493-499; Medeiros R et al, 2001. Virology 289:74-85).

A hemagglutination inhibition (HI, or HAI) assay may also be used to demonstrate the efficacy of antibodies induced by a vaccine, or vaccine composition comprising chimeric HA or chimeric VLP can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition comprising a chimeric hemagglutinin comprising an HDC of a first influenza type or subtype may be used in an HAI assay with a second strain of whole virus or virus particles, and the HAI titer determined.

The influenza VLPs prepared by methods of the present invention may be used in conjunction with an existing influenza vaccine, to supplement the vaccine, render it more efficacious, or to reduce the administration dosages necessary. As would be known to a person of skill in the art, the vaccine may be directed against one or more than one influenza virus. Examples of suitable vaccines include, but are not limited to, those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like. If desired, the VLPs of the present invention may be admixed with a suitable adjuvant as would be known to one of skill in the art. Furthermore, the VLP produced according to the present invention may be co-expressed with other protein components or reconstituted with other VLPs or influenza protein components, for example, neuraminidase (NA), M1, and M2. It can also be co-expressed or reconstituted with other VLP made of vaccinal proteins such as malaria antigens, HIV antigens, respiratory syncytial virus (RSV) antigens, and the like.

Methods for transformation, and regeneration of transgenic plants, plant cells, plant matter or seeds comprising proteins, or suprastructure proteins, are established in the art and known to one of skill in the art. The method of obtaining transformed and regenerated plants is not critical to the present invention.

By "transformation" it is meant the interspecific transfer of genetic information (nucleotide sequence) that is manifested genotypically, phenotypically or both. The interspecific transfer of genetic information from a chimeric construct to a host may be heritable (i.e. integrated within the genome of the host) and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. A portion of a plant may comprise plant matter. Plants or plant matter may be harvested or obtained by any method, for example, the whole plant may be used, or the leaves or other tissues specifically removed for use in the described methods. Transgenic plants expressing and secreting VLPs may also be used as a starting material for processing as described herein.

The constructs of the present invention can be introduced into plant cells using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, Fundamentals of Gene Transfer in Plants. In *Plant Metabolism*, 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625, 136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described in PCT Publications WO 00/063400, WO 00/037663 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

The sequences described herein are summarized below.

| SEQ ID NO: | Description | Figure |
|---|---|---|
| 1 | Nucleic acid sequence (construct 685) | 2A |
| 2 | Amino acid sequence encoded by SEQ ID NO: 1 | 2B |
| 3 | pBinPlus.2613c: AGGAAGGGAAGAAAGCGAAAGGAG | |
| 4 | Mut-ATG115.r: GTGCCGAAGCACGATCTGACAACGT TGAAGATCGCTCACGCAAGAAAGACAAGAGA | |
| 5 | Mut-ATG161.c: GTTGTCAGATCGTGCTTCGGCACCAGTACAA CGTTTTCTTTCACTGAAGCGA | |
| 6 | LC-05-1.110r: TCTCCTGGAGTCACAGACAGGGTGG | |
| 7 | ApaI-H5 (A-Indo).1c: TGTCGGGCCCATGGAGAAAATAGTGC TTCTTCTTGCAAT | |
| 8 | H5 (A-Indo)-StuI.1707r: AAATAGGCCTTTAAATGCAAATTC TGCATTGTAACGA | |
| 9 | nucleic acid sequence (construct 660) | 5 |
| 10 | PDI signal peptide: MAKNVAIFGLLFSLLLLVPSQIFAEE | |
| 11 | Plasto-443c | |
| 12 | supP19-plasto.r | |
| 13 | supP19-1c | |
| 14 | SupP19-SacI.r | |
| 15 | LC fragment of C2B8 | 9 |
| 16 | HC fragment of C2B8 | 10 |

The present invention will be further illustrated in the following examples. However it is to be understood that these examples are for illustrative purposes only, and should not be used to limit the scope of the present invention in any manner.

EXAMPLES

Assembly of Expression Cassettes

Constructs that may be used for the production of VLPs are described U.S. Provisional Application No. 61/220,161 and PCT/CA2010/000983 (which are incorporated herein by reference), WO 2009/009876, WO 2009/076778 and WO2010/003225 (all of which are incorporated herein by reference). Constructs may also include those listed in Table 2. Assembly of these constructs is described in WO 2009/009876, WO 2009/076778, WO2010/003225 and U.S. 61/220,161. However other constructs comprising known HA's, including but not limited to, those provided in Table 2, and combined with similar or different regulatory elements and promoters, may also be used for the production of VLPs as described herein.

TABLE 2

Non-limiting examples of constructs that can be used for hemagglutinin production.

| Cassette number | Corresponding HA | HA abbreviation |
|---|---|---|
| 540 | SpPDI-H1 from strain A/New Caledonia/20/99 (H1N1) | H1/NC |
| 560 | SpPDI-H1 A/California/4/2009 in 2X35S/CPMV-HT expression cassette | H1/Cal WT |
| 580 | SpPDI-H1 A/New Caledonia/20/99 in 2x35S/CPMV-HT expression cassette | H1/NC |
| 660 | H5 from strain A/Indonesia/5/2005 (H5N1) | H1/Indo |
| 663 | H5 A/Indonesia/5/2005 | H1/Indo |
| 685 | H5 A/Indonesia/5/2005 in CPMV-HT expression cassette | H1/Indo |
| 686 | SpPDI-H5 A/Indonesia/5/2005 in CPMV-HT expression cassette | H1/Indo |
| 690 | H1 A/Brisbane/59/07 receptor-binding (RB) domain in H5 A/Indonesia/5/05 backbone | H1/Bris |
| 691 | H1 A/Brisbane/59/07 esterase and receptor-binding domains (E1-RB-E2) in H5 A/Indonesia/5/05 backbone | H1/Bris |
| 696 | H5 A/Indonesia/5/05 receptor-binding (RB) domain in H1 A/New Caledonia/20/99 backbone | H1/Indo |
| 732 | H1 A/Brisbane/59/2007 in CPMV-HT expression cassette | H1/Bris |
| 733 | SpPDI-H1 A/Brisbane/59/2007 in CPMV-HT expression cassette | H1/Bris |
| 734 | H1 A/Brisbane/59/2007 receptor-binding (RB) domain in H5 A/Indonesia/5/05 backbone in CPMV-HT expression cassette | H1/Bris |
| 735 | H3 A/Brisbane/10/2007 in CPMV-HT expression cassette | H3/Bris |
| 736 | SpPDI-H3 A/Brisbane/10/2007 in CPMV-HT expression cassette | H3/Bris |
| 737 | Assembly of chimeric SpPDI-H3 A/Brisbane/10/2007 (ectodomain) + H5 A/Indonesia/5/2005 (TmD + Cyto tail) in CPMV-HT expression cassette | H3/Bris-H5/Indo chimera |
| 738 | HA B/Florida/4/2006 in CPMV-HT expression cassette | B/Flo |
| 739 | SpPDI-HA B/Florida/4/2006 in CPMV-HT expression cassette | B/Flo |

TABLE 2-continued

Non-limiting examples of constructs that can be used for hemagglutinin production.

| Cassette number | Corresponding HA | HA abbreviation |
|---|---|---|
| 745 | SpPDI-HA B/Florida/4/2006 (ectodomain) + H5 A/Indonesia/5/2005 (TmD + Cyto tail) in CPMV-HT expression cassette | B/Flo |
| 747 | SpPDI-HA B/Florida/4/2006 + H5 A/Indonesia/5/2005 (TmD + Cyto tail) in 2X35S-CPMV-HT expression cassette | B/Flo |
| 774 | HA of A/Brisbane/59/2007 (H1N1) | H1/Bris |
| 775 | HA of A/Solomon Islands 3/2006 (H1N1) | H1/Solomon |
| 776 | HA of A/Brisbane 10/2007 (H3N2) | H3/Bris |
| 777 | HA of A/Wisconsin/67/2005 (H3N2) | H3/Wisc |
| 778 | HA of B/Malaysia/2506/2004 | B/Malaysia |
| 779 | HA of B/Florida/4/2006 | B/Flo |
| 780 | HA of A/Singapore/1/57 (H2N2) | H2/Sing |
| 781 | HA of A/Anhui/1/2005 (H5N1) | H5/Anhui |
| 782 | HA of A/Vietnam/1194/2004 (H5N1) | H5/Vietnam |
| 783 | HA of A/Teal/HongKong/W312/97 (H6N1) | H6/HongKong |
| 784 | HA of A/Equine/Prague/56 (H7N7) | H7/Prague |
| 785 | HA of A/HongKong/1073/99 (H9N2) | H9/HongKong |
| 787 | H1 A/Brisbane/59/2007 | H1/Bris |
| 790 | H3 A/Brisbane/10/2007 | H3/Bris |
| 798 | HA B/Florida/4/2006 | B/Flo |

CPMV-HT expression cassettes included the 35S promoter to control the expression of an mRNA comprising a coding sequence of interest flanked, in 5' by nucleotides 1-512 from the Cowpea mosaic virus (CPMV) RNA2 with mutated ATG at positions 115 and 161 and in 3', by nucleotides 3330-3481 from the CPMV RNA2 (corresponding to the 3' UTR) followed by the NOS terminator. Plasmid pBD-C5-1LC, (Sainsbury et al. 2008; Plant Biotechnology Journal 6: 82-92 and PCT Publication WO 2007/135480), was used for the assembly of CPMV-HT-based hemagglutinin expression cassettes. The mutation of ATGs at position 115 and 161 of the CPMV RNA2 was done using a PCR-based ligation method presented in Darveau et al. (Methods in Neuroscience 26: 77-85 (1995)). Two separate PCRs were performed using pBD-C5-1LC as template. The primers for the first amplification were pBinPlus.2613c (SEQ ID NO: 3) and Mut-ATG115.r (SEQ ID NO: 4). The primers for the second amplification were Mut-ATG161.c (SEQ ID NO: 5) and LC-C5-1.110r (SEQ ID NO: 6). The two fragments were then mixed and used as template for a third amplification using pBinPlus.2613c (SEQ ID NO: 3) and LC-C5-1.110r (SEQ ID NO: 6) as primers. The resulting fragment was digested with PacI and ApaI and cloned into pBD-C5-1LC digested with the same enzyme. The expression cassette generated was named 828.

Assembly of H5 A/Indonesia/5/2005 in CPMV-HT Expression Cassette (Construct Number 685).

The assembly of this cassette is described in WO 2009/009876, WO 2009/076778 and WO2010/003325, which are incorporated herein by reference.

Briefly, the coding sequence of H5 from A/Indonesia/5/2005 was cloned into CPMV-HT as follows: restriction sites ApaI (immediately upstream of the initial ATG) and StuI (immediately downstream of a stop codon) were added to the hemagglutinin coding sequence by performing a PCR amplification with primers ApaI-H5 (A-Indo). 1c (SEQ ID NO: 7) and H5 (A-Indo)-StuI.1707r (SEQ ID NO: 8) using construct number 660 (D'Aoust et al., Plant Biotechnology Journal 6:930-940 (2008)) as template. Construct 660 comprises an alfalfa plastocyanin promoter and 5' UTR, hemagglutinin coding sequence of H5 from A/Indonesia/5/2005 (Construct #660), alfalfa plastocyanin 3' UTR and terminator sequences (SEQ ID NO: 9; FIG. 5). The resulting fragment was digested with ApaI and StuI restriction enzymes and cloned into construct number 828, previously digested with the same enzymes. The resulting cassette was named construct number 685 (FIG. 1, 2).

Suppressors of Silencing.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

The construction of p19 is described in described in WO 2010/0003225 (which is incorporated herein by reference). Briefly, the coding sequence of p19 protein of tomato bushy stunt virus (TBSV) was linked to the alfalfa plastocyanin expression cassette by the PCR-based ligation method presented in Darveau et al. (Methods in Neuroscience 26: 77-85 (1995)). In a first round of PCR, a segment of the plastocyanin promoter was amplified using primers Plasto-443c:

GTATTAGTAATTAGAATTTGGTGTC (SEQ ID NO: 11)

and supP19-plasto.r (SEQ ID NO: 12)
CCTTGTATAGCTCGTTCCATTTTCTCTCAAGATG with construct 660 (described in WO 2010/0003225, which is incorporated herein by reference) as template. In parallel, another fragment containing the coding sequence of p19 was amplified with primers supP19-1c

ATGGAACGAGCTATACAAGG (SEQ ID NO: 13)

and SupP19-SacI.r (SEQ ID NO: 14)
AGTCGAGCTCTTACTCGCTTTCTTTTTCGAAG using construct 35S:p19 as described in Voinnet et al. (The Plant Journal 33: 949-956 (2003)) as template. Amplification products were then mixed and used as template for a second round of amplification (assembling reaction) with primers Plasto-443c and SupP19-SacI.r. The resulting fragment was digested with BamHI (in the plastocyanin promoter) and SacI (at the end of the p19 coding sequence) and cloned into construct number 660, previously digested with the same restriction enzymes to give construct number R472. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping. The *A. tumefaciens* strain comprising R472 (FIG. 11B) is termed "AGL1/R472".

HcPro construct (35HcPro) was prepared as described in Hamilton et al. (2002). All clones were sequenced to confirm the integrity of the constructs. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping.

Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. After six weeks, plants have an average weight of 80 g and 30 cm in height.

*Agrobacterium* strain AGL1 was transfected (electroporation) with constructs as identified below, using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 µM acetosyringone, 50 µg/ml kanamycin and 25 µg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Plants were agroinfiltrated as described in D'Aoust et al (supra). Briefly, for vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Unless otherwise specified, all infiltrations were performed as co-infiltration with a bacterial transformed with R472 (strain AGL1/R472) at a 1:1 ratio. Following vacuum infiltration, plants were returned to the greenhouse for a 4-6 day incubation period until harvest.

Leaf Sampling and Total Protein Extraction (Mechanical Homogenization)

Following incubation of 4, 5, 6, 7 and 8 days, the aerial part of plants was harvested and used immediately. Total soluble proteins were extracted by homogenizing plant tissue in 3 volumes of cold 50 mM Tris pH 8.0, 0.15 M NaCl containing 1% Triton X-100 and 0.004% sodium metabisulfite. Plant tissue were mechanically homogenized using a POLYTRON™, grinding with mortar and pestle, or with a COMITROL™ in 1 volume of cold 50 mM Tris pH 8, 0.15 M NaCl. The buffer used with the COMITROL™ also contained 0.04% sodium metabisulfite. Following homogenization, the slurry of ground plant material was centrifuged at 5,000 g for 5 min at 4° C. and the crude extracts (supernatant) kept for analysis. The total protein content of clarified crude extracts was determined by the Bradford assay (Bio-Rad, Hercules, Calif.) using bovine serum albumin as the reference standard.

VLP Extraction by Cell Wall Digestion

Leaf tissue was collected from the *Nicotiana benthamiana* plants and cut into ~1 $cm^2$ pieces. The leaf pieces were soaked in 500 mM mannitol for 30 minutes at room temperature (RT). The mannitol solution was then removed and changed with the enzyme mix (mixture of cellulases from *Trichoderma viride* (Onozuka R-10; 3% v/v) and a mixture of pectinases from *Rhizopus* sp. (MACEROZYME™; 0.75% v/v; both from Yakult Pharmaceuticals) in protoplasting solution (500 mM mannitol, 10 mM $CaCl_2$ and 5 mM MES/KOH (pH 5.6)). The ratio used was 20 g of leaf pieces per 100 mL solution. This preparation was spread evenly into a shallow vessel (~11×18 cm) and incubated for 16 hours on a rotary shaker at 40 rpm and 26° C.

Alternately, VLP extraction may be performed as follows: plants were agroinfiltrated with AGL1/#685 as described in example 1. Leaf tissue was collected from the *N. benthamiana* plants at day 6 post-infiltration and cut into ~1 $cm^2$ pieces. Multifect Pectinase FE, Multifect CX CG and Multifect CX B (Genencor) were added to 1.0% each (v/v) in a 600 mM Mannitol, 75 mM Citrate, 0.04% sodium bisulfite pH 6.0 buffer using a ratio of 1:2.5 (w/v) fresh biomass; digestion buffer. The biomass was digested for 15 h at room temperature in a orbital shaker.

Following incubation, leaf debris was removed by filtration (nylon filter of 250 or 400 µm mesh). Protoplasts in suspension were collected by centrifugation at 200×g (15 min), followed by centrifugation of the supernatant at 5000×g (15 min) to further clarify the supernatant. Alternately, a single centrifugation step at 5000×g for 15 minutes may be employed. Seventy mL of the supernatant was then centrifuged at 70,000×g for 30 minutes. The resulting pellet was resuspended in 1.7 mL of PBS and analyzed immediately or frozen.

Protein Analysis

A hemagglutination assay for H5 was based on a method described by Nayak and Reichl (2004). Briefly, serial double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as hemagglutination activity. In parallel, a recombinant HA5 standard (A/Vietnam/1203/2004 $H_5N_1$) (Protein Science Corporation, Meriden, Conn.) was diluted in PBS and run as a control on each plate.

ELISA

HA5 standard was prepared with purified virus-like particles which were disrupted by treatment with 1% Triton X-100 followed by mechanical agitation in a Tissue Lyser™ (Qiagen) for 1 min. U-bottom 96-well microtiter plates were coated with 10 µg/mL of capture antibody (Immune Technology Corporation, #IT-003-005I) in 50 mM carbonate-bicarbonate coating buffer (pH 9.6) for 16-18 hours at 4° C. All washes were performed with 0.01 M PBS (phosphate-buffered saline), pH 7.4 containing 0.1% Tween-20. After incubation, plates were washed three times and blocked with 1% casein in PBS for 1 hour at 37° C. After the blocking step, plates were washed three times. The HA5 standard was diluted in a mock extract (prepared from leaf tissue infiltrated with AGL1/R472 alone) to generate a standard curve from 500 to 50 ng/mL. Samples to quantify were treated in 1% Triton X-100 prior to loading the microplate. Plates were further incubated for 1 hour at 37° C. After washing, sheep polyclonal antibody raised against HA5 (CBER/FDA) diluted 1:1000 was added and the plates were incubated for 1 hour at 37° C. After washing, horseradish peroxidase-conjugated rabbit anti-sheep antibody diluted 1:1000 was added and the plates were incubated for 1 hour at 37° C. After the final washes, the plates were incubated with SureBlue TMB peroxidase substrate (KPL) for 20 minutes at room temperature. Reaction was stopped by the addition of 1N HCl and $A_{450}$ values were measured using a Multiskan Ascent plate reader (Thermo Scientific).

Example 1: Enzymatic Extraction of Plant Tissue High Quantities of HA Having an Elevated Relative Activity The quantity and relative activity of HA obtained from the present enzymatic extraction method were compared with that of HA obtained from common mechanical extraction methods. N. benthamiana plants were infiltrated with AGL1/685 and the leaves were harvested after a five to six-day incubation period. Leaf homogenates were prepared as follows: Two grams of leaves were homogenized with a Polytron homogenizer; 4 g of leaves were ground with a mortar and a pestle; and 25 kg of leaves were homogenized with a COMITROL™ processor (Urschel Laboratories) in an extraction buffer (50 mM Tris, 150 mM NaCl pH 8.0, ratio of 1:1 w/v). Enzymatic extraction was carried as follow: Twenty grams of harvested leaves were subjected to digestion with Macerozyme pectinases and Onozuka R-10 cellulases as described above. Following digestion, leaf debris were removed by filtration (nylon filter, 250 µm mesh). Protoplasts in suspension were removed by centrifugation at 200×g (15 min), and the supernatant further clarified by centrifugation at 5000×g (15 min).

The relative activity and quantity of HA in each of these plant extracts is shown in Table 3. The amount of HA released by enzymatic digestion of the cell wall is significantly superior when compared to the other techniques used.

TABLE 3

HA-VLP recovered form plant extract generated by different mechanical or enzymatic methods. For activity-based and ELISA comparisons, data was normalized according to the relative volume of liquid extract of fresh biomass. The protein obtained using Comitrol extraction was set at 100%, and the other methods compared to this value.

| Extraction method | Relative activity | Quantity* |
|---|---|---|
| Comitrol ™ extract | 100% | 100% |
| Polytron extract | 50% | 150% |
| Mortar extract | 100% | 220% |
| Digestion extract | 440% | 570% |

*Quantity was evaluated by ELISA analysis

Example 2: Enzymatic Digestion of Plant Tissue Releases HA Organized into VLPs

A combination of differential centrifugation and size exclusion chromatography (SEC) was used to demonstrate that the HA obtained by the enzymatic extraction method described herein were organized as VLPs. N. benthamiana plants were agroinfiltrated with AGL1/685 as described in Example 1. Leaves were collected from the plants 6 days post-infiltration and cut into ~1 cm² pieces then digested, coarse-filtered and centrifuged as described in Example 1.

The clarified samples were then centrifuged at 70,000×g to allow for segregation of VLPs. The centrifugation pellet, containing the VLPs, was gently resuspended in 1/50 volume of Phosphate buffered saline (PBS; 0.1M sodium phosphate, 0.15M NaCl pH 7.2) before being loaded on a SEC column.

SEC columns of 32 ml SEPHACRYL™ S-500 high resolution beads (S-500 HR: GE Healthcare, Uppsala, Sweden, Cat. No. 17-0613-10) were prepared with equilibration/elution buffer (50 mM Tris, 150 mM NaCl, pH8). SEC chromatography was performed with the loading of a 1.5 mL VLP sample onto the equilibrated column, and its elution with 45 mL of equilibration/elution buffer. The eluate was collected in fractions of 1.7 mL, and the protein content of each fraction was evaluated by mixing 10 µL of the eluate fraction with 200 µL of diluted Bio-Rad protein dye reagent (Bio-Rad, Hercules, Calif.). Each separation was preceded by a calibration with Blue Dextran 2000 (GE Healthcare Bio-Science Corp., Piscataway, N.J., USA). Comparison of the elution profiles of both Blue Dextran 2000 and host proteins was performed for each separation to ensure uniformity of the separations.

Protein Analysis of the SEC Eluted Fractions

Total protein content of clarified crude extracts was determined by the Bradford assay (Bio-Rad, Hercules, Calif.) using bovine serum albumin as the reference standard. Proteins present in SEC eluate fractions were precipitated with acetone (Bollag et al., 1996), resuspended in either 0.25 volume or 0.05 volume of denaturing sample loading buffer (0.1M Tris pH 6.8, 0.05% bromophenol blue, 12.5% glycerol, 4% SDS and 5% beta-mercaptoethanol) for SDS-PAGE analysis or immunoblot analysis, respectively. Separation by SDS-PAGE was performed under reducing conditions, and Coomassie Brillant Blue R-250 was used for protein staining.

Hemagglutination assay for H5 was performed based on a method described by Nayak and Reichl (2004). Briefly, successive double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as hemagglutination activity. In parallel, a recombinant H5 standard (A/Vietnam/1203/2004 H5N1) (Protein Science Corporation, Meriden, Conn.) was diluted in PBS and run as a control on each plate.

Figure 3A:
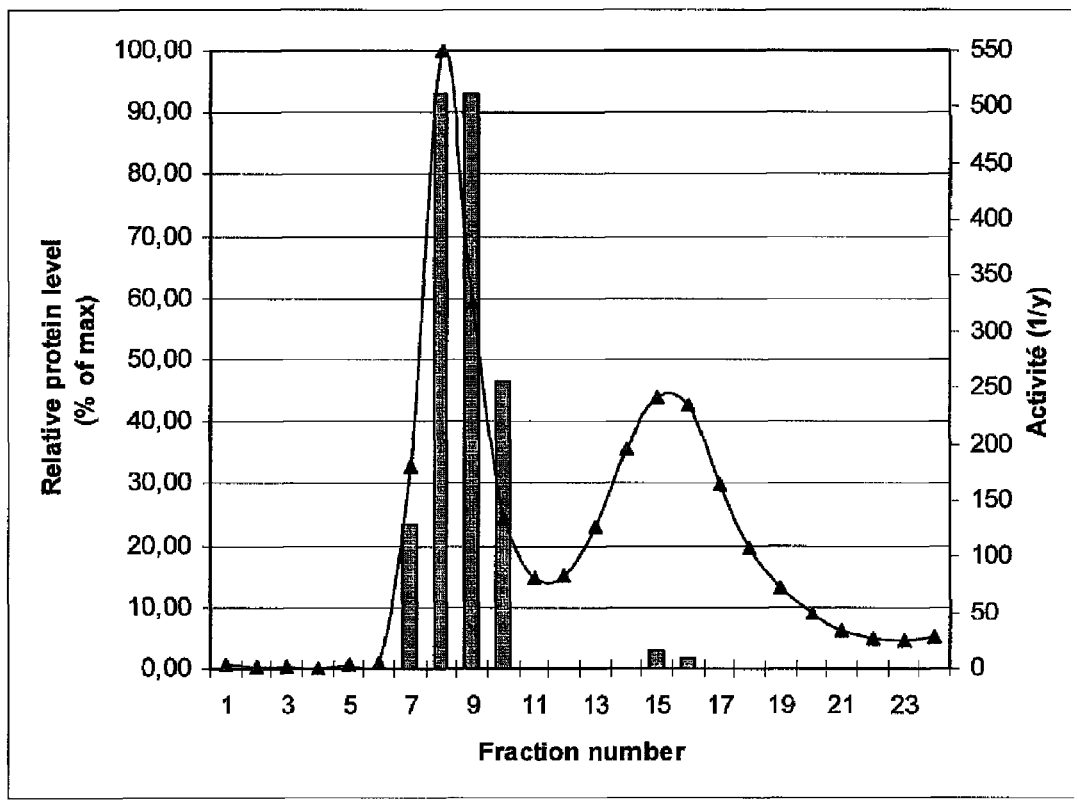
FIG. 3A shows the total soluble protein content per fraction (solid triangles; % of maximum, left-side Y-axis; determined using the Bradford method). The hemagglutinating activity of the collected fractions (solid bars; right-side Y axis) is also shown.
Figure 3B:
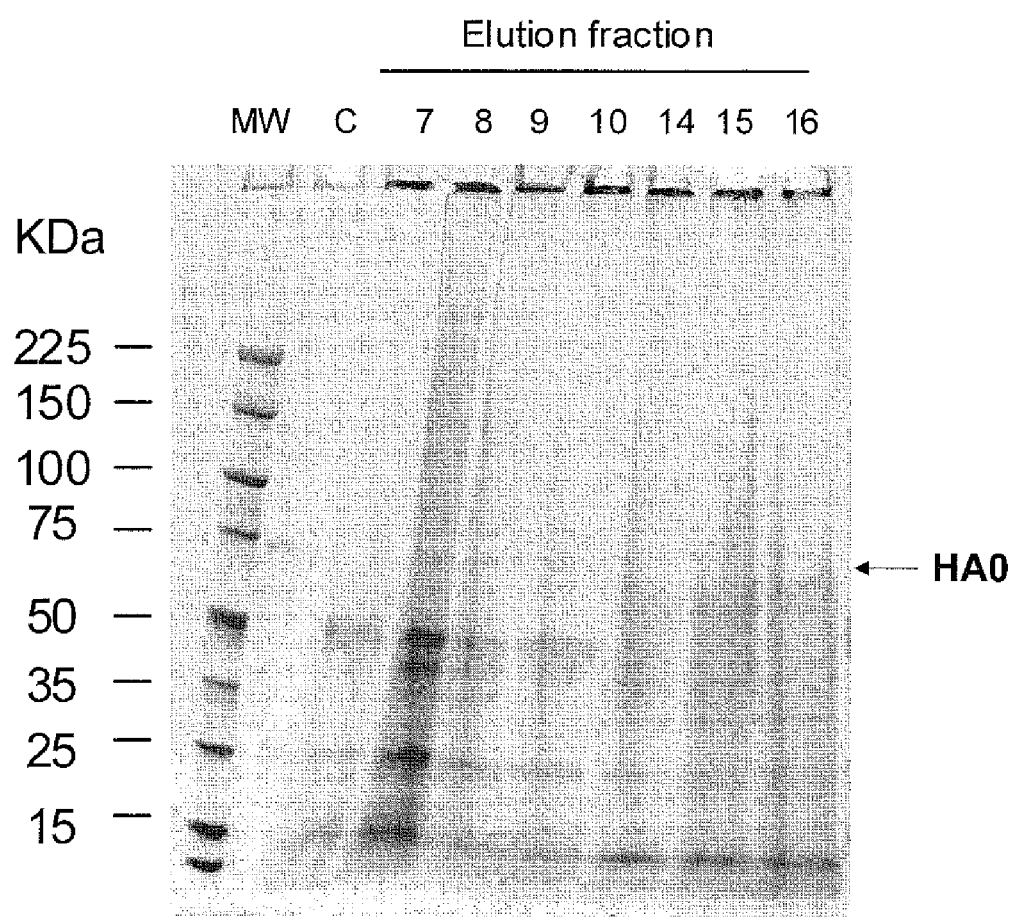
FIG. 3B shows SDS-PAGE analysis of SEC eluted fractions. Fractions were precipitated by acetone and re-suspended in 1/40 volume of reducing sample loading buffer prior to analysis. Gel was stained with 0.1% Coomassie R-250 solution. Purified VLPs were run as a control. The band corresponding to the HA0 monomer is indicated by an arrow. MW—Molecular weight standards (kDa); C—Purified VLPs (control); lanes 7 through 10 and 14 through 16 correspond to fractions number eluted from SEC analysis, shown in FIG. 3A.

FIG. 3A shows that the hemagglutination activity is concentrated in the fractions corresponding to the void volume of the column, confirming that the hemagglutination activity originates from a high molecular weight structural organization. SDS-PAGE analysis (FIG. 3B) revealed that those same void volume fractions (fractions 7-10) also present the highest HA content, with a band corresponding to the HA0 monomer being detectable at approximately 75 kDa.

Example 3: Enzymatic Digestion of Plant Tissue Releases HA-VLPs with Fewer Contaminants N. benthamiana plants were agroinfiltrated with AGL1/685 as described in Example 1. Leaves were collected on day 6 post-infiltration, cut into ~1 cm² pieces, digested, coarse-filtered and centrifuged as described in Example 1.

The controlled enzymatic digestion of the leaves removed the cell walls, at least partially, thus allowing for the release of proteins and components presents in the space between the cell wall and the plasma membrane into the extraction medium. Since most intracellular proteins and components were still undamaged and contained within the mostly intact protoplasts, an initial centrifugation step allowed for their removal, thus providing a resulting solution comprising cell wall degrading enzymes, in addition of the extracellular plant proteins and components (apoplastic content fraction), as shown in FIG. 4.

Figure 4:
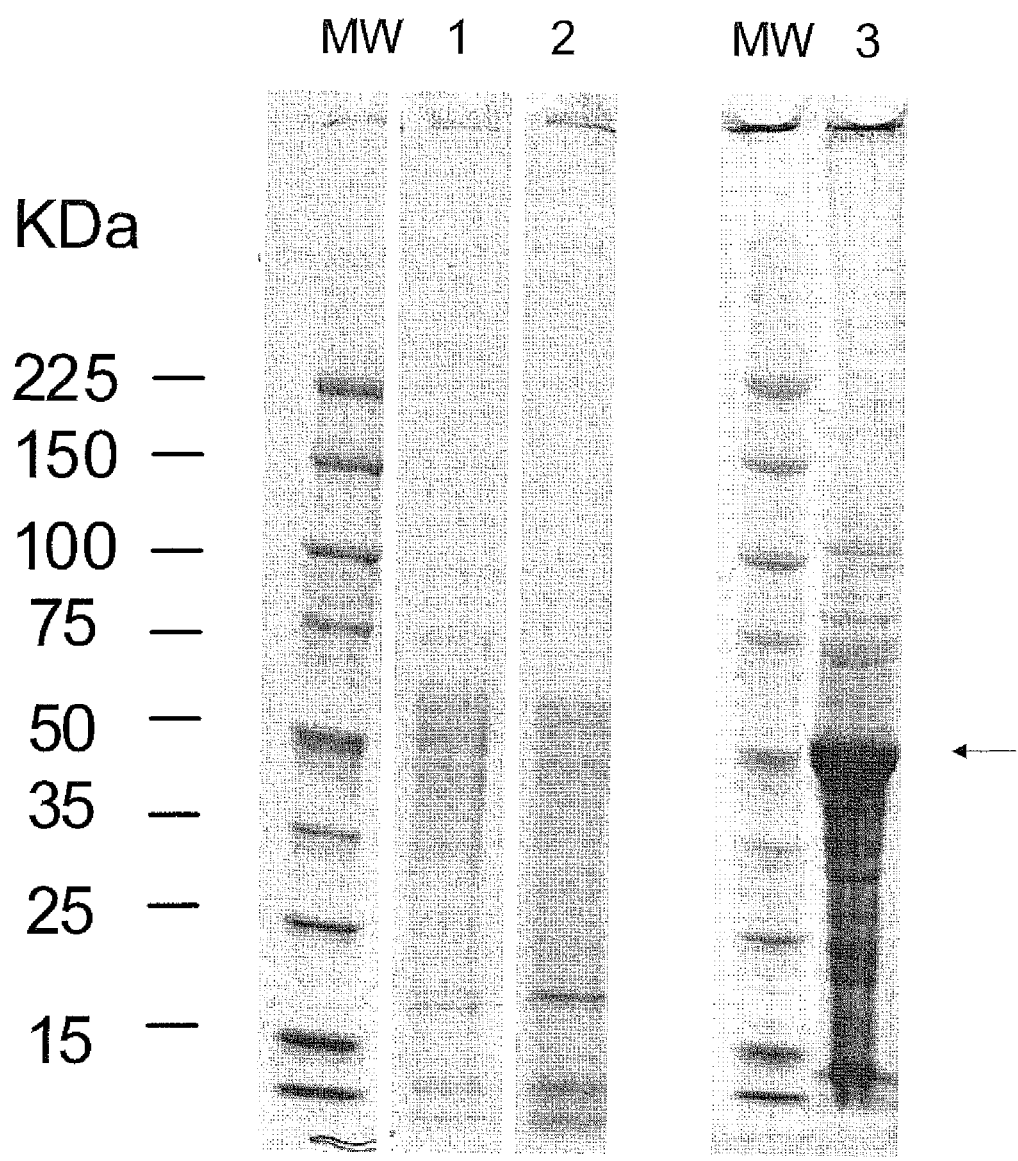
FIG. 4 shows a comparison of protein profiles obtained after enzymatic digestion and by mechanical homogenization using a Comitrol™ homogenizer. Samples were treated in denaturing sample loading buffer and proteins were separated by SDS-PAGE analysis of elution fractions. Gels were stained with 0.1% Coomassie R-250 solution. MW—Molecular weight standards (kDa); lane 1-25 μl enzyme mixture; lane 2-25 μl enzymatic digestion of plant tissue and lane 3-5 μl extract obtained with the Comitrol homogenizer.

FIG. 4 shows a SDS-PAGE analysis of the resulting solution obtained following the controlled enzymatic digestion of leaves tissue as described previously, with lane 1 showing the enzyme mixture used and lane 2 showing the resulting solution following the enzymatic digestion. The protein content of a crude extract from Comitrol™ is provided on lane 3 for comparison. The biomass:buffer ratio for the extract presented in lane 2 was 1:5 (w/v) while it was 1:1 (w/v) for that in lane 3. Each of lanes 2 and 3 therefore contain proteins derived from an equivalent quantity of starting material. For approximately the same buffer:plant ratio, a mechanical plant extract contained a protein concentration of approximately 3.5-4 mg/ml, while the enzymatic plant extract obtained according to the present method presented a protein concentration of approximately 1 mg/ml.

The major contaminant present in lane 3 was found to be RubisCo (Ribulose-1,5-bisphosphate carboxylase oxygenase), which is made of two types of protein subunits: a large-chain (L, about 55 kDa) and a small-chain (S, about 13 kDa). A total of eight large-chain dimers and eight small-chains usually assemble with each other into a RubisCo 540 kDa larger complex. While this plant protein contaminant is found in large amount in plant extracts originating from mechanical extraction method (see arrow in FIG. 4), it is virtually absent in plant extracts obtained by the enzymatic digestion method described herein. Therefore, the present method allows for the elimination of this major plant protein contaminant, amongst others, at an early stage of the process.

Example 4: Enzymatic Digestion of Plant Tissue Releases HA-VLP in Conditions where it can be Directly Captured on a Cation Exchange Resin N. benthamiana plants were agroinfiltrated with AGL1/685 as described in Example 1. Leaves were collected on day 6 post-infiltration, cut into ~1 cm² pieces and digested for 15 h at room temperature in an orbital shaker. The digestion buffer contained 1.0% (v/v) Multifect Pectinase FE, 1.0% (v/v) Multifect CX CG orand 1.0% (v/v) Multifect CX B (all from Genencor), each in a solution of 600 mM Mannitol, 75 mM Citrate, 0.04% sodium bisulfite pH 6.0 buffer using a biomass: digestion buffer ratio of 1:2.5 (w/v).

Following digestion, the apoplastic content fraction was filtered through a 400 μm nylon filter to remove coarse undigested vegetal tissue (<5% of starting biomass). The filtered extract was then centrifuged at room temperature for 15 min at 5000×g to remove protoplasts and intracellular contaminants (proteins, DNA, membranes, vesicles, pigments, etc). Next, the supernatant was depth-filtered (for clarification) using a 0.65 μm glass fiber filter (Sartopore GF plus/Sartorius Stedim) and a 0.45/0.2 μm filter (Sartopore 2/Sartorius Stedim), before being subjected to chromatography.

The clarified apoplastic content fraction was loaded over a cation exchange column (Poros HS Applied Biosystems) equilibrated with an equilibration/elution buffer (50 mM $NaPO_4$, 100 mM NaCl, 0.005% Tween 80 pH 6.0). Once the UV was back to zero, the extract was step-eluted with the equilibration/elution buffer containing increasing concentrations of NaCl (500 mM). Where necessary, the chromatographic fractions were concentrated 10 times using Amicon™ devices equipped with 10 kDa MWCO. Protein analysis was performed as described in previous examples.

Figure 6:
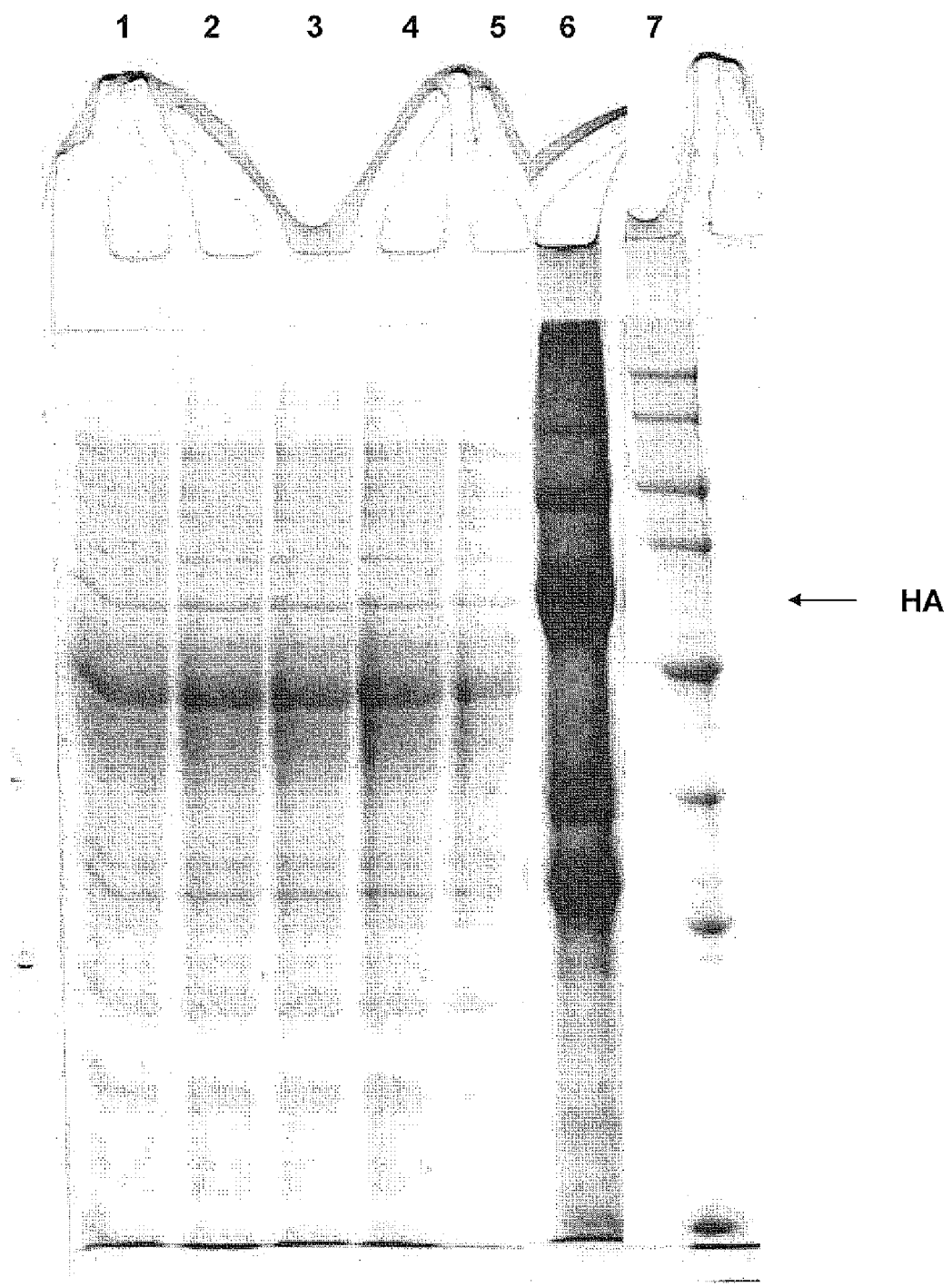
FIG. 6 shows the capture of HA-VLP on cationic exchange resin directly form separation of HA-VLP in the apoplastic fraction. Samples were treated in non-reducing, denaturing sample loading buffer and proteins were separated by SDS-PAGE. Gels were stained with 0.1% Coomassie R-250 solution. Lane 1: Apoplastic fraction after centrifugation, Lane 2-3: Apoplastic fraction after successive microfiltration; Lane 4: Load of the cationic exchange; Lane 5: Flow through fraction of the cationic exchange. Lane 6; elution from cationic exchange, concentrated 10×; Lane 7: Molecular weight standards (kDa).

Under the above-mentioned conditions, most enzymes and plant proteins did not bind to the cation exchange resin whereas the HA-VLP did bind, thus providing a considerable enrichment in HA-VLPs in the eluted fraction (FIG. 6). In addition, as shown in FIG. 6, lane 4 and 5, the cellulases and pectinases did not bind to the cation exchange column at pH under 7. Recovery of HA-VLP, based on HA hemagglutination activity, was of 92% following the cation exchange column. A purification factor of 194 was measured on the eluted fraction from the cation exchange resin.

Example 5: Addition of NaCl to the Digestion Buffer

N. benthamiana plants were agroinfiltrated with Agrobacterium AGL1 strains carrying a construct expressing a hemagglutinin of interest (H1/Cal WT, B/Flo, H5/Indo or H1/Cal X179A) as described in Example 1. Leaves were collected on day 6 post-infiltration, cut into ~1 cm² pieces and digested according to Example 4, except where noted below. Filtration, centrifugation and clarification were performed as described in Example 4.

NaCl was added to digestion buffer to evaluate its potential effect on the HA-VLP recovery rate. The suspected advantages were the potential prevention of non-specific association of HA with plant cells or with particle in suspension that are removed during clarification and potential effect on achievement and/or maintenance and/or improvement of colloidal stability of the HA-VLP.

Addition of 500 mM NaCl to the digestion buffer resulted in an increase of HA-VLP recovery yield per gram of biomass after removal of protoplasts and cellular debris by centrifugation. However, this increase was only noted with the for the H1/Cal WT and B/Flo strains, while the recovery yield for H5 was not significantly increased by this approach (Table 4).

TABLE 4

Effect of the addition of NaCl to the digestion step on the HA-VLP recovery yield (as measured by hemagglutination activity unit, dil: reciprocal of dilution)

| HA strain | Digestion conditions | Concentration in HA (dil/ml) | Yields (dil/g) | Yield increased (X-fold)[1] |
|---|---|---|---|---|
| H5 Indo/05 (#972) | Ø NaCl | 4608 | 12,430 | 1.2 |
|  | 500 mM NaCl | 4608 | 14,921 |  |
| H1 CA/07 WT (#604) | Ø NaCl | 384 | 1,206 | 2.1 |
|  | 500 mM NaCl | 768 | 2,481 |  |
| H1 CA/07 X-179A (#605) | Ø NaCl | 96 | 299 | 8.1 |
|  | 500 mM NaCl | 768 | 2,419 |  |
| B Flo/4 (475) | Ø NaCl | 16 | 52 | 7.5 |
|  | 500 mM NaCl | 128 | 392 |  |

[1]Yield (dil/g) with NaCl divided by Yield (dil/g) without NaCl

Addition of 500 mM NaCl during the digestion further resulted in an increase of the release of HA-VLP during digestion, which in turn resulted into increased recovery rate after clarification for both H1/Cal WT and H1/Cal X-179A strains (Table 5), but not for the H5/Indo strain.

TABLE 5

Effect of the addition of NaCl to the digestion step on the HA-VLP recovery yield (as measured by hemagglutination activity unit) after the clarification step.

| HA strain | Digestion conditions | Recovery after depth filtration[1] | Increase in recovery (X-fold) |
|---|---|---|---|
| H5/Indo (#972) | Ø NaCl | 100% | 1.0 |
|  | 500 mM NaCl | 100% |  |
| H1/Cal WT (#604) | Ø NaCl | 25% | 3.0 |
|  | 500 mM NaCl | 75% |  |
| H1/Cal X-179A (#605) | Ø NaCl | 50% | 2.0 |
|  | 500 mM NaCl | 100% |  |

[1]Recovery is expressed in percentage of hemagglutination activity obtained after depth filtration compared to the activity found in the centrifuged digested extract.

Figure 7A:
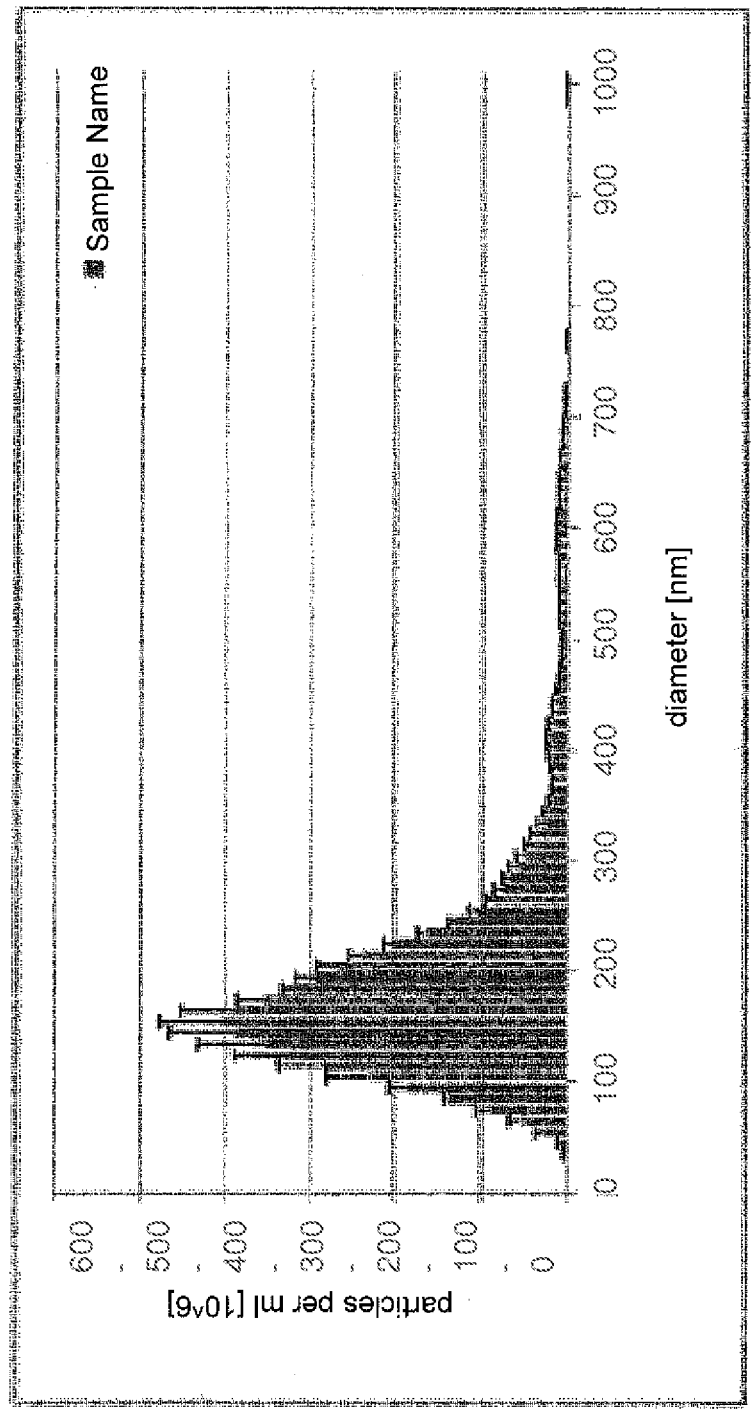
FIG. 7 shows the Nanoparticle Tracking analysis (NTA) profile of H5/Indo VLP (FIG. 7A) and H1/Cal VLP (FIG. 7B) after clarification without addition of NaCl to digestion buffer and of H1/Cal VLP (FIG. 7C) with this addition. NTA experiments were carried out with NanoSight LM20 (NanoSight, Amesbury, UK). The instrument is equipped with a blue laser (405 nm), a sample chamber and a Viton fluoroelastomer o-ring. Videos were recorded at room temperature and analysed using the NTA 2.0 software. The samples were recorded for 60 sec. The shutter and gain were manually chosen so that optimal particle resolution was obtained.
Figure 7B:
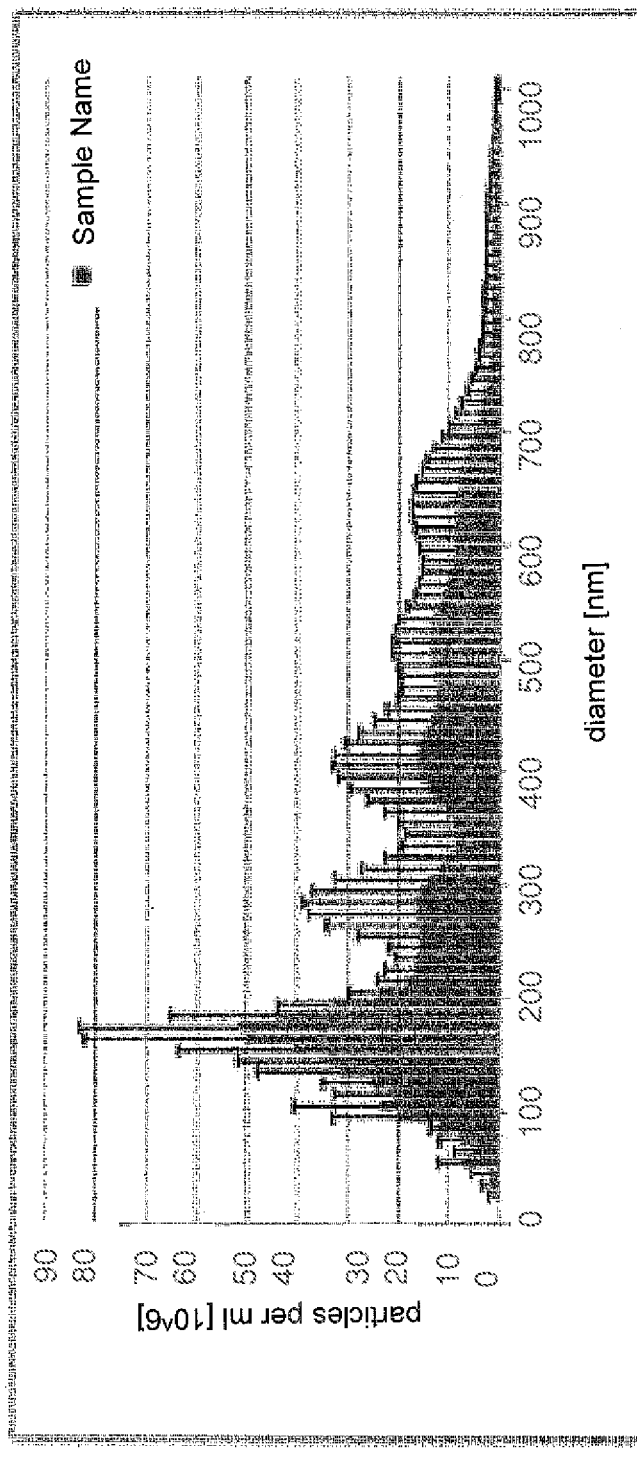
Figure 7C:
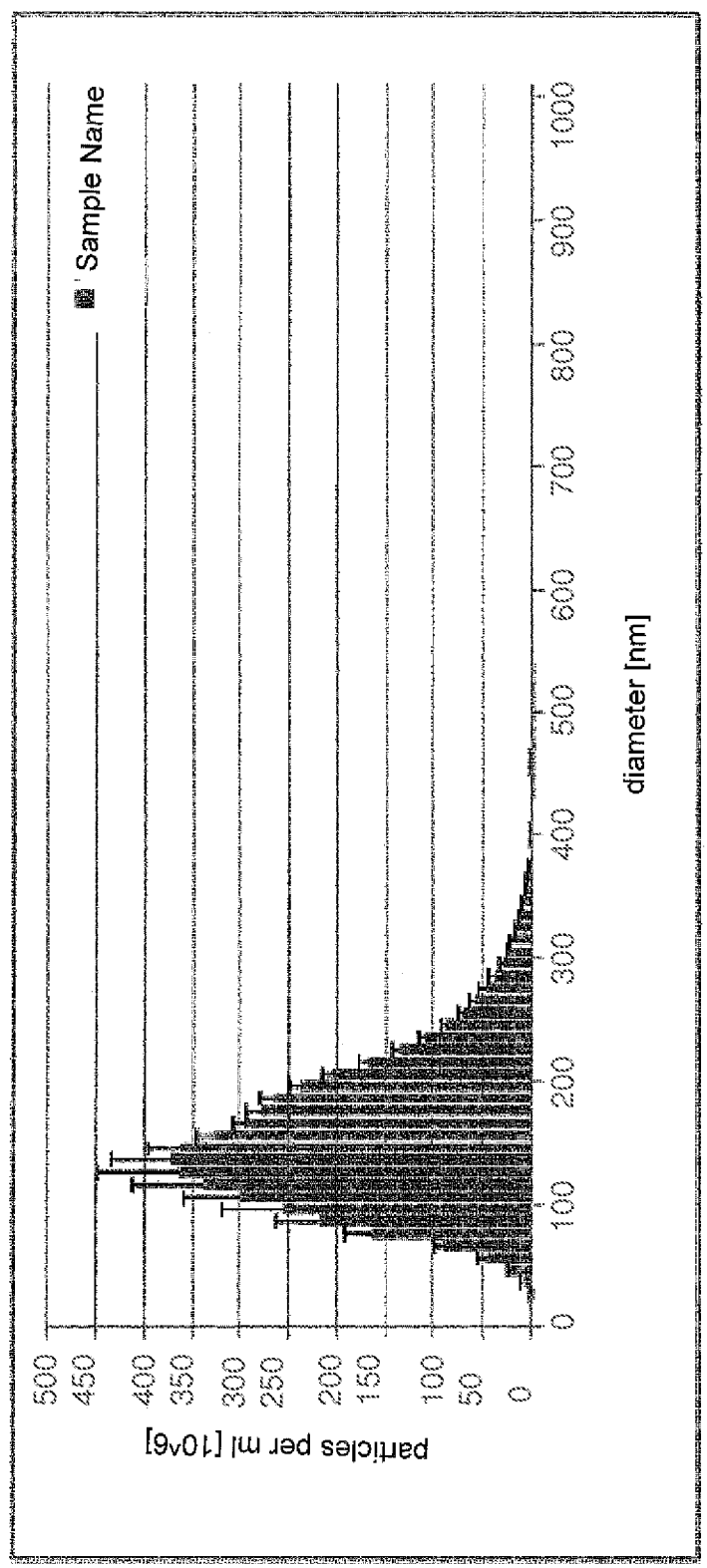
Figure 8:
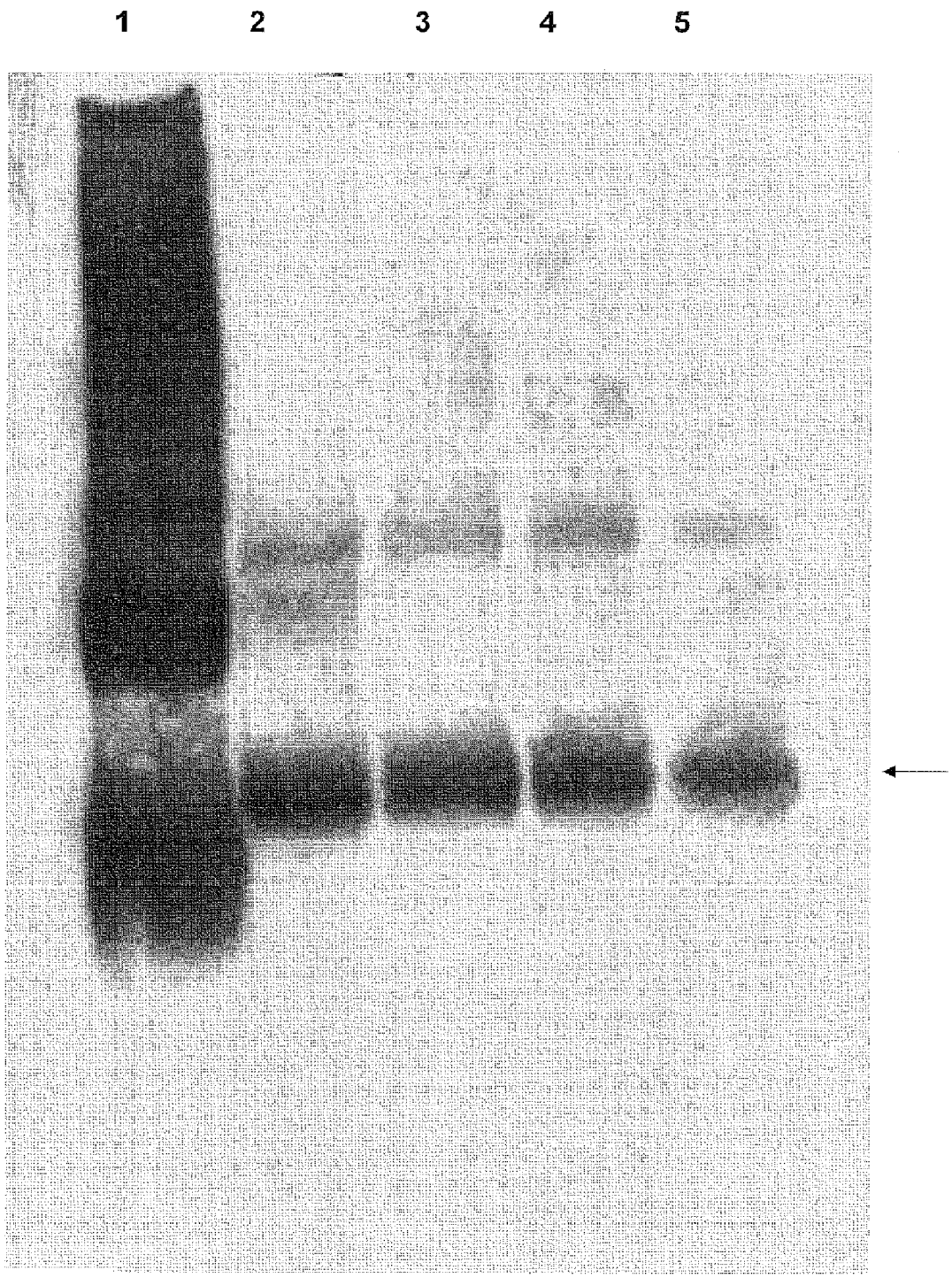
FIG. 8 shows a Western blot of extract of H3/Brisbane VLP generated by enzymatic digestion using different buffers. Lane 1) Pure recombinant HA standard (5 μg, from Immune Technology Corp. IT-003-0042p) Lane 2 to 5 contain 7 μl of centrifuged enzymatic extract performed in the following buffers: Lane 2) 600 mM Mannitol+125 mM citrate+75 mM $NaPO_4$+25 mM EDTA+0.04% bisulfite pH6.2, Lane 3) 600 mM Mannitol+125 mM citrate+75 mM $NaPO_4$+50 mM EDTA+0.04% bisulfite pH6.2, Lane 4) 200 mM Mannitol+125 mM citrate+75 mM $NaPO_4$+25 mM EDTA+0.03% bisulfite pH6.2, Lane 5) 200 mM Mannitol+ 125 mM citrate+75 mM $NaPO_4$+50 mM EDTA+0.03% bisulfite pH6.2. The arrow represents the immunodetection signal of HA0.

The association state of the HA-VLP, with and without the addition of NaCl during enzymatic digestion, was studied using Nanoparticle Tracking Analysis (NTA) for H5/Indo and H1/Cal WT (FIGS. 7A and 7B respectively). A monodisperse preparation of particles was observed for H5 when digestion was performed in absence of NaCl, while the H1/Cal preparation showed much larger array of particle species. The addition of NaCl to the digestion buffer reduced HA-VLP self-association for H1/Cal, as shown by the fairly monodisperse particle distribution found in FIG. 7C. The number of particles at 150 nm for H1/Cal WT-VLPs was enhanced (ca 5-fold) by the addition of 500 mM NaCl to the digestion buffer.

Example 6: Controlling Release of Pigments

*N. benthamiana* plants were agroinfiltrated with *Agrobacterium* AGL1 strains carrying a construct expressing a hemagglutinin of interest (H5/Indo) as described in Example 1

TABLE 7-continued

Release of H5/Indo VLP by digestion of *N. benthamiana* leaves. All conditions were tested in replicates. (Concentration in HA-VLP measured by hemagglutination activity, dil: reciprocal of dilution)

| Pectinase (% v/v) | Cellulase* (% v/v) | Concentration in H5 VLP (dil/ml) |
| --- | --- | --- |
| 0 | 1 | 768 |
| 0 | 2 | 1536 |

*Multifect CX GC

TABLE 8

Release of H1/Cal WT VLP by digestion of *N. benthamiana* leaves. All conditions were tested in replicates. (Concentration in HA-VLP measured by hemagglutination activity, dil: reciprocal of dilution)

| Pectinase (% v/v) | Cellulase* (% v/v) | Concentration in H1 VLP (dil/ml) |
| --- | --- | --- |
| 1 | 2 | 2304 |
| 0 | 2 | 3840 |

*1% each of Multifect CX GC and Multifect CX B

TABLE 9

Release of H1/Cal WT VLP by digestion of *N. benthamiana* leaves. All conditions were tested in replicates. (Concentration in HA-VLP measured by hemagglutination activity, dil:, reciprocal of dilution)

| Pectinase (% v/v) | Cellulase* (% v/v) | Concentration in H1 VLP (dil/ml) |
| --- | --- | --- |
| 1.0 | 1 | 384 |
| 0.75 | 1 | 480 |
| 0.50 | 1 | 480 |
| 0.25 | 1 | 480 |

*Multifect CX GC

Example 8: Enzymatic Digestion in Conditions Near to Neutral pH

Controlling the pH during the digestion can be critical for the extraction of some VLPs. Taking into account that the depolymerisation of the cell wall occurring during the digestion step can release acid sugars that could acidify the solution (i.e. from pH 6 to 5) in the presence of appropriate buffers, and that some VLPs (such as those comprising H3/Bris and B/Flo HA) have already demonstrated a strong sensitivity to mildly acidic conditions, impact of such a potential acidification on the yield of VLP produced was investigated.

*N. benthamiana* plants were agroinfiltrated with *Agrobacterium* AGL1 strains carrying a construct expressing a hemagglutinin of interest (H5/Indo) as described in Example 1. Leaves were collected on day 6 post-infiltration, cut into ~1 cm$^2$ pieces and digested according to Example 4, with modification of digestion buffer to include 0%, 0.25%, 0.5%, 0.75% or 1% v/v Multifect Pectinase FE, Multifect CX-CG cellulase and Multifect CX B cellulase as noted in Tables 7-9. Filtration, centrifugation and clarification were as described in Example 4.

Various digestion buffer compositions were tested to achieve a pH of approximately 5.5 by the end of the enzymatic digestion, including increased concentration of citrate (buffer effect between pH 3.0 and 5.4) and addition of sodium phosphate (buffer effect at pH above 6.0). Table 10 shows that VLPs from the B strain were extracted more efficiently when post-digestion pH was close to pH 6.0.

TABLE 10

Effect of the digestion buffer composition on the extraction yield of B/Flo VLPs.

| Buffer composition[1] | Concentration of B/Flo VLP (dil/ml) | Protein concentration (mg/ml) | pH post-digestion |
| --- | --- | --- | --- |
| 75 mM Citrate + 500 mM NaCl + 25 mM EDTA pH 6.0 | 1 | 0.92 | 5.0 |
| 75 mM Citrate pH 6.0 | 0 | 1.43 | 5.6 |
| 125 mM Citrate + 500 mM NaCl + 25 mM EDTA pH 6.0 | 1.5 | 1.07 | 5.4 |
| 150 mM Citrate + 500 mM NaCl + 25 mM EDTA pH 6.0 | 1.5 | 1.07 | 5.4 |
| 125 mM Citrate + 75 mM NaPO$_4$ + 500 mM NaCl + 25 mM EDTA pH 6.5 | 4 | 2.19 | 5.9 |

[1]All buffers contained 600 mM mannitol, sodium metabisulfite 0.04%

Next, the effect of initiating the digestion at a higher pH in order to reach final pH value close to pH 6.0 was tested. As shown in Table 11, the digestion of plant cell wall with such near-neutral conditions was possible, and did not impaired the extraction yield for H5/Indo VLPs.

TABLE 11

Effect of the initial pH of the digestion buffer on the extraction yield of H5/Indo VLPs.

| Initial pH of digestion solution[1] | Concentration of H5/Indo VLP (dil/ml) | Protein concentration (mg/ml) | pH post-digestion |
| --- | --- | --- | --- |
| 6.5 | 2304 | 2.79 | 6.08 |
| 6.4 | 1536 | 2.31 | 5.93 |
| 6.3 | 2304 | 2.40 | 5.81 |
| 6.2 | 2304 | 2.09 | 5.73 |
| 6.1 | 2304 | 1.72 | 5.61 |

[1]All digestion buffers contained 600 mM mannitol, sodium metabisulfite 0.04%, 125 mM Citrate + 75 mM NaPO$_4$ + 500 mM NaCl + 25 mM EDTA Other components of the digestion solution were also shown to be modifiable without negatively affecting the extraction yield of VLPs. Table 12 illustrates modifications that can be applied to the digestion solution in order to enhance the extraction yield of B/Flo VLPs, while obtaining a post-digestion pH of 5.4-5.7. Such modifications include increasing the concentration of citrate and adding a $PO_4$ buffer. It has been found that increasing the concentration of EDTA generally led to a more acidified extract and to lower VLP extraction yields.

TABLE 12

Effect of various digestion buffer components on the extraction yield of B/Flo VLPs.

Buffer composition[1]

| Mannitol (mM) | Citrate (mM) | $PO_4$ (mM) | EDTA (mM) | pH | Concentration of B VLP (dil/ml) | Protein concentration (mg/ml) | pH post-digestion |
|---|---|---|---|---|---|---|---|
| 600 | 75 | 0 | 25 | 6.1 | 2 | 1.07 | 5.0 |
| 600 | 125 | 0 | 25 | 6.1 | 192 | 0.83 | 5.7 |
| 600 | 125 | 75 | 25 | 6.2 | 192 | 1.81 | 5.5 |
| 600 | 125 | 75 | 50 | 6.2 | 96 | 1.26 | 5.4 |
| 200 | 125 | 75 | 25 | 6.2 | 384 | 1.05 | 5.7 |
| 200 | 125 | 75 | 50 | 6.2 | 96 | 1.04 | 5.4 |
| 200 | 125 | 75 | 75 | 6.2 | 96 | 1.55 | 5.4 |

[1]All buffers contained 500 mM NaCl, and sodium metabisulfite 0.04%.

Buffer composition was further modified to improve the extraction yield of H3/Brisbane VLPs (Table 13)

TABLE 13

Effect of the concentrations of mannitol and sodium bisulfite in the digestion solution on the extraction yield of H3/Bris VLPs.

Buffer composition

| Mannitol (mM) | Sodium bisulfite (%) | EDTA (mM) | pH | Protein concentration (mg/ml) | pH post-digestion |
|---|---|---|---|---|---|
| 600 | 0.04 | 25 | 6.2 | 1.87 | 5.7 |
| 600 | 0.04 | 50 | 6.2 | 1.62 | 5.6 |
| 200 | 0.03 | 25 | 6.2 | 1.89 | 5.7 |
| 200 | 0.03 | 50 | 6.2 | 1.24 | 5.6 |

[1]All buffers containing 125 mM Citrate, 75 mM NaPO4, 500 mM NaCl,

As shown in Tables 12 and 13, mannitol concentration could be reduced to 200 mM without significantly affecting VLPs extraction yield. Further reduction of mannitol concentrations to 100 mM, and even the total omission of mannitol from the digestion solution, did not significantly affect the level of HA-VLP obtained (Table 14).

TABLE 14

Released of H5/Indo VLP from digestion of biomass performed in buffers with different concentration of mannitol.

| Mannitol concentration of the digestion solution[1] | Concentration of H5/Indo VLP (dil/ml) | Protein concentration (mg/ml) |
|---|---|---|
| Trial[2] 1: without mannitol | 2304 | 1.62 |
| Trial[2] 1: with 600 mM mannitol | 3072 | 1.73 |
| Trial[2] 2: with 100 mM mannitol | 4608 | 1.77 |
| Trial[2] 2: with 600 mM mannitol | 4608 | 2.0 |

[1]All buffers containing 75 mM Citrate pH 6.0 + sodium metabisulfite 0.04%.
[2]Two trials were were performed to compare the extraction yields of VLPs without mannitol (Trial 1) and with 100 mM mannitol (Trial 2) versus 600 mM mannitol.

Example 9: Suitability of Enzymatic Digestion to a Broad Variety of HA-VLPs

The enzymatic digestion method for plant biomass described herein has the potential to be applied to extracting of a broad variety of HA-VLPs. Adding to the extraction of HA-VLPs comprising H5/Indo, H1/Cal WT VLP, H3/Bris and B/Flo shown in previous examples, the method described herein was also shown to be suitable for the extraction of HA-VLPs from seasonal H1/Bris and H1/NC, as shown in Table 15.

TABLE 15

Release of seasonal H1/Bris and H1/NC VLP from digestion of agroinfiltrated *N. benthamiana* leaves. (concentration in HA measured by hemagglutination activity, dil: reciprocal of dilution)

| HA strain | Concentration in HA (dil/ml) |
|---|---|
| H1/Bri | 1536 |
| H1/NC | 384 |

Example 10: Antibody Preparation, Expression and Analysis

Assembly of C2B8 Expression Cassette (Construct #595)

C2B8 is a chimeric (mouse/human) monoclonal antibody directed against the B-cell-specific antigen CD20 expressed on non-Hodgkin's lymphomas (NHL). C2B8 mediates complement and antibody-dependent cell-mediated cytotoxicity and has direct antiproliferative effects against malignant B-cell lines in vitro (N Selenko et. al., Leukemia, October 2001, 15 (10); 1619-1626).

A DNA fragment comprising 84 bp of the alfalfa plastocyanin promoter, the complete C2B8 light chain coding sequence and the complete alfalfa plastocyanin teminator was synthesized (LC fragment). The LC fragment was flanked by a DraIII restriction site (found in the plastocyanin promoter) and a EcoRI site downstream of the plastocyanin terminator. The sequence of LC fragment is presented in FIG. 9 (SEQ ID NO:15). The plasmid containing LC fragment was digested with DraIII and EcoRI and cloned into construct #660 (D'Aoust et al., Plant Biotechnol. J. 2008, 6: 930-940), previously digested with the same enzymes. The resulting plasmid was named construct number 590. A second DNA fragment was synthesized which comprises 84 bp of the alfalfa plastocyanin promoter, the complete C2B8 heavy chain coding sequence and the complete alfalfa plastocyanin teminator (HC fragment). The HC fragment was flanked by a DraIII restriction site (found in the plastocyanin promoter) and a EcoRI site downstream of the plastocyanin terminator. The sequence of HC fragment is presented in FIG. 16 (SEQ ID NO:16). The plasmid containing HC fragment was digested with DraIII and EcoRI and cloned into construct #660 (D'Aoust et al., Plant Biotechnol. J. 2008, 6: 930-940), previously digested with the same enzymes. The resulting plasmid was named construct number 592. The *A. tumefacians* strain comprising 592, is termed "AGL1/592".

Figure 11A:
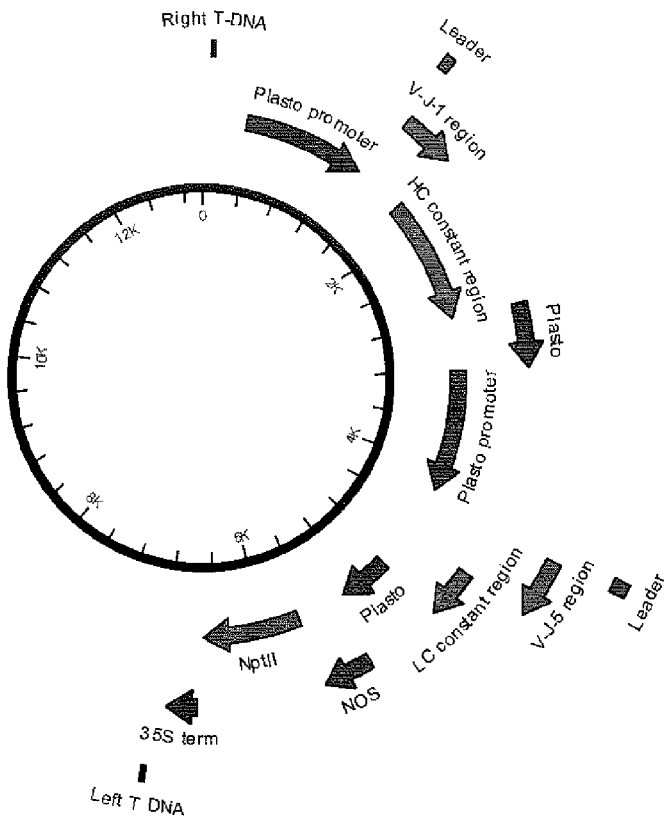
FIG. 11A and FIG. 11B show schematic representations of constructs #595 (FIG. 11A) and #R472 (FIG. 11B), respectively.
Figure 11B:
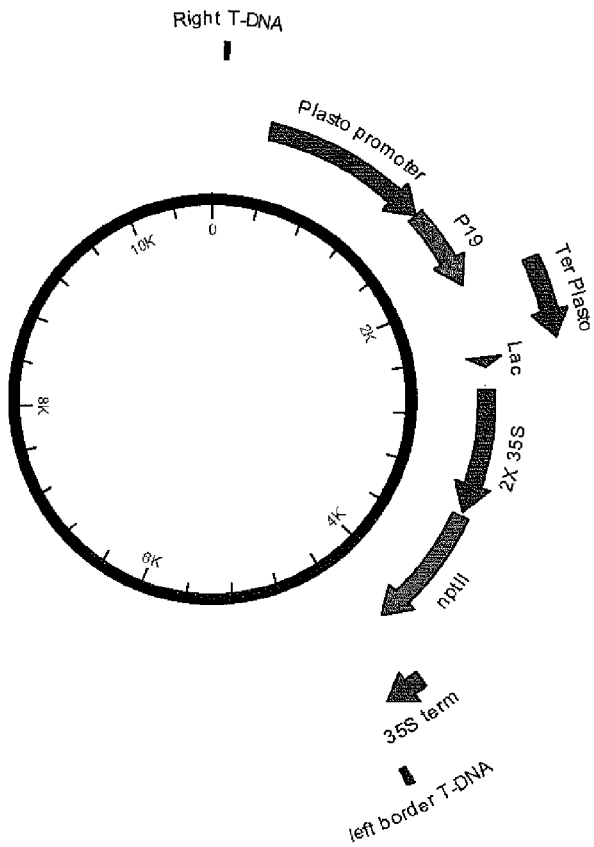

The plasmid comprising a dual expression cassette for C2B8 expression (construct #595) was assembled as follows. Construct number 592 was digested with EcoRI, treated with Klenow fragment to generate blunt-ends and digested with SbfI. The resulting fragments, comprising the complete cassette for the expression of C2B8 heavy chain flanked by a SbfI site and a blunt-end, was inserted into construct #590 previously digested with SbfI and SmaI. FIG. 11A presents a schematic representation of construct #595 used for the expression of C2B8 in plants.

Assembly of P19 Expression Cassette (Construct #R472)

The construct R472, encoding p19 protein is described above ("Suppressors of silencing"; see FIG. 11B)

Preparation of Plant Biomass, Bacterial Inoculum, Agroinfiltration, and Harvesting

*Nicotiana benthamiana* plants were grown as described above ("Preparation of plant biomass, inoculum, agroinfiltration, and harvesting") in a greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* bearing construct #595 or #R472 were grown in BBL Select APS LB broth medium supplemented with 10 mM 2-[N-morpholino]ethanesulfonic acid (MES), 50 µg/ml kanamycin and 25 µg/ml of carbenicillin pH5.6 until they reached an $(OD_{600}>2.0$. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 6.7 culture volumes and allowed to warm before use. Whole plants of *N. benthamiana* were placed upside down in the bacterial suspension in an air-tight stainless steel tank under a vacuum of 20-40 Torr for 1 min. Following infiltration, plants were returned to the greenhouse for a 5 day incubation period until harvest. Infiltrations were performed as co-infiltration with strains AGL1/595 and AGL1/R472 in a 1:1 ratio.

Leaf Sampling and Total Protein Extraction (Mechanical Extraction)

Following incubation, the aerial part of plants was harvested and used immediately. Total soluble proteins were extracted by homogenizing plant tissue in a domestic blender for 3 min. with 1.5 volumes of cold 20 mM $NaPO_4$ pH 6.0, 0.15 M NaCl and 2 mM sodium metabisulfite. Following homogenization, the slurry of ground plant material was filtered on Miracloth to remove large insoluble debris. The pH of the extract was adjusted to 4.8 by addition of 1M HCl and the non-soluble materials were removed by centrifugation 18 000 g for 15 min (4° C.). The supernatant was collected and the pH was adjusted to 8.0 with Tris base 2M. The insoluble materials were removed by centrifugation at 18 000 g for 15 min at 4° C. and the crude extract (supernatant) was collected. The total protein content of clarified crude extracts was determined by the Bradford assay (Bio-Rad, Hercules, Calif.) using bovine serum albumin as the reference standard.

Protein Extraction by Cell Wall Digestion

Leaf tissue was collected from the *Nicotiana benthamiana* plants and cut into ~1 cm² pieces. Leaf pieces were placed in 2.425 volumes of digestion solution (75 mM citrate pH 6.9, 600 mM mannitol, 1% Multifect Pectinase FE, 1% Multifect CXG, 1% Multifect B). This preparation was spread evenly into a shallow vessel and incubated for 16 hours on an orbital shaker at 120 rpm and 18° C. Following incubation, leaf debris were removed by filtration on a nylon filter (250 µm mesh). The extract was centrifuged at 5 000 g for 15 min. (22° C.) and the supernatant was collected and filtered on 0.65 µm glass fiber. The extract was adjusted to pH 6.0 with 0.5 M Tris base and filtered on PES membrane 0.45/0.22 µm.

Ammonium Sulfate Precipitation and Antibody Purification

Ammonium sulfate was slowly added to protein extracts to reach 45% saturation. The extract was kept on ice for 60 min and centrifuged at 18 000 g for 20 min. (4° C.). The supernatant was discarded and the pellet was kept frozen (−80° C.) until use.

The frozen protein pellet was thawed and resuspended in $\frac{1}{10}$ volume (compared to the volume prior to precipitation) of protein resuspension solution (50 mM Tris pH 7.4, 150 mM NaCl). The protein solution was centrifuged at 12 000 g for 20 min. (4° C.) to remove non-solubilised materials. The protein solution was loaded onto MabSelect Sure resin (GE Healthcare, Baie d'Urfé, Canada). The column was washed with 10 CV of 50 mM Tris pH 7.4, 150 mM NaCl and the antibody was eluted with 6 CV of 100 mM sodium citrate pH 3.0. The elution volume was collected in 1 CV fractions in tubes containing $\frac{1}{10}$ CV of 2 M Tris pH 7.4, NaCl 150 mM. Elution fractions were selected based on their protein content (measured by Bradford) and selected fractions were pooled and kept frozen (−80° C.) prior to analysis.

Protein Quantification and SDS-PAGE Analysis

Total protein content was determined by the Bradford assay (Bio-Rad, Hercules, Calif.) using either bovine serum albumin (for crude protein extracts) or commercial rituximab (Rituxan®, Hoffmann-La Roche, Mississauga, Canada) (for purified antibodies) as the reference standard. Coomassie-stained SDS-PAGE was performed as described by Laemmli (Nature 1970, 227: 680-685).

C2B8 Quantification by ELISA

Multiwell plates (Immulon 2HB, ThermoLab System, Franklin, Mass.) were coated with 2.0 µg/ml of monoclonal mouse anti-human IgG (Abcam, Ab9243) in 50 mM carbonate buffer (pH 9.6) at 4° C. for 16-18 h. Multiwell plates were then blocked through a 1 h incubation in 1% casein in phosphate-buffered saline (PBS) (Pierce Biotechnology, Rockford, Ill.) at 37° C. A standard curve was generated with dilutions of Rituximab (Rituxan®, Hoffmann-La Roche, Mississauga, Canada). When performing the immunoassays, all dilutions (control and samples) were performed in a plant extract obtained from plant tissue infiltrated and incubated with a mock inoculum (AGL1/R472 only) to eliminate matrix effect. Plates were incubated with protein samples and standard curve dilutions for 1 h at 37° C. After three washes with 0.1% Tween-20 in PBS (PBS-T), the plates were incubated with a peroxidase-conjugated dunkey anti-human IgG antibody (1/4000 dilution in blocking solution) (Jackson ImmunoResearch 709-035-149) for 1 h at 37° C. The washes with PBS-T were repeated and the plates were incubated with a 3,3',5,5'-Tetramethylbenzidine (TMB) Sure Blue peroxidase substrate (KPL, Gaithersburg, Md.). The reaction was stopped by adding 1N HCl and the absorbance was read at 450 nm. Each sample was assayed in triplicate and the concentrations were interpolated in the linear portion of the standard curve.

N-Glycan Analysis

Samples comprising C2B8 (Rituxan™; 50 µg) were separated on 15% SDS/PAGE. Heavy and light chains were revealed with Coomassie blue and the protein band corresponding to the heavy chain was excised and cut into small fragments. Fragments were washed 3 times with 600 μL of a solution of 0.1M NH4HCO3/CH3CN (1/1) for 15 minutes each time and dried.

Reduction of disulfide bridges occurred by incubation of the gel fragments in 600 μL of a solution of 0.1M DTT in 0.1M NH4HCO3, at 56° C. for 45 minutes. Alkylation was carried out by adding 600 μL of a solution of iodoacetamide 55 mM in 0.1M NH4HCO3, at room temperature for 30 minutes. Supernatants were discarded and polyacrylamide fragments were washed once again in NH4HCO3 0.1M/CH3CN (1/1).

Proteins were then digested with 7.5 μg of trypsin (Promega) in 600 μL of 0.05M NH4HCO3, at 37° C. for 16 h. Two hundred μL of CH3CN were added and the supernatant was collected. Gel fragments were then washed with 200 μL of 0.1M NH4HCO3, then with 200 μL CH3CN again and finally with 200 μL formic acid 5%. All supernatants were pooled and lyophilized.

Glycopeptides were separated from peptides by chromatography on a Sep-Pack C18 cartridge. Glycopeptides were specifically eluted with 10% CH3CN in water and then analyzed by MALDI-TOF-MS on a Voyager DE-Pro MALDI-TOF instrument (Applied Biosystems, USA) equipped with a 337-nm nitrogen laser. Mass spectra were performed in the reflector delayed extraction mode using dihydrobenzoic acid (Sigma-Aldrich) as matrix.

Example 11: Comparison of C2B8 Antibody Extraction Yields

Enzymatic digestion was compared to mechanical extraction for the extraction of C2B8 antibody. *N. benthamiana* plants were agroinfiltrated with AGL1/595 and AGL1/R472. After 6 days of incubation, the leaves were harvested and proteins were extracted by enzymatic digestion or mechanical extraction. Extractions were performed twice and the resulting extracts were compared for volume, protein concentration and antibody (C2B8) content. Results are presented in Table 16.

Example 13: Comparison of Purified C2B8 Antibody (Protein Content)

Figure 12:
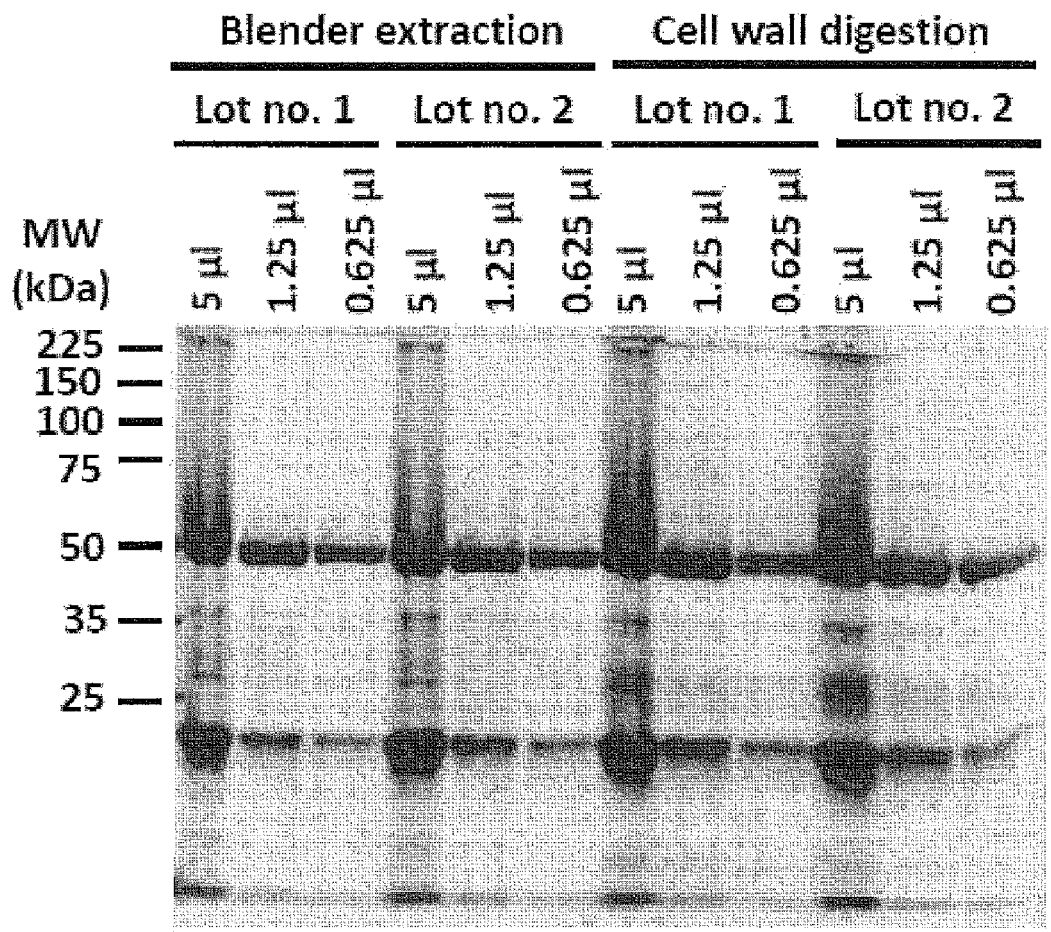
FIG. 12 SDS-PAGE comparison of antibodies purified from extracts produced by mechanical disruption (blender extraction) and enzymatic digestion of cell walls. For each extraction methods, two lots were processed and purified independently.

The C2B8 antibody was purified from the extracts by affinity chromatography on protein A as described in Example 10. The products purified from extracts obtained by mechanical extraction or digestion were compared on the basis of their protein content. The electrophoretic profile of the antibodies purified from each extraction lot is shown in FIG. 12. The results show that the profiles of the products purified from either blender extraction or cell wall digestion are similar.

Example 14: Comparison of Purified C2B8 Antibody (N-Glycosylation)

N-glycosylation of proteins consist in the addition of a complex glycan structure on the asparagine of secreted proteins bearing the N-X-S/T sequence, where N is the asparagine, X is any amino acid except a proline and S/T is a serine or a threonine. A precursor glycan is added early in the endoplasmic reticulum during the translation of the protein and, during their transit across the secretion pathway, N-glycans are subject to maturation. From a high-mannose type N-glycan in the endoplasmic reticulum (ER), N-glycan maturation in plants includes the addition and removal of glucose residues, the removal of mannoses in distal positions and the addition of N-acetylglucosamine, xylose, fucose and galactose residues. N-glycan maturation in plants is described by Gomord et al. in Post-translational modification of therapeutic proteins in plants (Curr. Opin. Plant Biol. 2004, 7: 171-181). Enzymes of the N-glycosylation pathway are positioned at precise locations in each compartment of the secretion pathway, namely the endoplasmic reticulum, the cis-Golgi, the medial Golgi and the trans-Golgi. Therefore, the N-glycosylation pattern of a protein will differ depending on its position at the moment of extraction. We have previously observed that a certain proportion of an antibody produced using agroinfiltration of *N. benthamiana* bore immature N-glycans of high mannose-type despite being targeted to the apoplast (Vezina et al.,

TABLE 16

Comparison of extraction yield for mechanical disruption (blender extraction) and enzymatic digestion of cell walls.

| Extraction lot | Biomass treated (g) | Crude extract volume (ml) | Protein concentration in the extract (mg/ml) | C2B8 concentration (% TSP) | C2B8 extraction yield (mg C2B8/kg FW) |
|---|---|---|---|---|---|
| Blender, lot no. 1 | 700 | 1400 | 2.42 | 3.33% | 161.4 |
| Blender, lot no. 2 | 700 | 1480 | 2.47 | 3.65% | 190.5 |
| Digestion, lot no. 1 | 700 | 2337 | 1.45 | 4.89% | 236.6 |
| Digestion, lot no. 2 | 700 | 2233 | 1.64 | 4.68% | 244.9 |

From 700 g of biomass, the mechanical extraction generated a average of 1440 ml of protein extract whereas the digestion generated 2285 ml of protein extract. The percentage of C2B8 antibody was higher in the extract from digestion (average value of 479% of extracted proteins) than in the extract produced in the blender (average value of 3.49% of extracted protein). Together, the higher volume of extract and the higher concentration of antibody found in the extract result in an 37% higher extraction yield for the digestion (240.75 mg C2B8/kg fresh weight) than the mechanical extraction (175.95 mg C2B8/kg fresh weight).

Plant Biotechnol. J. 2009 7: 442-455). A similar observation was reported elsewhere (Sriraman et al., Plant Biotechnol. J. 2004, 2, 279-287). In both cases, the presence of immature N-glycans on a certain proportion of antibodies was interpreted as the consequence of the presence of antibodies in early compartments of the secretion pathway at the moment of extraction.

The following study examined whether extraction of secreted glycoproteins by cell wall digestion was preferably extracting recombinant proteins bearing complex N-glycan. Antibodies and other glycoproteins secreted into the apoplast are expected to bear N-glycans having completed their maturation. Mature N-glycans most commonly bear terminal N-acetyglucosamine or galactose residues and are also named complex N-glycans. In contrast, immature N-glycans, mostly found on proteins en route in the secretory pathway, comprise terminal mannose residues. High mannose content of N-glycans on C2B8 (Rituxan™) has been associated with reduced half life in the blood stream (Kanda et al., Glycobiology 2006, 17: 104-118). In this context, an extraction method capable of favoring the extraction of apoplastic glycoproteins bearing complex N-glycans from plants would be desirable.

Figure 13A:
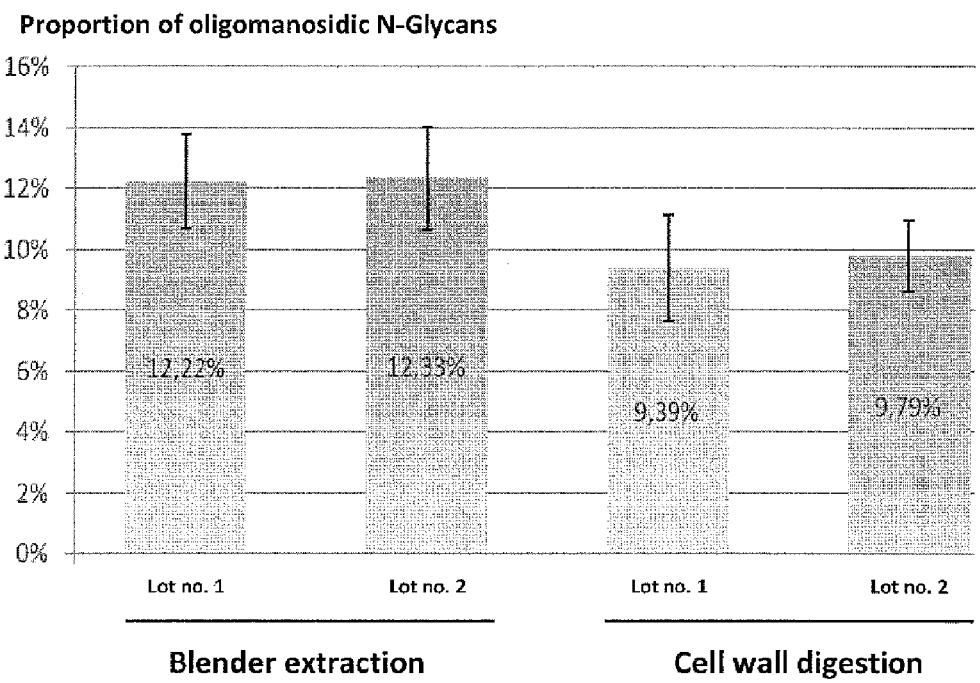
FIG. 13A shows a comparison of the proportion of oligomannosidic N-glycans on C2B8 purified by mechanical disruption (blender extraction) and enzymatic digestion of cell walls.
Figure 13B:
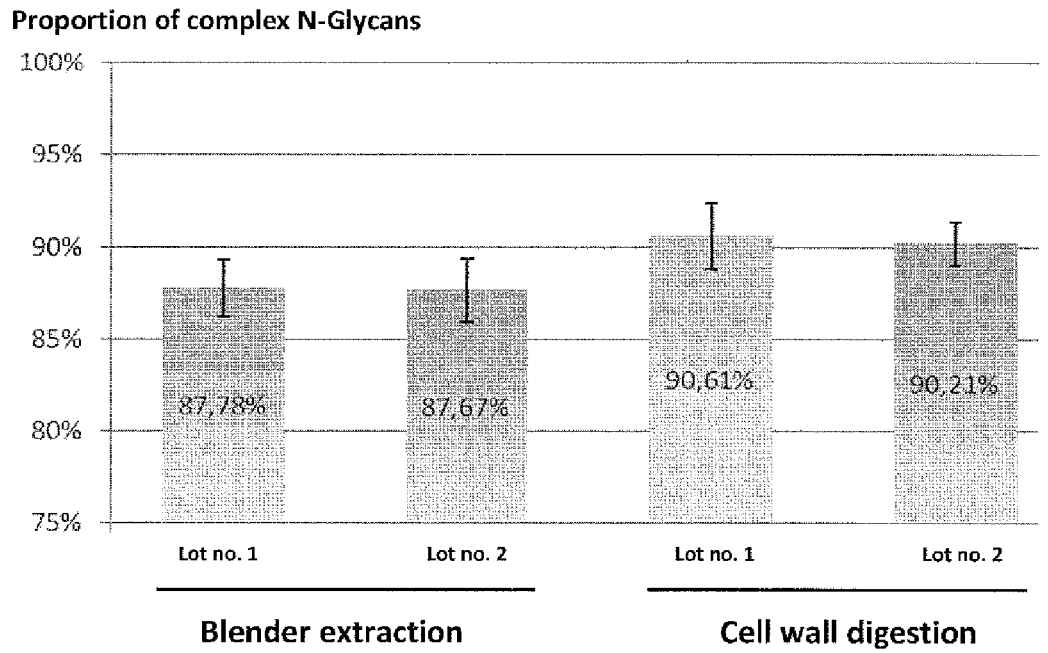
FIG. 13B shows a comparison of the proportion of complex N-glycans on C2B8 purified by mechanical disruption (blender extraction) and enzymatic digestion of cell walls.

A comparative analysis of N-glycosylation on purified C2B8 antibodies was carried out as described in Example 10. The results demonstrate that the antibodies purified from digested biomass bore a significantly lower proportion of oligomannosidic N-glycans (FIG. 13A) and, as a corollary, a significantly higher proportion of complex N-glycans (FIG. 13B).

Extraction by cell wall digestion could also be applied to plants co-expressing a glycoprotein and one or more enzymes for modifying N-glycosylation profile as described in WO 20008/151440 (Modifying glycoprotein production in plants; which is incorporated herein by reference) for favoring the recovery of glycoproteins bearing modified mature N-glycans. For example, mature N-glycans could be reduced, or exempt of xylose and fucose residues.

The method to modify N-glycosylation may involve co-expressing the protein of interest along with a nucleotide sequence encoding beta-1.4galactosyltransferase (GalT; provided as SEQ ID NO:14 of WO 20008/151440), for example, but not limited to mammalian GalT, or human GalT however GalT from another sources may also be used. The catalytic domain of GalT (for example nucleotides 370-1194 of SEQ ID NO:14 as described in WO 20008/151440), may also be fused to a CTS domain of N-acetyl-glucosaminyl transferase (GNT1; for example, comprising nucleotides 34-87 of SEQ ID NO:17 as provided in WO 20008/151440), to produce a GNT1-GalT hybrid enzyme. The hybrid enzyme may be co-expressed with a sequence encoding the suprastructure protein of interest. Additionally, the sequence encoding the suprastructure of interest may be co-expressed with a nucleotide sequence encoding N-acetyl-glucosaminyltransferase III (GnT-III; SEQ ID NO:16 as described in WO 20008/151440). A mammalian GnT-III or human GnT-III, GnT-III from other sources may also be used. Additionally, a GNT1-GnT-III hybrid enzyme (SEQ ID NO:26; as described in WO 20008/151440), comprising the CTS of GNT1 fused to GnT-III may also be used.

Example 15: Treatment of Plant Biomass to Loosen the Plant Cell Wall

N. benthamiana plants were agroinfiltrated with Agrobacterium AGL1 strains carrying a construct expressing a hemagglutinin of interest (H1/CA07) as described in Example 1. Leaves were collected on day 5 post-infiltration, cut into ~1 cm² pieces and digested according to Example 4, and using a 75 mM Citrate, 500 mM NaCl, pH 6.1 buffer with modifications to include 0, 25, 100 or 250 mM EDTA. Coarse filtration and centrifugation of cell debris were as described in Example 4. The supernatant from this centrifugation were tested for protein concentration and hemagglutining activity. The plants were treated with or without the digestion enzymes described in Example 4 to illustrate the effect of EDTA on released of protein. It is worth noticing that the enzymes added to the digestion buffer account for ca 0.8 mg/ml. FIG. 15 shows that the addition of EDTA to the plant, without the enzymes can extract proteins from the apoplast, which in contains the H1 VLPs.

FIG. 15 also shows that EDTA has an enhancing effect of released of H1 VLPs, with a maximum effect between 20-100 mM. EDTA is thought to act as a Ca++ scavenger, which is an important constituent of plant cell wall, to help in depolymerisation of plant cell wall.

Example 16: Treatment of Plant Biomass to Loosen the Plant Cell Wall

*N. benthamiana* plants were agroinfiltrated with *Agrobacterium* AGL1 strains carrying a construct expressing a hemagglutinin of interest (H1/CA07) as described in Example 1. Leaves were collected on day 5 post-infiltration, cut into ~1 $cm^2$ pieces and digested according to Example 4, The control digestion buffer contained 1.0% (v/v) Multifect Pectinase FE, 1.0% (v/v) Multifect CX CG orand 1.0% (v/v) Multifect CX B (all from Genencor), each in a solution of 600 mM Mannitol, 75 mM Citrate, 25 mM EDTA, 0.04% sodium bisulfite pH 6.0 buffer using a biomass: digestion buffer ratio of 1:2.5 (w/v). A comparative digestion containing 3% Multifect Pectinase FE, (v/v) in the same digestion buffer was performed. Coarse filtration and centrifugation of cell debris were as described in Example 4. The supernatant from this centrifugation were tested for protein concentration and hemagglutining activity. Table 17 shows that the pectinase component allows for the release of proteins and HA VLPs.

Table 17 shows the release of proteins and VLPs upon plant treatment with 3% pectinase, with or without the usage of cellulose- and hemicellulose-specific enzymes. Protein concentration was measured using the Bradford assay. HA activity is expressed as the inverse of the lowest quantity of protein extractable to hemagglutinate red blood cells.

TABLE 17

| Treatment | Protein concentration (mg/ml) | HA/mg |
|---|---|---|
| Control digestion using 1% of each of cellulase CXG and CB + 1% pectinase FE 1% | 1.44 | 18474 |
| Digestion using 3% pectinase 3% | 1.27 | 18474 |

Example 17: Treatment of Leaves and Plants by Enzyme Infiltration

Enzyme infiltration may allow increased release of VLPs from whole leaves. To examine this approach, VLP's were extracted from leaves that were infiltrated with a cell wall loosening composition either under vacuum or under pressure.

VLP Extraction

Plants were agroinfiltrated with AGL1/#685 as described in example 1. Leaf tissue was collected from the *N. benthamiana* plants at day 5 or 7 post-infiltration. Whole plants and/or whole leaves were soaked or subjected to infiltration (using similar conditions described above for agroinflitration, see "Preparation of plant biomass, inoculum, agroinfiltration, and harvesting") in an enzyme solution comprising: one ore more pectinase: (Biocatalyst 162L from 1% to 4% (v/v), Biocatalysts 444L from 1.0% to 4.0% (v/v), or a combination thereof, each at from 1% to 4% (v/v), Biocatalysts PDN33 from 1% to 4% (v/v) in a 600 mM Mannitol, 75 mM Citrate, 0.04% sodium bisulfite pH 6.0 buffer using a ratio of 1:2.5 (w/v) fresh biomass; digestion buffer. Whole plants or whole leaves were also soaked or infiltrated in an enzyme solution comprising pectinase (Biocatalyst 162L from 1% to 4% (v/v) and Biocatalysts 444L from 1.0% to 4.0% (v/v)), and cellulase (Multifect CX CG and/or Multifect CX B (Genencor), from 1.0% to 4.0% each (v/v)), in a 600 mM Mannitol, 75 mM Citrate, 0.04% sodium bisulfite pH 6.0 buffer using a ratio of 1:2.5 (w/v) fresh biomass; digestion buffer. In one example Biocatalyst 162L was added to 1% and Biocatalyst 44L was added to 4% 444L, however a person skilled in the art would understand that these percentages may be varied depending on the digestion period. The higher the pectinase activity, the shorter the digestion period. It is further appreciated by a person skilled in the art that a broad range of enzymes known in the art may be used as long as the pectolytic requirements of this procedure are met. The buffer may be either adjusted to pHs from 5.0 to 6.5 or any amount therebetween and either left as is for the duration of the digestion, or the pH can be adjusted to remain at the initial value (i.e. in a range of 5.0 to 6.5 any amount therebetween) by addition of buffering solutions. Furthermore the buffer may be optionally complemented with various anti-oxidants such for example metabisulfite. Enzymes from the enzyme solution are infiltrated into whole plants or whole leaves by either vacuum or pressure infiltration.

Following enzyme infiltration the whole leaves and/or plants may be either left in digestion buffer and shaken at the end of the procedure, or slowly shaken (between 40-80 rpm depending on the type of vessel) during the whole digestion period. The different agitations will lead to different levels of digestion, especially for the vascular tissue (leaf veins). Leaves that are not infiltrated with enzyme will take longer (i.e. the 15 hour procedure as outlined in Example 4) and stronger agitation is required.

Figure 16A:
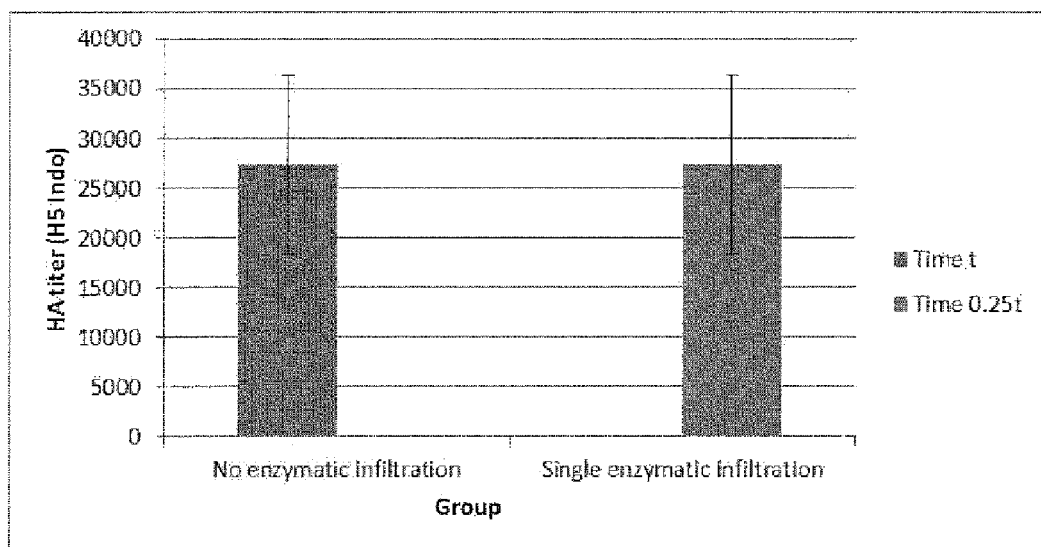
FIG. 16A shows protein released after 4 hours (Time 0.25t) from leaves that have been infiltrated with an enzyme solution/digestion solution (see Example 17), compared to leaves that have been soaked and shaken in the same enzyme solution/digestion solution for 16 hours (Time t).
Figure 16B:
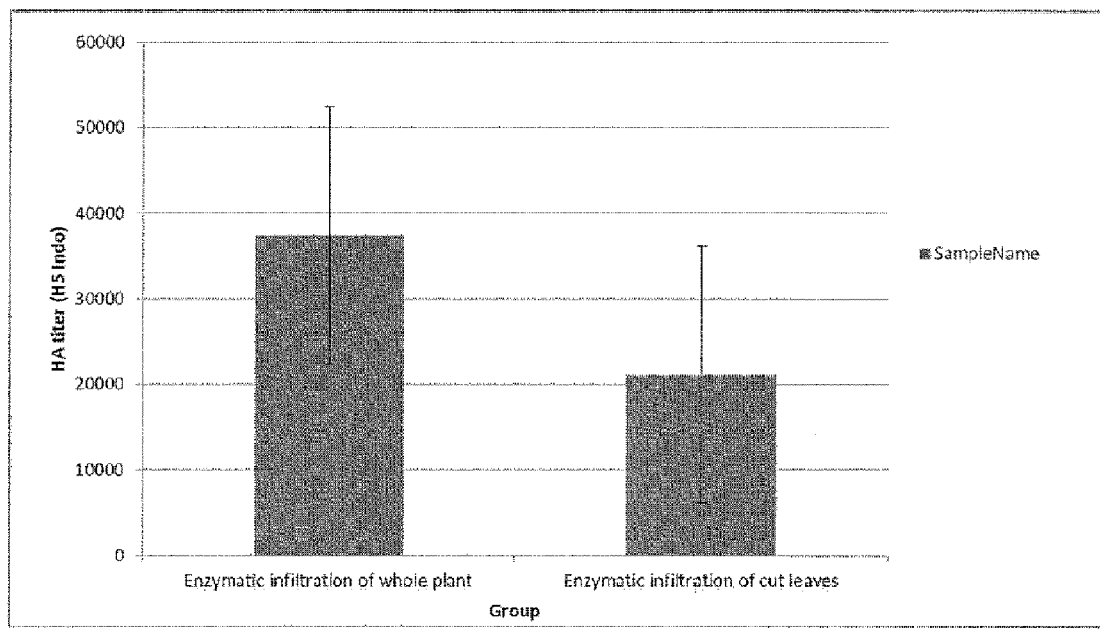
FIG. 16B shows protein released from whole plant/leaves infiltrated with an enzyme solution/digestion solution compared to cut leaves infiltrated with the same enzyme solution/digestion solution.
Figure 16C:
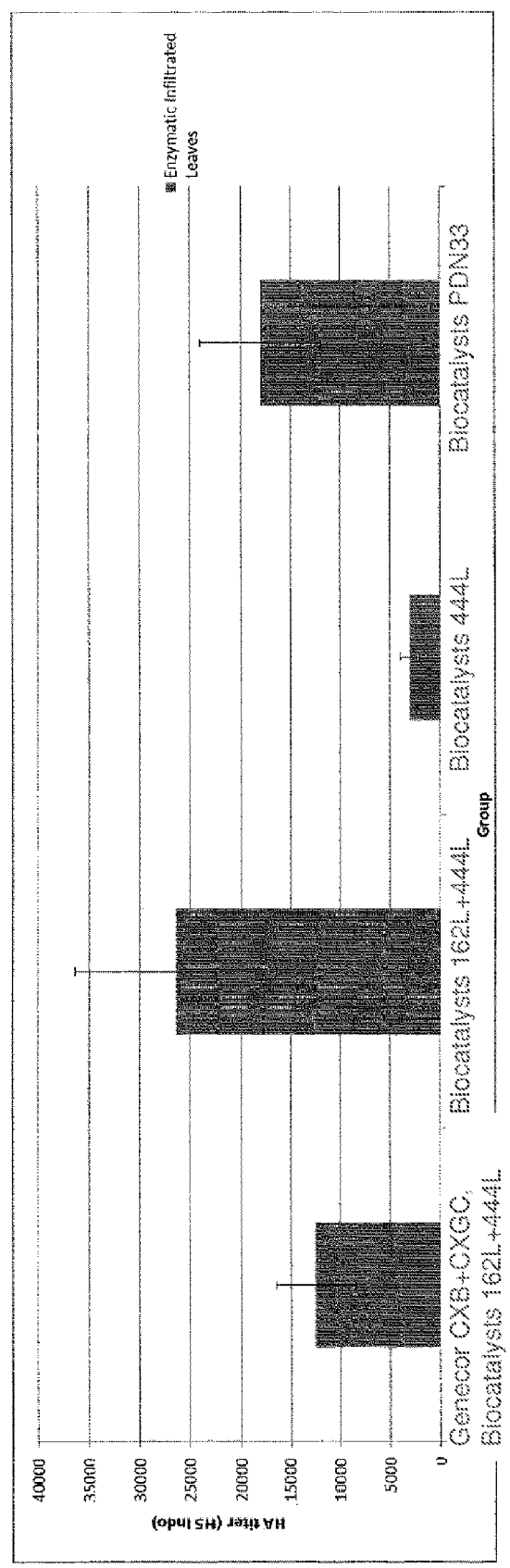
FIG. 16C shows protein released upon treating whole leaves with either one or more than one pectinase (for example Biocatalysts 162L and/or Biocatalysts 444L) with or without the usage of Multifect CXCG and Multifect CX B (Genencor). Furthermore, protein release upon treating whole leaves with Biocatalysts PDN33 is shown.
Figure 16D:
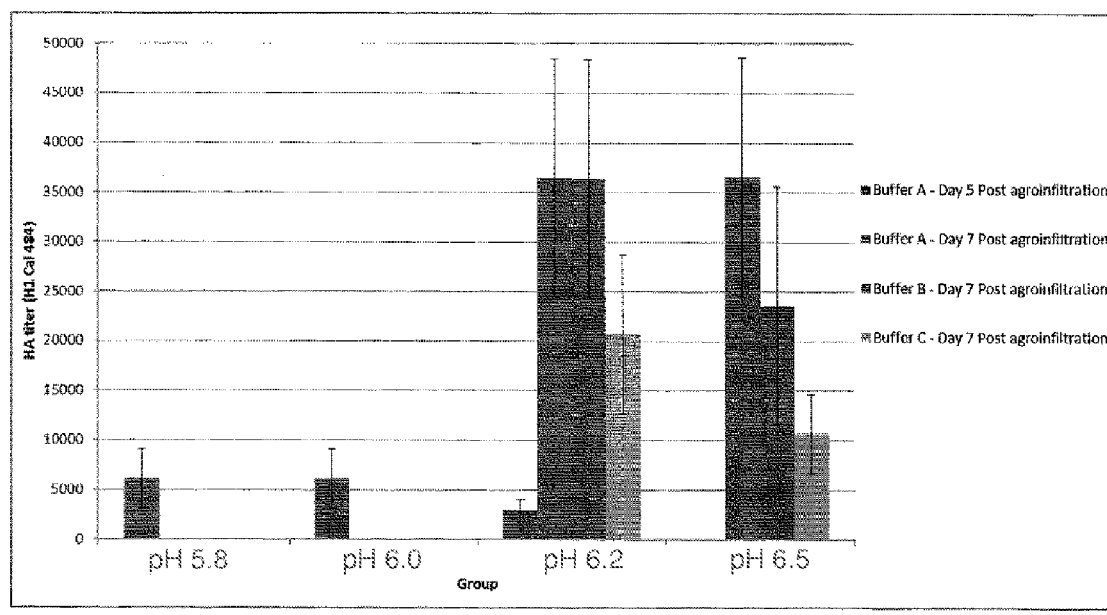
FIG. 16D shows protein released upon treating whole leaves either after 5 days with a buffer at a pH 5.8, pH 6.0 or pH 6.2 or after treating whole leaves after 7 days post agroinfiltration with various buffers at pH 6.2 or pH 6.5.

FIG. 16A shows that as many VLPs (HA release into solution) are released in 4 hours (Time 0.25t) from leaves that have been infiltrated with an enzyme solution, than after 16 hours (Time t) when leaves are only soaked and shaken in same enzyme solution. It is also observed (results not shown) that repeated infiltrations is more beneficial than a prolonged single infiltration step. Enzyme infiltration allows for the same amount of HA/VLP being released in a quarter of the digestion time, when compared to leaves that are soaked and shaken, but not infiltrated with the same enzyme solution.

Enzyme infiltration was also observed to be more effective with whole leaves than cut leaves (see FIG. 16B) when HA release was determined. Enzyme infiltration allows for a simpler extraction process, since whole leave or plants may be used and therefore the step of cutting the plant or plant material may be omitted.

Liquefaction of the leaf tissue may be obtained by the use of pectinase only, with efficient release of HA/VLPs. Enzyme infiltration of pectinases also works better with pectinases only, especially enzymes that have a high relative polygalacturonase content (for example Biocatalyst 162L/144L) compared with Biocatalyst 444L only. (FIG. 16C). Any pectinases may be used, alone or in combination with one another, as long as they have either, or both, Polygalacturonidase activity and Pectin Lyase activity. Suitable pectinases are for example "Biocatalyst 162L" and/or "Biocatalyst 144L". Enzyme infiltration allows for the use of a simpler digestion solution for example a solution that comprises pectinase only. Without wishing to be bound by theory, this solution may be less damaging to the protoplast.

As seen in FIG. 16D, with proper buffers and enzyme mixes, enzyme-assisted extraction of HA/VLPs can occur at pH near neutrality. Therefore the use of enzyme infiltration allows for the purification of pH-sensitive proteins.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A method of recovering proteins, protein suprastructures or virus-like particles (VLPs) from plant or plant matter, comprising:
   a. obtaining the plant or plant matter comprising apoplast-localized proteins, apoplast-localized protein suprastructures or apoplast-localized VLPs, the apoplast-localized protein suprastructures having a molecular weight from about 75 to about 1500 kDa;
   b. treating the plant or plant matter with a composition comprising from about 25 to about 250 mM ethylenediaminetetraacetic acid (EDTA) or ethylene glycol tetraacetic acid (EGTA) to loosen the cell wall to produce a plant or plant matter having a loosened cell wall, thereby releasing the apoplast-localized protein, apoplast-localized protein suprastructures, or apoplast-localized VLPs to produce a plant incubation mixture, separating the plant incubation mixture to produce a plant cell fraction and an apoplastic fraction; and
   c. recovering the proteins, protein suprastructures, or the VLPs from the apoplastic fraction.

2. The method of claim 1 wherein the composition comprises ethylenediaminetetraacetic acid (EDTA).

3. The method of claim 1 wherein in the step of obtaining (step a), the plant is transformed with a nucleic acid sequence encoding the protein, protein suprastructures, or VLPs, the protein, protein suprastructures, or VLPs being selected from the group of a protein, a protein rosette, a protein complex, a proteasome, a metabolon, a transcription complex, a recombination complex, a photosynthetic complex, a membrane transport complex, a nuclear pore complex, a protein nanoparticle, a glycoprotein, an antibody, a polyclonal antibody, a monoclonal antibody, a single chain monoclonal antibody, a virus like particle, a viral envelope protein, a viral structural protein, a viral capsid protein, and a viral coat protein, a chimeric protein, a chimeric protein complex, a chimeric protein nanoparticle, a chimeric glycoprotein, a chimeric antibody, a chimeric monoclonal antibody, a chimeric single chain monoclonal antibody, a chimeric hemagglutinin, and then the transformed plant or plant matter is harvested.

4. The method of claim 3, wherein the nucleic acid is introduced into the plant in a transient manner.

5. The method of claim 3, wherein, the nucleic acid is stably integrated within a genome of the plant.

6. The method of claim 1 wherein in the step of obtaining (step a)[ ], the plant is grown and the plant or plant matter is harvested.

7. The method of claim 3 wherein the nucleic acid encodes a monoclonal antibody or an influenza hemagglutinin.

8. The method of claim 1 wherein the plant-derived proteins, or protein suprastructures do not include neuraminidase or M protein.

9. The method of claim 1 wherein the plant matter is selected from the group of leaves, and cultured plant cells.

10. The method of claim 1 further comprising a step of d) purifying the proteins, protein suprastructures or VLPs, from the apoplastic fraction.

11. The method of claim 10, wherein the step of d) purifying comprises filtering the apoplastic fraction using depth filtration to produce a clarified extract, followed by chromatography of the clarified extract using size exclusion chromatography, cation exchange resin or affinity chromatography, or a combination thereof.

12. The method of claim 1, wherein the step of treating (step b), separating is performed by centrifugation, depth filtration, or a combination thereof.

13. The method of claim 1, wherein the composition is introduced into the plant or plant matter by infiltration under partial vacuum.

14. The method of claim 1, wherein the step of treating (step b) further comprises sonication.

15. The method of claim 1, wherein in the step of treating (step b), the composition further comprises an enzyme mixture.

16. The method of claim 15, wherein the enzyme mixture is introduced into the plant or plant matter by enzymatic infiltration.

17. The method of claim 16, wherein the enzymatic infiltration is selected from the group of vacuum or pressure infiltration.

18. The method of claim 15, wherein the enzyme mixture comprises one or more than one pectinase, one or more than one cellulase, or one or more than one pectinase and one or more than one cellulase.

19. The method of claim 15, wherein the enzyme mixture does not include one or more of a lipase, a protease or a pectinase.

\* \* \* \* \*

SEQUENCE LISTING

```
<160> NUMBER OF SEQ ID NOS: 16

<210> SEQ ID NO 1
<211> LENGTH: 3067
<212> TYPE: DNA
<213> ORGANISM: Artificial Sequence
<220> FEATURE:
<223> OTHER INFORMATION: Construct 685 for expressing H5/Indo

<400> SEQUENCE: 1
ttaattaaga attcgagctc caccgcggaa acctcctcgg attccattgc ccagctatct      60
gtcactttat tgagaagata gtggaaaagg aaggtggctc ctacaaatgc catcattgcg     120
ataaaggaaa ggccatcgtt gaagatgcct ctgccgacag tggtcccaaa gatggacccc     180
cacccacgag gagcatcgtg gaaaaagaag acgttccaac cacgtcttca aagcaagtgg     240
attgatgtga tatctccact gacgtaaggg atgacgcaca atcccactat ccttcgcaag     300
acccttcctc tatataagga agttcatttc atttggagag gtattaaaat cttaataggt     360
```

```
tttgataaaa gcgaacgtgg ggaaacccga accaaacctt cttctaaact ctctctcatc    420
tctcttaaag caaacttctc tcttgtcttt cttgcgtgag cgatcttcaa cgttgtcaga    480
tcgtgcttcg gcaccagtac aacgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggagaaaata gtgcttcttc ttgcaatagt cagtcttgtt    900
aaaagtgatc agatttgcat tggttaccat gcaaacaatt caacagagca ggttgacaca    960
atcatggaaa agaacgttac tgttacacat gcccaagaca tactggaaaa gacacacaac   1020
gggaagctct gcgatctaga tggagtgaag cctctaattt taagagattg tagtgtagct   1080
ggatggctcc tcgggaaccc aatgtgtgac gaattcatca atgtaccgga atggtcttac   1140
atagtggaga aggccaatcc aaccaatgac ctctgttacc cagggagttt caacgactat   1200
gaagaactga acacctatt gagcagaata aaccattttg agaaaattca aatcatcccc   1260
aaaagttctt ggtccgatca tgaagcctca tcaggagtta gctcagcatg tccatacctg   1320
ggaagtccct ccttttttag aaatgtggta tggcttatca aaagaacag tacatacccca   1380 acaataaaga aaagctacaa taataccaac caagaggatc ttttggtact gtggggaatt   1440
caccatccta atgatgcggc agagcagaca aggctatatc aaaacccaac cacctatatt   1500
tccattggga catcaacact aaaccagaga ttggtaccaa aaatagctac tagatccaaa   1560
gtaaacgggc aaagtggaag gatggagttc ttctggacaa ttttaaaacc taatgatgca   1620
atcaacttcg agagtaatgg aaatttcatt gctccagaat atgcatacaa aattgtcaag   1680 aaagggggact cagcaattat gaaaagtgaa ttggaatatg gtaactgcaa caccaagtgt   1740
caaactccaa tggggcgat aaactctagt atgccattcc acaacataca ccctctcacc   1800 atcgggaat gccccaaata tgtgaaatca aacagattag tccttgcaac agggctcaga   1860
aatagccctc aaagagagag cagaagaaaa aagagaggac tatttggagc tatagcaggt   1920
tttatagagg gaggatggca gggaatggta gatggttggt atgggtacca ccatagcaat   1980
gagcagggga gtgggtacgc tgcagacaaa gaatccactc aaaaggcaat agatggagtc   2040
accaataagg tcaactcaat cattgacaaa atgaacactc agtttgaggc cgttggaagg   2100
gaatttaata acttagaaag gagaatagag aatttaaaca agaagatgga agacgggttt   2160
ctagatgtct ggacttataa tgccgaactt ctggttctca tggaaaatga gagaactcta   2220
gactttcatg actcaaatgt taagaacctc tacgacaagg tccgactaca gcttagggat   2280
aatgcaaagg agctgggtaa cggttgtttc gagttctatc acaaatgtga taatgaatgt   2340
atggaaagta taagaaacgg aacgtacaac tatccgcagt attcagaaga agcaagatta   2400
aaaagagagg aaataagtgg ggtaaaattg gaatcaatag gaacttacca aatactgtca   2460
atttattcaa cagtggcgag ttccctagca ctggcaatca tgatggctgg tctatcttta   2520
tggatgtgct ccaatggatc gttacaatgc agaatttgca tttaaaggcc tattttcttt   2580
agtttgaatt tactgttatt cggtgtgcat ttctatgttt ggtgagcggt tttctgtgct   2640
cagagtgtgt ttatttttatg taatttaatt tctttgtgag ctcctgttta gcaggtcgtc   2700
```

```
ccttcagcaa ggacacaaaa agattttaat tttattaaaa aaaaaaaaaa aaaagaccgg    2760
gaattcgata tcaagcttat cgacctgcag atcgttcaaa catttggcaa taaagtttct    2820
taagattgaa tcctgttgcc ggtcttgcga tgattatcat ataatttctg ttgaattacg    2880
ttaagcatgt aataattaac atgtaatgca tgacgttatt tatgagatgg gttttatga    2940 ttagagtccc gcaattatac atttaatacg cgatagaaaa caaaatatag cgcgcaaact    3000
aggataaatt atcgcgcgcg gtgtcatcta tgttactaga ttctagagtc tcaagcttcg    3060
gcgcgcc                                                              3067
```

<210> SEQ ID NO 2
<211> LENGTH: 568
<212> TYPE: PRT
<213> ORGANISM: Artificial Sequence
<220> FEATURE:
<223> OTHER INFORMATION: Amino acid sequence encoded by construct 685
      for expressing H5/Indo

<400> SEQUENCE: 2

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285
```

-continued

```
Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Arg Gly Leu Phe Gly Ala Ile
            340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 3
<211> LENGTH: 24
<212> TYPE: DNA
<213> ORGANISM: Artificial Sequence
<220> FEATURE:
<223> OTHER INFORMATION: Primer pBinPlus.2613.c

<400> SEQUENCE: 3
aggaagggaa gaaagcgaaa ggag                                          24

<210> SEQ ID NO 4
<211> LENGTH: 56
<212> TYPE: DNA
<213> ORGANISM: Artificial Sequence
<220> FEATURE:
<223> OTHER INFORMATION: Primer Mut-ATG115.r

<400> SEQUENCE: 4
gtgccgaagc acgatctgac aacgttgaag atcgctcacg caagaaagac aagaga       56
```

```
<210> SEQ ID NO 5
<211> LENGTH: 52
<212> TYPE: DNA
<213> ORGANISM: Artificial Sequence
<220> FEATURE:
<223> OTHER INFORMATION: Primer Mut-ATG161.c

<400> SEQUENCE: 5
gttgtcagat cgtgcttcgg caccagtaca acgttttctt tcactgaagc ga           52

<210> SEQ ID NO 6
<211> LENGTH: 25
<212> TYPE: DNA
<213> ORGANISM: Artificial Sequence
<220> FEATURE:
<223> OTHER INFORMATION: Primer LC-C5-1.110r

<400> SEQUENCE: 6
tctcctggag tcacagacag ggtgg                                         25

<210> SEQ ID NO 7
<211> LENGTH: 39
<212> TYPE: DNA
<213> ORGANISM: Artificial Sequence
<220> FEATURE:
<223> OTHER INFORMATION: Primer LC-C5-1.110r

<400> SEQUENCE: 7
tgtcgggccc atggagaaaa tagtgcttct tcttgcaat                          39

<210> SEQ ID NO 8
<211> LENGTH: 37
<212> TYPE: DNA
<213> ORGANISM: Artificial Sequence
<220> FEATURE:
<223> OTHER INFORMATION: Primer H5 (A-Indo)-StuI.1707r

<400> SEQUENCE: 8
aaataggcct ttaaatgcaa attctgcatt gtaacga                            37

<210> SEQ ID NO 9
<211> LENGTH: 3111
<212> TYPE: DNA
<213> ORGANISM: Artificial Sequence
<220> FEATURE:
<223> OTHER INFORMATION: Nucleic acid sequence (construct 660)

<400> SEQUENCE: 9
agaggtaccc cgggctggta tatttatatg ttgtcaaata actcaaaaac cataaaagtt   60
taagttagca agtgtgtaca tttttacttg aacaaaaata ttcacctact actgttataa   120
atcattatta aacattagag taaagaaata tggatgataa gaacaagagt agtgatattt   180
tgacaacaat tttgttgcaa catttgagaa aattttgttg ttctctcttt tcattggtca   240
aaaacaatag agagagaaaa aggaagaggg agaataaaaa cataatgtga gtatgagaga   300
gaaagttgta caaaagttgt accaaaatag ttgtacaaat atcattgagg aatttgacaa   360
aagctacaca ataagggtt aattgctgta aataaataag gatgacgcat tagagagatg    420
taccattaga gaattttttgg caagtcatta aaaagaaaga ataaattatt tttaaaatta  480
aaagttgagt catttgatta aacatgtgat tatttaatga attgatgaaa gagttggatt   540
aaagttgtat tagtaattag aatttggtgt caaatttaat ttgacatttg atctttttcct  600 atatattgcc ccatagagtc agttaactca tttttatatt tcatagatca aataagagaa   660
```

```
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt    1020
cttgcaatag tcagtcttgt taaaagtgat cagatttgca ttggttacca tgcaaacaat    1080
tcaacagagc aggttgacac aatcatggaa aagaacgtta ctgttacaca tgcccaagac    1140
atactggaaa agacacacaa cgggaagctc tgcgatctag atggagtgaa gcctctaatt    1200
ttaagagatt gtagtgtagc tggatggctc ctcgggaacc caatgtgtga cgaattcatc    1260
aatgtaccgg aatggtctta catagtggag aaggccaatc caaccaatga cctctgttac    1320
ccagggagtt tcaacgacta tgaagaactg aaacacctat tgagcagaat aaaccatttt    1380
gagaaaattc aaatcatccc caaaagttct tggtccgatc atgaagcctc atcaggagtt    1440
agctcagcat gtccataccc tgggaagtcc ctccttttta gaaatgtggt atggcttatc    1500
aaaaagaaca gtacataccc aacaataaag aaaagctaca ataataccaa ccaagaggat    1560
cttttggtac tgtggggaat tcaccatcct aatgatgcgg cagagcagac aaggctatat    1620
caaaacccaa ccacctatat ttccattggg acatcaacac taaaccagag attggtacca    1680
aaaatagcta ctagatccaa agtaaacggg caaagtggaa ggatggagtt cttctggaca    1740 atttttaaaac ctaatgatgc aatcaacttc gagagtaatg gaaatttcat tgctccagaa    1800
tatgcataca aaattgtcaa gaaagggggac tcagcaatta tgaaaagtga attggaatat    1860
ggtaactgca acaccaagtg tcaaactcca atgggggcga taaactctag tatgccattc    1920
cacaacatac accctctcac catcgggaa tgccccaaat atgtgaaatc aaacagatta    1980
gtccttgcaa cagggctcag aaatagccct caaagagaga gcagaagaaa aaagagagga    2040
ctatttggag ctatagcagg ttttatagag ggaggatggc agggaatggt agatggttgg    2100
tatgggtacc accatagcaa tgagcagggg agtgggtacg ctgcagacaa agaatccact    2160
caaaaggcaa tagatggagt caccaataag gtcaactcaa tcattgacaa aatgaacact    2220
cagtttgagg ccgttggaag ggaatttaat aacttagaaa ggagaataga gaatttaaac    2280
aagaagatgg aagacgggtt tctagatgtc tggacttata atgccgaact tctggttctc    2340
atggaaaatg agagaactct agactttcat gactcaaatg ttaagaacct ctacgacaag    2400
gtccgactac agcttaggga taatgcaaag gagctgggta acggttgttt cgagttctat    2460
cacaaatgtg ataatgaatg tatggaaagt ataagaaacg gaacgtacaa ctatccgcag    2520
tattcagaag aagcaagatt aaaaagagag gaaataagtg gggtaaaatt ggaatcaata    2580
ggaacttacc aaatactgtc aatttattca acagtggcga gttccctagc actggcaatc    2640
atgatggctg gtctatcttt atggatgtgc tccaatggat cgttacaatg cagaatttgc    2700
atttaagagc tctaagttaa aatgcttctt cgtctcctat ttataatatg gtttgttatt    2760
gttaattttg ttcttgtaga agagcttaat taatcgttgt tgttatgaaa tactatttgt    2820
atgagatgaa ctggtgtaat gtaattcatt tacataagtg gagtcagaat cagaatgttt    2880
cctccataac taactagaca tgaagacctg ccgcgtacaa ttgtcttata tttgaacaac    2940
taaaattgaa catcttttgc cacaacttta taagtggtta atatagctca aatatatggt    3000
caagttcaat agattaataa tggaaatatc agttatcgaa attcattaac aatcaactta    3060
```

```
acgttattaa ctactaattt tatatcatcc cctttgataa atgatagtac a           3111

<210> SEQ ID NO 10
<211> LENGTH: 26
<212> TYPE: PRT
<213> ORGANISM: Artificial Sequence
<220> FEATURE:
<223> OTHER INFORMATION: PDI signal peptide

<400> SEQUENCE: 10

Met Ala Lys Asn Val Ala Ile Phe Gly Leu Leu Phe Ser Leu Leu Leu
1               5                   10                  15

Leu Val Pro Ser Gln Ile Phe Ala Glu Glu
            20                  25

<210> SEQ ID NO 11
<211> LENGTH: 25
<212> TYPE: DNA
<213> ORGANISM: Artificial Sequence
<220> FEATURE:
<223> OTHER INFORMATION: Primer Plasto-443c

<400> SEQUENCE: 11
gtattagtaa ttagaatttg gtgtc                                         25

<210> SEQ ID NO 12
<211> LENGTH: 34
<212> TYPE: DNA
<213> ORGANISM: Artificial Sequence
<220> FEATURE:
<223> OTHER INFORMATION: Primer supP19-plasto.r

<400> SEQUENCE: 12
ccttgtatag ctcgttccat tttctctcaa gatg                               34

<210> SEQ ID NO 13
<211> LENGTH: 20
<212> TYPE: DNA
<213> ORGANISM: Artificial Sequence
<220> FEATURE:
<223> OTHER INFORMATION: Primer supP19-1c

<400> SEQUENCE: 13
atggaacgag ctatacaagg                                               20

<210> SEQ ID NO 14
<211> LENGTH: 32
<212> TYPE: DNA
<213> ORGANISM: Artificial Sequence
<220> FEATURE:
<223> OTHER INFORMATION: Primer SupP19-SacI.r

<400> SEQUENCE: 14
agtcgagctc ttactcgctt tcttttttcga ag                                32

<210> SEQ ID NO 15
<211> LENGTH: 1214
<212> TYPE: DNA
<213> ORGANISM: Artificial Sequence
<220> FEATURE:
<223> OTHER INFORMATION: Construct 590

<400> SEQUENCE: 15
cactttgtga gtctacactt tgattccctt caaacacata caaagagaag agactaatta   60
```

-continued

| | |
|---|---|
| attaattaat catcttgaga gaaaatggat tttcaggtgc agattatcag cttcctgcta | 120 |
| atcagtgctt cagtcataat gtccagagga caaattgttc tctcccagtc tccagcaatc | 180 |
| ctgtctgcat ctccagggga aaggtcaca atgacttgca gggccagctc aagtgtaagt | 240 |
| tacatccact ggttccagca aaagccagga tcctccccca aaccctggat ttatgccaca | 300 |
| tccaacctgg cttctggagt ccctgttcgc ttcagtggca gtgggtctgg gacttcttac | 360 |
| tctctcacaa tcagcagagt ggaggctgaa gatgctgcca cttattactg ccagcagtgg | 420 |
| actagtaacc cacccacgtt cggaggggg accaagctgg aaatcaaacg tacggtggct | 480 |
| gcaccatctg tcttcatctt cccgccatct gatgagcagt tgaaatctgg aactgcctct | 540 |
| gttgtgtgcc tgctgaataa cttctatccc agagaggcca agtacagtg aaggtggat | 600 |
| aacgccctcc aatcgggtaa ctcccaggag agtgtcacag agcaggacag caaggacagc | 660 |
| acctacagcc tcagcagcac cctgacgctg agcaaagcag actacgagaa acacaaagtc | 720 |
| tacgcctgcg aagtcaccca tcagggcctg agctcgcccg tcacaaagag cttcaacagg | 780 |
| ggagagtgtt gagacgtcgt taaaatgctt cttcgtctcc tatttataat atggtttgtt | 840 |
| attgttaatt ttgttcttgt agaagagctt aattaatcgt tgttgttatg aaatactatt | 900 |
| tgtatgagat gaactggtgt aatgtaattc atttacataa gtggagtcag aatcagaatg | 960 |
| tttcctccat aactaactag acatgaagac ctgccgcgta caattgtctt atatttgaac | 1020 |
| aactaaaatt gaacatcttt tgccacaact ttataagtgg ttaatatagc tcaaatatat | 1080 |
| ggtcaagttc aatagattaa taatggaaat atcagttatc gaattcatt aacaatcaac | 1140 |
| ttaacgttat taactactaa ttttatatca tccccttga taaatgatag tacaccaatt | 1200 |
| aggaaggaga attc | 1214 |

<210> SEQ ID NO 16
<211> LENGTH: 1919
<212> TYPE: DNA
<213> ORGANISM: Artificial Sequence
<220> FEATURE:
<223> OTHER INFORMATION: Construct No. 592

<400> SEQUENCE: 16

| | |
|---|---|
| cactttgtga gtctacactt tgattccctt caaacacata caaagagaag agactaatta | 60 |
| attaattaat catcttgaga gaaaatgggt tggagcctca tcttgctctt ccttgtcgct | 120 |
| gttgctacgc gtgtcctgtc ccaggtacaa ctgcagcagc ctggggctga gctggtgaag | 180 |
| cctggggcct cagtgaagat gtcctgcaag gcttctggct acacatttac cagttacaat | 240 |
| atgcactggg taaaacagac acctggtcgg ggcctggaat ggattggagc tatttatccc | 300 |
| ggaaatggtg atacttccta caatcagaag ttcaaaggca aggccacatt gactgcagac | 360 |
| aaatcctcca gcacagccta catgcagctc agcagcctga tctgaggga ctctgcggtc | 420 |
| tattactgtg caagatcgac ttactacggg ggtgactggt acttcaatgt ctggggcgca | 480 |
| gggaccacgg tcaccgtctc tgcagctagc accaggggcc catcggtctt ccccctggca | 540 |
| ccctcctcca agagcacctc tgggggcaca gcggccctgg gctgcctggt caaggactac | 600 |
| ttccccgaac cggtgacggt gtcgtggaac tcaggcgccc tgaccagcgg cgtgcacacc | 660 |
| ttcccggctg tcctacagtc ctcaggactc tactccctca gcagcgtggt gaccgtgccc | 720 |
| tccagcagct gggcaccca gacctacatc tgcaacgtga atcacaagcc cagcaacacc | 780 |
| aaggtggaca agaaagttga gcccaaatct tgtgacaaaa ctcacacatg cccaccgtgc | 840 |
| ccagcacctg aactcctggg gggaccgtca gtcttcctct tccccccaaa acccaaggac | 900 |

```
accctcatga tctcccggac ccctgaggtc acatgcgtgg tggtggacgt gagccacgaa      960
gaccctgagg tcaagttcaa ctggtacgtg gacggcgtgg aggtgcataa tgccaagaca     1020
aagccgcggg aggagcagta caacagcacg taccgtgtgg tcagcgtcct caccgtcctg     1080
caccaggact ggctgaatgg caaggagtac aagtgcaagg tctccaacaa agccctccca     1140
gcccccatcg agaaaaccat ctccaaagcc aaagggcagc ctagggaacc acaagtgtac     1200
actcttccac catctaggga tgagcttact aagaaccaag tttctcttac ttgtcttgtg     1260
aagggatttt atccatctga catcgccgtg gaatgggaat ccaacggaca accagagaac     1320
aattacaaga ctactccacc agttcttgat tctgatggat ccttctttct ttattccaag     1380
cttactgttg ataagtccag atggcagcaa ggaaatgtgt tctcttgttc tgttatgcac     1440
gaagctcttc ataatcatta tactcaaaag tccctttctc tttctcctgg aaagtgagac     1500
gtcgttaaaa tgcttcttcg tctcctattt ataatatggt ttgttattgt taattttgtt     1560
cttgtagaag agcttaatta atcgttgttg ttatgaaata ctatttgtat gagatgaact     1620
ggtgtaatgt aattcattta cataagtgga gtcagaatca gaatgtttcc tccataacta     1680
actagacatg aagacctgcc gcgtacaatt gtcttatatt tgaacaacta aaattgaaca     1740
tcttttgcca caactttata agtggttaat atagctcaaa tatatggtca agttcaatag     1800
attaataatg gaaatatcag ttatcgaaat tcattaacaa tcaacttaac gttattaact     1860
actaatttta tatcatcccc tttgataaat gatagtacac caattaggaa ggagaattc      1919
```